US008431540B2

(12) United States Patent  
Larsen et al.

(10) Patent No.: US 8,431,540 B2
(45) Date of Patent: *Apr. 30, 2013

(54) MODIFIED LYSINE-MIMETIC COMPOUNDS

(75) Inventors: Bjarne Due Larsen, Roskilde (DK); Jørgen Søberg Petersen, Hellebæk (DK); Ketil Jørgen Haugan, Slangerup (DK); John A. Butera, Clarksburg, NJ (US); James K. Hennan, Harleysville, PA (US); Edward H. Kerns, Skillman, NJ (US); Evgueni Lvovich Piatnitski, Conshohocken, PA (US)

(73) Assignee: Zealand Pharma A/S, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/234,956

(22) Filed: Sep. 16, 2011

(65) Prior Publication Data

US 2012/0245106 A1  Sep. 27, 2012

Related U.S. Application Data

(60) Continuation of application No. 12/610,172, filed on Oct. 30, 2009, now Pat. No. 8,026,272, which is a division of application No. 11/643,192, filed on Dec. 21, 2006, now Pat. No. 7,622,496.

(60) Provisional application No. 60/753,628, filed on Dec. 23, 2005.

(51) Int. Cl.
A61K 38/05 (2006.01)
A61P 9/10 (2006.01)

(52) U.S. Cl.
USPC ....................................... 514/21.91

(58) Field of Classification Search ............ None
See application file for complete search history.

(56) References Cited

U.S. PATENT DOCUMENTS

| 4,780,528 | A | 10/1988 | Takemoto et al. | |
|---|---|---|---|---|
| 5,120,859 | A | 6/1992 | Webb | |
| 5,707,991 | A | 1/1998 | Capet et al. | |
| 6,399,629 | B1 | 6/2002 | Chamberland et al. | |
| 7,741,356 | B2 | 6/2010 | Breslin et al. | |
| 8,026,272 | B2 * | 9/2011 | Larsen et al. | 514/423 |
| 2007/0232574 | A1 | 10/2007 | Galey et al. | |
| 2008/0188545 | A1 | 8/2008 | Alimardanov et al. | |

FOREIGN PATENT DOCUMENTS

| CN | 1528745 A | 9/2004 |
|---|---|---|
| DE | 3831936 A1 | 4/1989 |
| EP | 0052991 B1 | 6/1982 |
| EP | 0088350 B1 | 2/1985 |
| EP | 0071544 B1 | 10/1986 |
| EP | 0254032 A2 | 1/1988 |
| EP | 0132304 B1 | 6/1989 |
| EP | 0566157 A1 | 10/1993 |
| EP | 0175266 B1 | 3/1996 |
| EP | 0672700 B1 | 6/1999 |
| EP | 1604977 A1 | 12/2005 |
| EP | 1227805 B1 | 5/2006 |
| GB | 2159160 A | 11/1985 |
| WO | WO 95/13069 | 5/1995 |
| WO | WO 95/30647 | 11/1995 |
| WO | WO 96/09820 | 4/1996 |
| WO | WO 97/36873 | 10/1997 |
| WO | WO 98/08815 | 3/1998 |
| WO | WO 98/10653 | 3/1998 |
| WO | WO 98/17679 | 4/1998 |
| WO | WO 98/25897 | 6/1998 |
| WO | WO 99/09991 | 3/1999 |
| WO | WO 00/23421 | 4/2000 |
| WO | WO 01/07436 A2 | 2/2001 |
| WO | WO 01/26644 A2 | 4/2001 |
| WO | WO 01/34594 A1 | 5/2001 |
| WO | WO 01/62775 A2 | 8/2001 |
| WO | WO 01/74796 A1 | 10/2001 |
| WO | WO 01/79162 A2 | 10/2001 |
| WO | WO 01/83517 A1 | 11/2001 |
| WO | WO 01/98344 A2 | 12/2001 |
| WO | WO 02/08244 A2 | 1/2002 |
| WO | WO 02/08251 A2 | 1/2002 |
| WO | WO 02/08256 A2 | 1/2002 |
| WO | WO 02/30421 A2 | 4/2002 |
| WO | WO 02/30462 A2 | 4/2002 |
| WO | WO 02/32869 A2 | 4/2002 |
| WO | WO 02/39976 A1 | 5/2002 |
| WO | WO 02/089738 A2 | 11/2002 |
| WO | WO 03/013571 A1 | 2/2003 |
| WO | WO 03/062228 A1 | 7/2003 |
| WO | WO 03/062265 A2 | 7/2003 |
| WO | WO 03/072528 A2 | 9/2003 |
| WO | WO 2004/005248 A1 | 1/2004 |
| WO | WO 2004/020599 A2 | 3/2004 |
| WO | WO 2004/045518 A2 | 6/2004 |
| WO | WO 2004/048400 | 6/2004 |

(Continued)

OTHER PUBLICATIONS

Hennan et al., caplus an 2009:1153165.*
Prevent-Ischemia, http://www.mayoclinic.com/health/myocardial-ischemia/DS01179/DSECTION=prevention, 2012.*
Atrial-Fibrillation, 2012, http://www.hindawi.com/journals/srt/2011/208694/.*
Carmichael, THe Journal of the American Society for Experimental NeuroTherapeutics, 2005, 2, 396-409.*
Watkins et al., "The Relationship Between Physicochemical Properties, In Vitro Activity and Pharmacokinetic Profiles of Analogues of Diamine-Containing Efflux Pump Inhibitors," *Bioorg. Med. Chem. Lett.* 13:421-4244 (2003).
Yelin et al., "Stereochemistry of Reductive Amination of 4-Ocoproline Derivatives with Glycine Esters," *Russ. J. Bioorg Chem* 28:444-449 (2002).
De Diego et al., "New Gly-Pro-Glu (GPE) analogues: Expedite solid-phase synthesis and biological activity," *Biorganic & Medicinal Chemistry Letters* 16: 1392-1396 (2006).

(Continued)

*Primary Examiner* — Sun Jae Loewe
(74) *Attorney, Agent, or Firm* — Clark & Elbing LLP; Kristina Bieker-Brady

(57) ABSTRACT

Lysine mimetic compounds having useful pharmacological activity such as antiarrhythmic activity and desirable bioavailability properties are disclosed.

14 Claims, 1 Drawing Sheet

FOREIGN PATENT DOCUMENTS

| WO | WO 2004/087646 A2 | 10/2004 |
|---|---|---|
| WO | WO 2004/099134 A2 | 11/2004 |
| WO | WO 2005/037214 A2 | 4/2005 |
| WO | WO 2005/070919 A1 | 8/2005 |
| WO | WO 2005/085197 A1 | 9/2005 |
| WO | WO 2005/095403 A2 | 10/2005 |
| WO | WO 2006/020276 A2 | 2/2006 |
| WO | WO 2006/114401 A2 | 11/2006 |
| WO | WO 2006/125227 A2 | 11/2006 |
| WO | WO 2008/079266 A2 | 7/2008 |

OTHER PUBLICATIONS

European Patent Office Communication for European Application No. 06 849 152.1, dated Oct. 24, 2011.

European Patent Office Communication for European Application No. 06 849 152.1, dated Aug. 31, 2008.

Alzheimer's Disease Treatment Phases, http://alzheimerstreatment.org/treatment/disease-treatment.htm (2008).

Alzheimer's Drugs, Consumer Reports Best Buy Drugs, pp. 1-5, 2008.

Antarrhythmic agent, 2011, http://en.wikipedia.org/wiki/Antiarrhythmic_agent.

Database Registry, Database Accession No. 90559-49-2, 1984.

Gangamani et al., "Synthesis of Nα-(Purinyl/Pyrimidinyl Acetyl)-4-Aminoproline Diastereomers with Potential Use in PNA Synthesis," *Tetrahedron* 52:15017-15030, 1996.

Hennan et al., "GAP-134 ([2S,4R]-1[2-Aminoacetyl]4-Benzamidopyrrolidine-2-Carboxylic Acid) Prevents Spontaneous Ventricular Arrhythmias and Reduces Infarct Size during Myocardial Ischemia/Reperfusion Injury in Open-Chest Dogs," *J. Cardiovasc. Pharmacol. Ther.* 14:207-214, 2009.

Moradu et al., *Treatment of Atrial Fibrillation*, pp. 1-12, 2009.

Neiss et al., CAplus an 1986:479371, 1986.

Petrillo et al., CAplus an 1985:25039, 1985.

Pfeifer et al., "Stabilisation of β-hairpin Conformations in a Protein Surface Mimetic Using a Bicyclic Template Derived from (2S, 3R, 4R)-diaminoproline," *Chem. Commun.* pp. 1977-1978, 1998.

Pfeifer et al., "Synthesis and Solution Conformation of β-hairpin Mimetics Utilizing a Template Derived from (2S, 3R, 4R)-diaminoproline," *Helvetica Chimica Acta* 83:444-464, 2000.

International Search Report for International Application No. PCT/US2006/048790, mailed Sep. 27, 2007.

* cited by examiner

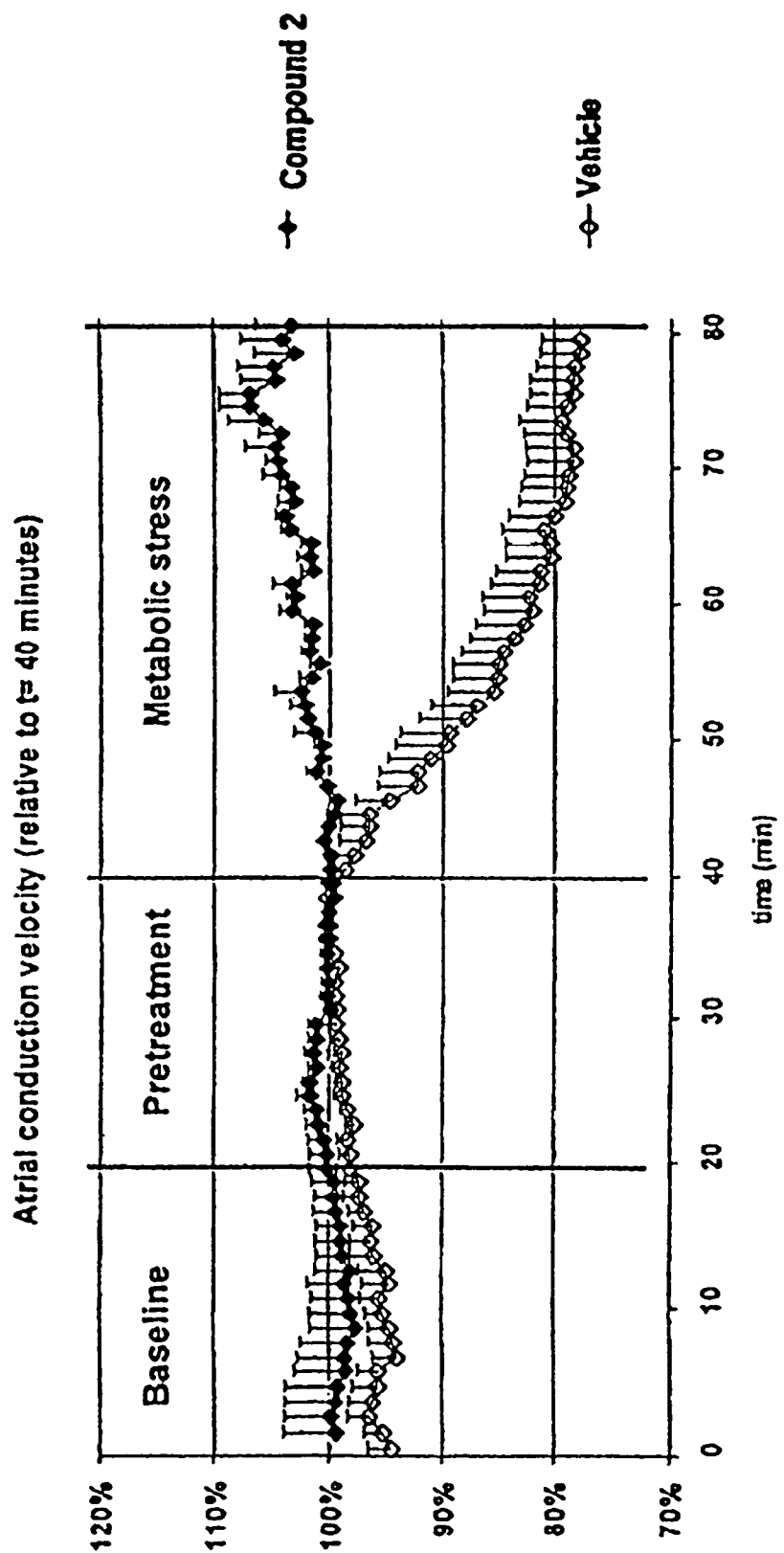

MODIFIED LYSINE-MIMETIC COMPOUNDS

CROSS REFERENCE TO RELATED APPLICATIONS

This application is a continuation of U.S. application Ser. No. 12/610,172, filed on Oct. 30, 2009, which is a divisional of U.S. application Ser. No. 11/643,192, filed on Dec. 21, 2006, which claims priority to and the benefit of U.S. Provisional Patent Application Ser. No. 60/753,628, filed Dec. 23, 2005, each of which is incorporated herein by reference.

FIELD

The present teachings relate to lysine mimetic compounds having pharmacological activity, such as antiarrhythmic activity, and desirable bioavailability properties. The present teachings further relate to pharmaceutical compositions comprising such compounds and methods of using and making such compounds and compositions.

BACKGROUND

There is increasing recognition that intercellular communication is essential for cellular homeostasis, proliferation and differentiation. Such communication is believed to be facilitated by gap junctions. These structures are thought to be a route for coupling cells and permitting "cross-talk." (See generally, Sperelakis N., eds., *Cell Interactions and Gap Junctions*, CRC Press, Inc. (1989)). The cross-talk between gap junctions is referred to as "gap junctional intercellular communication" (GJIC).

Generally, gap junctions are specialized regions of the cell membrane that contain clusters of hundreds to thousands of densely packed channels that directly connect the cytoplasm of two adjacent cells. The gap junction channels are composed of two hemichannels, or connexons, provided by each of two neighboring cells. Each connexon, in turn, is made up of six proteins called connexins.

In the heart, conduction of electrical impulses takes place through gap junctions. Abnormal GJIC has been linked to a variety of disease states, including heart disease. For example, it has been shown that mice heterozygous for the Cx43 gene, which codes for a specific ventricular connexin, develop spontaneous ventricular arrhythmias and suffer from sudden cardiac death. (Guerrero et al., *J. Clin. Invest.*, 99, 1991-1998 (1997)). Reduced expression of Cx43 in heterozygous mice is directly linked to an increased incidence of ventricular arrhythmias during ischemia. (Lerner et al., *Circulation*, 101, 547-552 (2000)). Several other studies have shown reduced expression or altered distribution of Cx43 in chronically ischemic, hibernating, or hypertrophied hearts. (Kaprelian et al., *Circulation*, 97, 651-660 (1998); Peters et al., *Circulation*, 88, 864-875 (1993); Saffitz et al., *Cardiovasc. Res.*, 42, 309-317 (1999)).

Several peptides that influence GJIC have been identified, including antiarrhythmic peptides AAP (Aonuma et al., *Chem. Pharm. Bull.* (Tokyo), 28, 3332-3339 (1980)), AAP10 (Dhein et al., *Naunyn Schmiedebergs Arch Pharmacol.*, 350, 174-184 (1994); Muller et al., *Eur. J. Pharmacol.*, 327, 65-72 (1997)), and HP5 (disclosed in U.S. Pat. No. 4,775,743). However, these peptides exhibit undesirable characteristics, including low stability, short half-life, and a lack of oral bioavailability.

SUMMARY

Broadly, the present teachings relate to lysine mimetic compounds having useful pharmacological activity, such as antiarrhythmic activity, and desirable bioavailability properties. The present teachings provide compounds represented generally by Formula I:

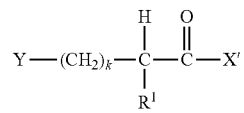

and pharmaceutically acceptable salts, esters, hydrates, and prodrugs thereof, wherein Y is OX, $OR^2$, $NXR^2$, or $NR^2R^3$; k is 0, 1, or 2; X is H or a lysine mimetic; X' is $OR^3$, $NR^2R^3$, or a lysine mimetic; $R^1$ is H, an optionally substituted $C_{1-10}$ alkyl, an optionally substituted $C_{6-20}$ aryl, an optionally substituted $C_{7-20}$ aralkyl, or an amino acid side chain; and $R^2$ and $R^3$ are defined as described herein.

Particular examples of compounds according to the present teachings include 4-amino-pyrrolidine-2-carboxylic acid (4-aminoproline, 4 Amp) analogs having Formula II or Formula III:

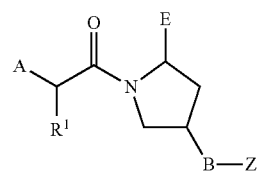

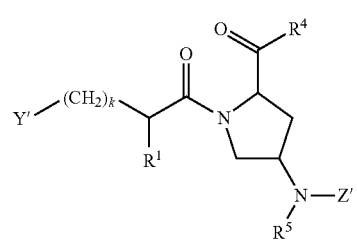

and pharmaceutically acceptable salts, esters, hydrates, and prodrugs thereof, wherein A, B, E, k, $R^1$, $R^4$, $R^5$, Y', Z and Z' are defined herein.

BRIEF DESCRIPTION OF THE FIGURES

FIG. 1 shows the results of a test to study the effect of the compounds on metabolic stress induced atrial conduction slowing and in an in vitro model as described in Haugan et al., *J. Cardiovasc. Electrophysiol.*, 16, 537-545 (2005).

DETAILED DESCRIPTION

In one aspect, the present teachings provide compounds represented by Formula I:

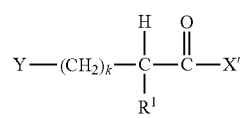

and pharmaceutically acceptable salts, esters, hydrates and prodrugs thereof;

wherein:
Y is selected from OX, OR$^2$, NXR$^2$, and NR$^2$R$^3$;
k is 0, 1, or 2;
X is H or a lysine mimetic;
X' is selected from OR$^3$, NR$^2$R$^3$, and a lysine mimetic;
R$^1$ is selected from H, an optionally substituted C$_{1-10}$ alkyl, an optionally substituted C$_{6-20}$ aryl, an optionally substituted C$_{7-20}$ aralkyl, and an amino acid side chain;
R$^2$ and R$^3$ each independently is selected from H, an optionally substituted C$_{1-10}$ alkyl, an optionally substituted C$_{3-20}$ cycloalkyl, an optionally substituted C$_{7-20}$ aralkyl, an optionally substituted C$_{6-20}$ aryl, an optionally substituted 3-20 membered cycloheteroalkyl, an optionally substituted 5-20 membered heteroaryl, C(O)R$^6$, C(O)OR$^6$, C(O)NR$^6$R$^7$, S(O)$_2$R$^6$, and S(O)$_2$NR$^6$R$^7$;
alternatively, R$^2$ and R$^3$ together with the nitrogen atom to which they are bound form a 3-20 membered heterocycle optionally containing 1-4 ring heteroatoms independently selected from O, N and S and optionally substituted with 1-5 Q groups;
R$^6$ and R$^7$ each independently is selected from H, an optionally substituted C$_{1-10}$ alkyl, an optionally substituted C$_{3-20}$ cycloalkyl, an optionally substituted C$_{2-10}$ alkenyl, an optionally substituted C$_{2-10}$ alkynyl, an optionally substituted C$_{6-20}$ aryl, an optionally substituted C$_{7-20}$ aralkyl, an optionally substituted 3-20 membered cycloheteroalkyl, an optionally substituted 5-20 membered heteroaryl, C(O)R$^8$, C(O)OR$^8$, and C(O)NR$^8$R$^9$;
alternatively, R$^6$ and R$^7$ together with the nitrogen atom to which they are bound form a 3-20 membered heterocycle optionally containing 1-4 ring heteroatoms independently selected from O, N and S and optionally substituted with 1-5 Q groups;
R$^8$ and R$^9$ each independently is selected from H, an optionally substituted C$_{1-10}$ alkyl, an optionally substituted C$_{3-20}$ cycloalkyl, an optionally substituted C$_{2-10}$ alkenyl, an optionally substituted C$_{2-10}$ alkynyl, an optionally substituted C$_{6-20}$ aryl, an optionally substituted C$_{7-20}$ aralkyl, an optionally substituted 3-20 membered cycloheteroalkyl, and an optionally substituted 5-20 membered heteroaryl;
Q, at each occurrence, independently is selected from an optionally substituted C$_{1-10}$ alkyl, an optionally substituted C$_{2-10}$ alkenyl, an optionally substituted C$_{2-10}$ alkynyl, an optionally substituted C$_{3-20}$ cycloalkyl, an optionally substituted C$_{6-20}$ aryl, an optionally substituted C$_{7-20}$ aralkyl, an optionally substituted 3-20 membered cycloheteroalkyl, an optionally substituted 5-20 membered heteroaryl, F, Cl, Br, I, CN, CF$_3$, OCF$_3$, NO$_2$, OR$^8$, SR$^8$, S$^+$R$^8$$_2$, S(O)R$^8$, S(O)$_2$R$^8$, S(O)$_2$OH, S(O)$_2$NR$^8$R$^9$, NR$^8$S(O)$_2$R$^9$, C(O)R$^8$, C(O)OR$^8$, C(O)NR$^8$R$^9$, OC(O)R$^8$, NR$^8$R$^9$, NR$^8$C(O)R$^9$, NR$^8$C(O)OR$^9$, NR$^8$C(O)NR$^8$R$^9$, and N$^+$R$^8$$_3$; provided:
a) when Y is OX or NXR$^2$ and X is H, X' is a lysine mimetic;
b) when Y is OR$^2$ or NR$^2$R$^3$, X' is a lysine mimetic; and
c) the compound is not 1-(2-aminopropanoyl)-4-benzamidopyrrolidine-2-carboxylic acid or 1-(2-aminopropanoyl)-4-benzamidopiperidine-2-carboxylic acid.

Some embodiments of the present teachings include those compounds and pharmaceutically acceptable salts, esters, hydrates and prodrugs thereof, wherein Y is OX or NXR$^2$, X' is OR$^3$ or NR$^2$R$^3$, and X is a lysine mimetic, wherein the lysine mimetic is selected from:

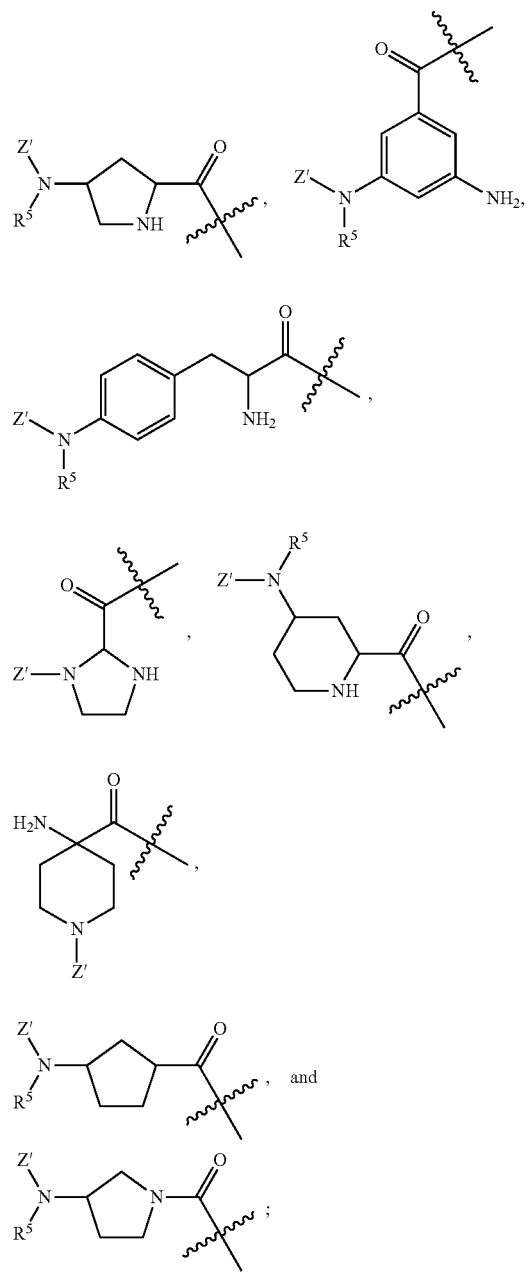

wherein:
Z' is selected from H, (CH$_2$)$_m$—C$_{6-20}$ aryl, (CH$_2$)$_m$-5-20 membered heteroaryl, C(O)(CH$_2$)$_m$—C$_{6-20}$ aryl, C(O)(CH$_2$)$_m$-5-20 membered heteroaryl, (CH$_2$)$_m$C(O)—C$_{6-20}$ aryl, (CH$_2$)$_m$C(O)-5-20 membered heteroaryl, S(O)$_2$(CH$_2$)$_m$—C$_{6-20}$ aryl, and S(O)$_2$(CH$_2$)$_m$-5-20 membered heteroaryl, wherein each of the C$_{6-20}$ aryl and 5-20 membered heteroaryl is optionally substituted with 1-5 Q groups;
R$^5$ is H or an optionally substituted C$_{1-10}$ alkyl;
m is 0, 1, or 2; and
Q, R$^2$ and R$^3$ are defined as described above.

In other embodiments, Y is OR$^2$, NR$^2$R$^3$, OX or NXR$^2$, X is H, and X' is a lysine mimetic, wherein the lysine mimetic is selected from:

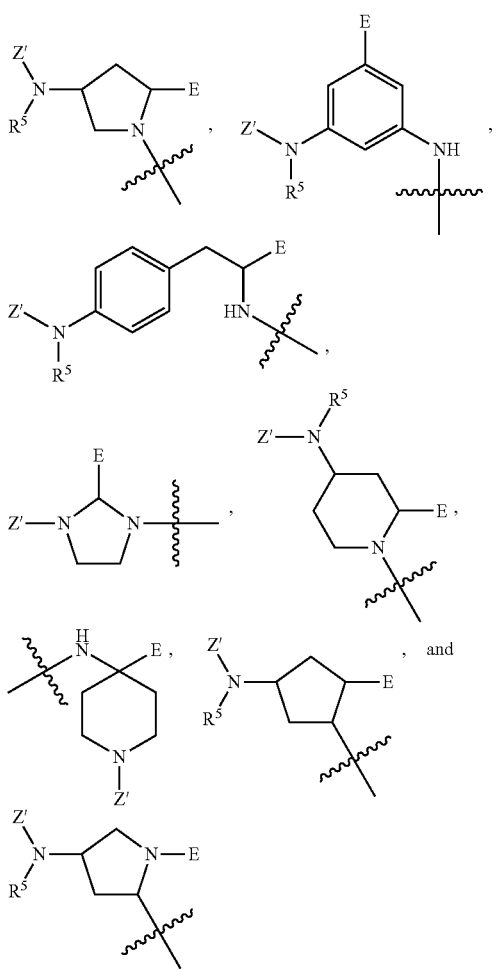

wherein:

Z' is selected from H, $(CH_2)_m$—$C_{6-20}$ aryl, $(CH_2)_m$-5-20 membered heteroaryl, $C(O)(CH_2)_m$—$C_{6-20}$ aryl, $C(O)(CH_2)_m$-5-20 membered heteroaryl, $(CH_2)_mC(O)$—$C_{6-20}$ aryl, $(CH_2)_mC(O)$-5-20 membered heteroaryl, $S(O)_2(CH_2)_m$—$C_{6-20}$ aryl, and $S(O)_2(CH_2)_m$-5-20 membered heteroaryl, wherein each of the $C_{6-20}$ aryl and 5-20 membered heteroaryl is optionally substituted with 1-5 Q groups;

$R^5$ is H or an optionally substituted $C_{1-10}$ alkyl;

m is 0, 1, or 2;

E is selected from $C(O)OR^6$, $C(O)NR^6R^7$, and a carboxylic acid bioisostere; and Q, $R^2$, $R^3$, $R^6$ and $R^7$ are defined as described above.

In some examples of these embodiments, E is C(O)OH. In other examples, E is $C(O)NR^6R^7$ (e.g., $C(O)NHR^7$ or $C(O)NH_2$).

In any of the compounds of the present teachings, Z' can be $C(O)(CH_2)_m$—$C_{6-20}$ aryl optionally substituted with 1-5 Q groups and m can be 0. For example, Z' can be benzoyl.

In some embodiments of the compounds of the present teachings, $R^1$ is H. In other embodiments, $R^1$ is an amino acid side chain. Examples of suitable amino acid side chains for $R^1$ can include, but are not limited to, the side chains of valine, norvaline, leucine, norleucine, isoleucine, methionine, alanine, phenylalanine, tyrosine, tryptophan, serine, threonine, cysteine, lysine, argenine, histidine, aspartic acid, glutamic acid, asparagine, glutamine, ornithine, 2,4-diaminobutyric acid, and 2,6-diaminopimelic acid.

In some embodiments, k is 0; in others, k is 1.

Particular compounds of the present teachings have structures represented by Formulae I(a)-I(p) below, wherein X' is $OR^3$ (e.g., OH) or $NR^2R^3$ (e.g., $NH_2$), Y is $OR^2$ (e.g., OH) or $NR^2R^3$ (e.g., $NH_2$), E is $C(O)OR^6$ or $C(O)NR^6R^7$, and $R^1$, $R^2$, $R^3$, $R^5$, $R^6$, $R^7$ and Z' are defined as described herein:

I(a)
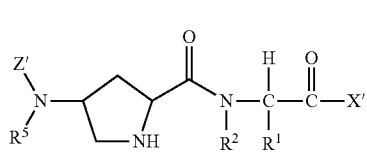

I(b)
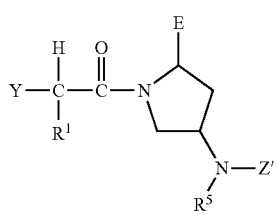

I(c)
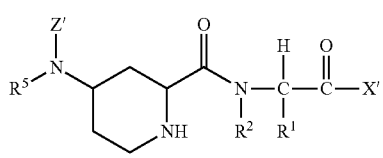

I(d)
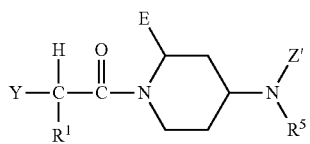

I(e)
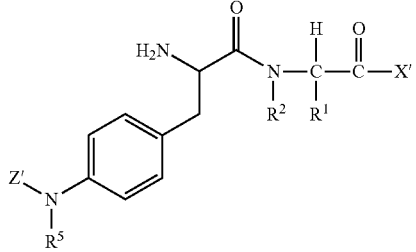

I(f)
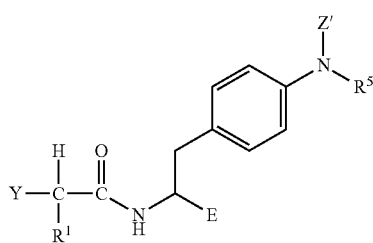

I(g)
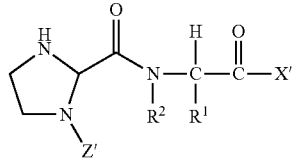

I(h) 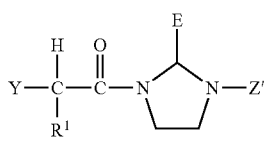
I(i) 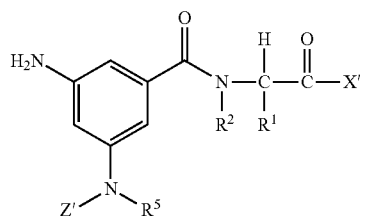
I(j) 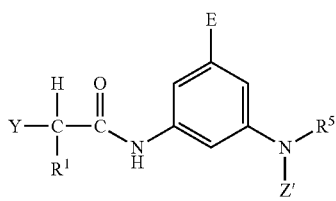
I(k) 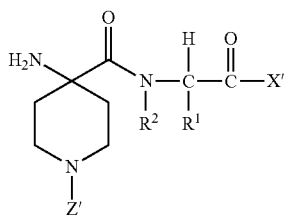
I(l) 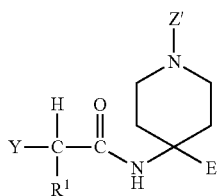
I(m) 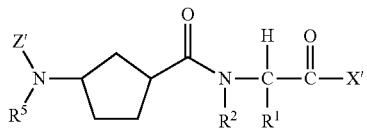
I(n) 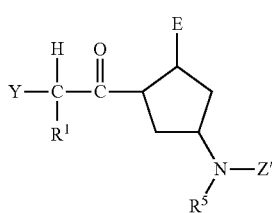
I(o) 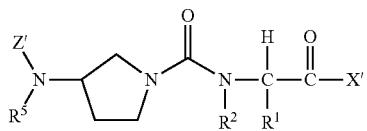
I(p)
Certain compounds of the present teachings have structures represented by Formulae I(q)-I(x) below, wherein $R^1$, $R^2$, E and each $R^5$ and Z' (each of which can be the same or different) are defined as described herein:
I(q)
I(r)
I(s)
I(t)
I(u)

-continued

I(v)
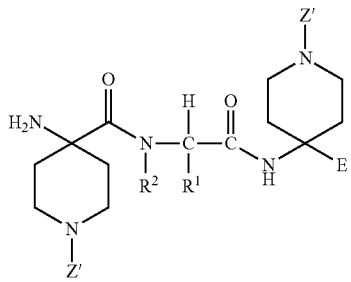

I(w)
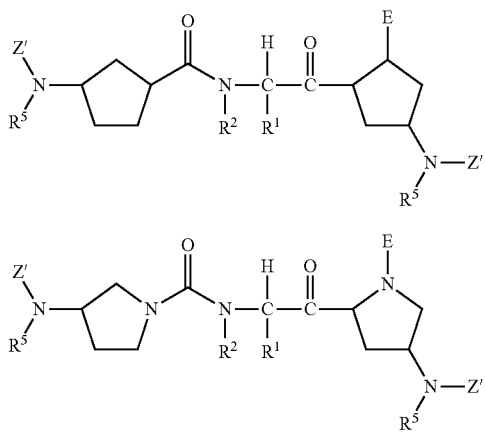

I(x)

In some embodiments, the present teachings provide compounds of Formula I and pharmaceutically acceptable salts, esters, hydrates and prodrugs thereof, wherein X' is OR$^3$ or NR$^2$R$^3$ (e.g., OH or NH$_2$), Y is NXR$^2$, X is

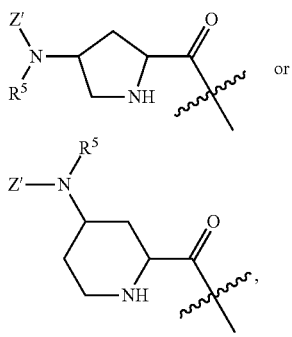

and Z', k, R$^1$, R$^2$, R$^3$ and R$^5$ are defined as described above. In some examples of these compounds, Z' is C(O)(CH$_2$)$_m$—C$_{6-20}$ aryl optionally substituted with 1-5 Q groups, and m is 0 (e.g., Z' can be benzoyl). In some compounds, R$^1$ is H. In others, R$^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, 3-[(4-benzoylamino-pyrrolidine-2-carbonyl)-amino]-propionic acid, {[4-(4-nitro-benzoylamino)-pyrrolidine-2-carbonyl]-amino}acetic acid, {[4-(4-methoxy-benzoylamino)-pyrrolidine-2-carbonyl]-amino}-acetic acid, 2-[(4-benzoylamino-pyrrolidine-2-carbonyl)-amino]-succinamic acid, 2-[(4-benzoylamino-pyrrolidine-2-carbonyl)-amino]-3-phenyl-propionic acid, 2-[(4-benzoylamino-pyrrolidine-2-carbonyl)-amino]-4-methyl-pentanoic acid, 6-amino-2-(4-benzamidopyrrolidine-2-carboxamido)hexanoic acid, [(4-benzoylamino-pyrrolidine-2-carbonyl)-amino]-acetic acid, {[4-benzoylamino-piperidine-2-carbonyl]-amino}-acetic acid, {[4-benzoylamino-piperidine-2-carbonyl]-amino}-propionic acid, and pharmaceutically acceptable salts, esters, hydrates, and prodrugs thereof.

In certain embodiments, the present teachings provide compounds of Formula I and pharmaceutically acceptable salts, esters, hydrates and prodrugs thereof, wherein X' is OR$^3$ or NR$^2$R$^3$ (e.g., OH or NH$_2$), Y is NXR$^2$, X is

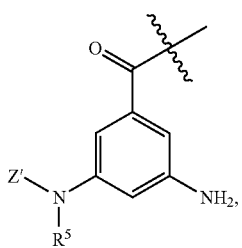

and Z', k, R$^1$, R$^2$, R$^3$ and R$^5$ are defined as described above. In some examples of these compounds, Z' is C(O)(CH$_2$)$_m$—C$_{6-20}$ aryl optionally substituted with 1-5 Q groups, and m is 0 (e.g., Z' can be benzoyl). In some compounds, R$^1$ is H. In others, R$^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, 3-amino-5-benzoylamino-benzoylamino)-acetic acid, (3-amino-5-(4-methoxy-benzoylamino)-benzoylamino)-acetic acid, (3-amino-5-(4-methyl-benzoylamino)-benzoylamino)-acetic acid, (3,5-diamino-benzoylamino)-acetic acid, and pharmaceutically acceptable salts, esters, hydrates, and prodrugs thereof.

In some embodiments, the present teachings provide compounds of Formula I and pharmaceutically acceptable salts, esters, hydrates and prodrugs thereof, wherein X' is OR$^3$ or NR$^2$R$^3$ (e.g., OH or NH$_2$), Y is NXR$^2$, X is

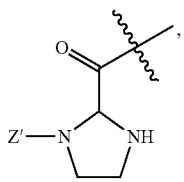

and Z', k, R$^1$, R$^2$ and R$^3$ are defined as described above. In some examples of these compounds, Z' is C(O)(CH$_2$)$_m$—C$_{6-20}$ aryl optionally substituted with 1-5 Q groups, and m is 0 (e.g., Z' can be benzoyl). In some compounds, R$^1$ is H. In others, R$^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, [(1-benzoyl-imidazolidine-2-carbonyl)-amino]acetic acid, {[1-(4-nitro-benzoyl)-imidazolidine-2-carbonyl]-amino}acetic acid, and pharmaceutically acceptable salts, esters, hydrates, and prodrugs thereof.

In certain embodiments, the present teachings provide compounds of Formula I and pharmaceutically acceptable salts, esters, hydrates and prodrugs thereof, wherein X' is OR$^3$ or NR$^2$R$^3$ (e.g., OH or NH$_2$), Y is NXR$^2$, X is

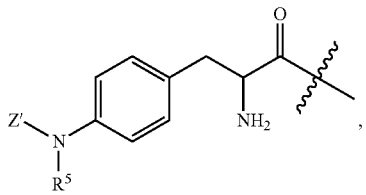

and Z', k, R$^1$, R$^2$, R$^3$ and R$^5$ are defined as described above. In some examples of these compounds, Z' is C(O)(CH$_2$)$_m$—C$_{6-20}$ aryl optionally substituted with 1-5 Q groups, and m is 0 (e.g., Z' can be benzoyl). In some compounds, R$^1$ is H. In others, R$^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, [2-amino-3-(4-benzoylamino-phenyl)-propionylamino]-acetic acid, 2-{2-amino-3-[4-(4-methoxybenzamido)phenyl]propanamido}acetic acid, 2-{2-amino-3-[4-(4-nitrobenzamido)phenyl]propanamido}acetic acid, 2-{2-amino-3-[4-(4-methylbenzamido)phenyl]propanamido}acetic acid, and pharmaceutically acceptable salts, esters, hydrates, and prodrugs thereof.

In some embodiments, the present teachings provide compounds of Formula I and pharmaceutically acceptable salts, esters, hydrates and prodrugs thereof, wherein X' is OR$^3$ or NR$^2$R$^3$ (e.g., OH or NH$_2$), Y is NXR$^2$, X is

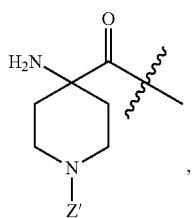

and Z', k, R$^1$, R$^2$ and R$^3$ are defined as described above. In some examples of these compounds, Z' is C(O)(CH$_2$)$_m$—C$_{6-20}$ aryl optionally substituted with 1-5 Q groups, and m is 0 (e.g., Z' can be benzoyl). In some compounds, R$^1$ is H. In others, R$^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, [(4-amino-1-benzoyl-piperidine-4-carbonyl)-amino]-acetic acid and pharmaceutically acceptable salts, esters, hydrates, and prodrugs thereof.

In certain embodiments, the present teachings provide compounds of Formula I and pharmaceutically acceptable salts, esters, hydrates and prodrugs thereof, wherein Y is OR$^2$ or NR$^2$R$^3$, X' is

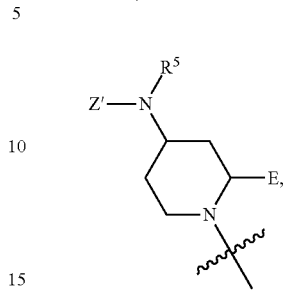

and Z', k, E, R$^1$, R$^2$, R$^3$ and R$^5$ are defined as described above, provided the compound is not 1-(2-aminopropanoyl)-4-benzamidopiperidine-2-carboxylic acid. In some examples of these embodiments, Y is OH or NH$_2$. In some compounds, E is C(O)OR$^6$ (e.g., C(O)OH) or C(O)NR$^6$R$^7$ (e.g., C(O)NHR$^7$ or C(O)NH$_2$). In some compounds, Z' is C(O)(CH$_2$)$_m$—C$_{6-20}$ aryl optionally substituted with 1-5 Q groups, and m is 0 (e.g., Z' is benzoyl). In some compounds, R$^1$ is H. In others, R$^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine (provided the compound is not 1-(2-aminopropanoyl)-4-benzamidopiperidine-2-carboxylic acid). In some compounds, k is 0; in others, k is 1. Specific examples of compounds according to these embodiments of the present teachings include, but are not limited to, 1-(2-amino-4-carboxy-butyryl)-4-benzoylamino-piperidine-2-carboxylic acid, 1-(2-amino-4-methyl-pentanoyl)-4-benzoylamino-piperidine-2-carboxylic acid, 4-benzoylamino-1-(2,6-diamino-hexanoyl)-piperidine-2-carboxylic acid, 1-(2-amino-acetyl)-4-benzoylamino-piperidine-2-carboxylic acid, 1-(3-amino-propionyl)-4-benzoylamino-piperidine-2-carboxylic acid, 1-[2-amino-3-(1H-indol-3-yl)-propionyl]-4-benzoylamino-piperidine-2-carboxylic acid, 1-(2-amino-3-phenyl-propionyl)-4-benzoylamino-piperidine-2-carboxylic acid, 4-benzoylamino-1-(2-hydroxy-acetyl)-piperidine-2-carboxylic acid, and pharmaceutically acceptable salts, esters, hydrates, and prodrugs thereof.

In some embodiments, the present teachings provide compounds of Formula I and pharmaceutically acceptable salts, esters, hydrates and prodrugs thereof, wherein Y is OR$^2$ or NR$^2$R$^3$, X' is

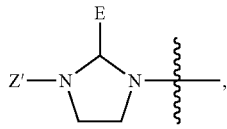

and Z', k, E, R$^1$, R$^2$ and R$^3$ are defined as described above. In some examples of these embodiments, Y is OH or NH$_2$. In some compounds, E is C(O)OR$^6$ (e.g., C(O)OH) or C(O)NR$^6$R$^7$ (e.g., C(O)NHR$^7$ or C(O)NH$_2$). In some compounds, Z' is C(O)(CH$_2$)$_m$—C$_{6-20}$ aryl optionally substituted with 1-5 Q groups, and m is 0 (e.g., Z' is benzoyl). In some compounds, R$^1$ is H. In others, R$^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, 1-(2-amino-4-carboxy-butyroyl)-3-benzoyl-imidazolidine-2-carboxylic acid, 1-benzoyl-3-(2-hydroxy-acetyl)-imidazolidine-2-carboxylic acid amide, 1-benzoyl-3-(2-hydroxy-acetyl)-imidazolidine-2-carboxylic acid, and pharmaceutically acceptable salts, esters, hydrates, and prodrugs thereof.

In certain embodiments, the present teachings provide compounds of Formula I and pharmaceutically acceptable salts, esters, hydrates and prodrugs thereof, wherein Y is $OR^2$ or $NR^2R^3$, X' is

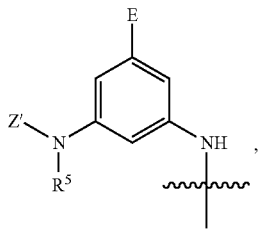

and Z', k, E, $R^1$, $R^2$, $R^3$ and $R^5$ are defined as described above. In some examples of these embodiments, Y is OH or $NH_2$. In some compounds, E is $C(O)OR^6$ (e.g., C(O)OH) or $C(O)NR^6R^7$ (e.g., $C(O)NHR^7$ or $C(O)NH_2$). In some compounds, Z' is $C(O)(CH_2)_m$—$C_{6-20}$ aryl optionally substituted with 1-5 Q groups, and m is 0 (e.g., Z' is benzoyl). In some compounds, $R^1$ is H. In others, $R^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, 3-benzoylamino-5-(2-hydroxy-acetylamido)-benzoic acid, 3-(2-aminoacetamido)-5-benzamidobenzoic acid, 3-(2-aminoacetamido)-5-(4-methylbenzamido)benzoic acid, 3-(2-amino-3-carbamoyl-propionylamino)-5-benzoylamino-benzoic acid, and pharmaceutically acceptable salts, esters, hydrates, and prodrugs thereof.

In certain embodiments, the present teachings provide compounds of Formula I and pharmaceutically acceptable salts, esters, hydrates and prodrugs thereof, wherein Y is $OR^2$ or $NR^2R^3$, X' is

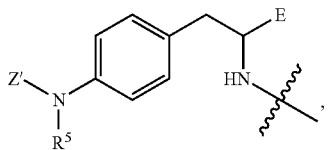

and Z', k, E, $R^1$, $R^2$, $R^3$ and $R^5$ are defined as described above. In some examples of these embodiments, Y is OH or $NH_2$. In some compounds, E is $C(O)OR^6$ (e.g., C(O)OH) or $C(O)NR^6R^7$ (e.g., $C(O)NHR^7$ or $C(O)NH_2$). In some compounds, Z' is $C(O)(CH_2)_m$—$C_{6-20}$ aryl optionally substituted with 1-5 Q groups, and m is 0 (e.g., Z' is benzoyl). In some compounds, $R^1$ is H. In others, $R^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, 3-(4-benzoylamino-phenyl)-2-(2-hydroxy-acetylamido)-propionic acid, N-{4-[2-carbamoyl-2-(2-hydroxy-acetamido)-ethyl]-phenyl}-benzamide, and pharmaceutically acceptable salts, esters, hydrates, and prodrugs thereof.

In some embodiments, the present teachings provide compounds of Formula I and pharmaceutically acceptable salts, esters, hydrates and prodrugs thereof, wherein Y is $OR^2$ or $NR^2R^3$, X' is

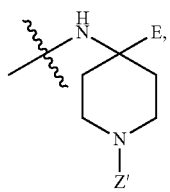

and Z', k, E, $R^1$, $R^2$ and $R^3$ are defined as described above. In some examples of these embodiments, Y is OH or $NH_2$. In some compounds, E is $C(O)OR^6$ (e.g., C(O)OH) or $C(O)NR^6R^7$ (e.g., $C(O)NHR^7$ or $C(O)NH_2$). In some compounds, Z' is $C(O)(CH_2)_m$—$C_{6-20}$ aryl optionally substituted with 1-5 Q groups, and m is 0 (e.g., Z' is benzoyl). In some compounds, $R^1$ is H. In others, $R^1$ is an amino acid side chain, wherein the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine. In some compounds, k is 0; in others, k is 1. Specific examples of compounds according to these embodiments of the present teachings include, but are not limited to, 4-benzoylamino-1-(2-hydroxy-acetylamido)-cyclohexanecarboxylic acid, 4-(2-aminoacetamido)-1-benzoylpiperidine-4-carboxylic acid, and pharmaceutically acceptable salts, esters, hydrates, and prodrugs thereof.

The present teachings include all stereoisomers of the compounds described herein. For example, the stereochemistry of dipeptide embodiments of the present teachings can be 2R4R, 2R4S, 2S4S, or 2S4R.

In another aspect, the present teachings provide compounds having the Formula II:

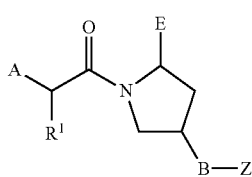

and pharmaceutically acceptable salts, esters, hydrates and prodrugs thereof, wherein:
  A is $(CH_2)_k$—Y';
  k is 0, 1, or 2;
  Y' is $OR^2$ or $NR^2R^3$;
  $R^1$ is selected from H, an optionally substituted $C_{1-10}$ alkyl, an optionally substituted $C_{6-20}$ aryl, an optionally substituted $C_{7-20}$ aralkyl, and an amino acid side chain;

alternatively, A and $R^1$ together with the carbon atom to which they are bound form a 5-20 membered heteroaryl containing 1-4 ring heteroatoms independently selected from N, O, and S and optionally substituted with 1-5 Q groups;

B is selected from $NR^5$, $NR^5(CH_2)_nC(O)$, $NR^5(CH_2)_nS(O)_2$, and an amide bioisostere;

n is 0, 1, or 2;

Z is selected from H, $(CH_2)_n$—$C_{6-20}$ aryl optionally substituted with 1-5 Q groups, and $(CH_2)_m$-5-20 membered heteroaryl optionally substituted with 1-5 Q groups;

m is 0, 1, or 2;

E is selected from $C(O)OR^6$, $C(O)NR^6R^7$, a carboxylic acid bioisostere and an amide bioisostere;

Q, at each occurrence, independently is selected from an optionally substituted $C_{1-10}$ alkyl, an optionally substituted $C_{2-10}$ alkenyl, an optionally substituted $C_{2-10}$ alkynyl, an optionally substituted $C_{3-20}$ cycloalkyl, an optionally substituted $C_{6-20}$ aryl, an optionally substituted $C_{7-20}$ aralkyl, an optionally substituted 3-20 membered cycloheteroalkyl, an optionally substituted 5-20 membered heteroaryl, F, Cl, Br, I, CN, $CF_3$, $OCF_3$, $NO_2$, $OR^8$, $SR^8$, $S^+R^8_2$, $S(O)R^8$, $S(O)_2R^8$, $S(O)_2OH$, $S(O)_2NR^8R^9$, $NR^8S(O)_2R^9$, $C(O)R^8$, $C(O)OR^8$, $C(O)NR^8R^9$, $OC(O)R^8$, $NR^8R^9$, $NR^8C(O)R^9$, $NR^8C(O)OR^9$, $NR^8C(O)NR^8R^9$, and $N^+R^8_3$;

$R^2$ and $R^3$ each independently is selected from H, an optionally substituted $C_{1-10}$ alkyl, an optionally substituted $C_{3-20}$ cycloalkyl, an optionally substituted $C_{7-20}$ aralkyl, an optionally substituted $C_{6-20}$ aryl, an optionally substituted 3-20 membered cycloheteroalkyl, an optionally substituted 5-20 membered heteroaryl, $C(O)R^6$, $C(O)OR^6$, $C(O)NR^6R^7$, $S(O)_2R^6$, and $S(O)_2NR^6R^7$;

alternatively, $R^2$ and $R^3$ together with the nitrogen atom to which they are bound form a 3-20 membered heterocycle optionally containing 1-4 ring heteroatoms independently selected from O, N and S atoms and optionally substituted with 1-5 Q groups;

$R^5$ is H or an optionally substituted $C_{1-10}$ alkyl;

$R^6$ and $R^7$ each independently is selected from H, an optionally substituted $C_{1-10}$ alkyl, an optionally substituted $C_{3-20}$ cycloalkyl, an optionally substituted $C_{2-10}$ alkenyl, an optionally substituted $C_{2-10}$ alkynyl, an optionally substituted $C_{6-20}$ aryl, an optionally substituted $C_{7-20}$ aralkyl, an optionally substituted 3-20 membered cycloheteroalkyl, an optionally substituted 5-20 membered heteroaryl, $C(O)R^8$, $C(O)OR^8$, and $C(O)NR^8R^9$;

alternatively, $R^6$ and $R^7$ together with the nitrogen atom to which they are bound form a 3-20 membered heterocycle optionally containing 1-4 ring heteroatoms independently selected from O, N and S and optionally substituted with 1-5 Q groups; and $R^8$ and $R^9$ each independently is selected from H, an optionally substituted $C_{1-10}$ alkyl, an optionally substituted $C_{3-20}$ cycloalkyl, an optionally substituted $C_{2-10}$ alkenyl, an optionally substituted $C_{2-10}$alkynyl, an optionally substituted $C_{6-20}$ aryl, an optionally substituted $C_{7-20}$ aralkyl, an optionally substituted 3-20 membered cycloheteroalkyl, and an optionally substituted 5-20 membered heteroaryl, provided that the compound is not 1-(2-aminopropanoyl)-4-benzamidopyrrolidine-2-carboxylic acid.

In some embodiments, A is $(CH_2)_k$—Y' and Y' is $NR^2R^3$. Examples of these embodiments include compounds wherein $R^2$ is H and $R^3$ is selected from H (i.e., Y' is $NH_2$), an optionally substituted $C_{1-10}$alkyl, $C(O)R^6$, and $C(O)OR^6$. In some examples, A is $(CH_2)_k$—Y', Y' is $NR^2R^3$, $R^2$ is H, $R^3$ is $C(O)R^6$ and $R^6$ is H or an optionally substituted $C_{1-10}$alkyl. In other examples, A is $(CH_2)_k$—Y', Y' is $NR^2R^3$ and $R^2$ and $R^3$ each independently is an optionally substituted $C_{1-10}$ alkyl. In other embodiments, Y' is $OR^2$ and $R^2$ is H or a $C_{1-10}$ alkyl. In any of these examples, k can be 0, 1 or 2.

In certain embodiments, A and $R^1$ together with the carbon atom to which they are bound form a 5-20 membered heterocycle containing 1-4 ring heteroatoms independently selected from N, O, and S and optionally substituted with 1-5 Q groups. Examples of heterocycle groups can include, but are not limited to, piperidine, piperazine, morpholine, thiomorpholine, pyrrolidine, oxazolidine, thiazolidine, imidazolidine, pyrrole, imidazole, pyrazole, triazole, tetrazole, furan, thiofuran, oxazole, isoxazole, thiazole, isothiazole, oxadiazole, thiadiazole, pyridine, pyridazine, pyrimidine, pyrazine, indole, benzofuran, and benzothiophene, each of which optionally can be substituted. Exemplary compounds of these embodiments include, but are not limited to, 4-benzamido-1-(1H-imidazole-2-carbonyl)pyrrolidine-2-carboxylic acid, 4-benzamido-1-(1H-pyrazole-5-carbonyl)pyrrolidine-2-carboxylic acid, and 4-benzamido-1-(1H-imidazole-5-carbonyl)pyrrolidine-2-carboxylic acid.

In some embodiments, B is $NR^5(CH_2)_nC(O)$, n is 0 (i.e., B is $NR^5C(O)$), and Z is a $C_{6-20}$ aryl optionally substituted with 1-5 Q groups or a 5-20 membered heteroaryl optionally substituted with 1-5 Q groups. Examples of these embodiments include compounds wherein $R^5$ is H (i.e., B is NHC(O)). In some compounds, Z is a phenyl optionally substituted with 1-5 Q groups, such as, for example, F, Cl, Br, I, $C_{1-10}$ alkyl, $CF_3$, $OCF_3$, $NO_2$, O—$C_{1-10}$ alkyl, OH, $NH_2$, $NH(C_{1-10}$ alkyl), $N(C_{1-10}$ alkyl$)_2$, or $NHC(O)C_{1-13}$ alkyl. In certain embodiments B—Z is NHC(O)-phenyl. In some embodiments, Z is $(CH_2)_m$-5-20 membered heteroaryl optionally substituted with 1-5 Q groups. In certain embodiments, m is 0. Exemplary compounds of these embodiments include, but are not limited to, 1-(2-aminoacetyl)-4-(picolinamido)pyrrolidine-2-carboxylic acid, 1-(2-aminoacetyl)-4-(nicotinamido)pyrrolidine-2-carboxylic acid, 1-(2-aminoacetyl)-4-(isonicotinamido)pyrrolidine-2-carboxylic acid, 1-(2-aminoacetyl)-4-(pyrimidine-5-carboxamido)pyrrolidine-2-carboxylic acid, 1-(2-aminoacetyl)-4-(2-fluorobenzamido)pyrrolidine-2-carboxylic acid, 1-(2-aminoacetyl)-4-(3-fluorobenzamido)pyrrolidine-2-carboxylic acid, 1-(2-aminoacetyl)-4-(4-fluorobenzamido)pyrrolidine-2-carboxylic acid, 1-(2-aminoacetyl)-4-(2-methylbenzamido)pyrrolidine-2-carboxylic acid, 1-(2-aminoacetyl)-4-(3-methylbenzamido)pyrrolidine-2-carboxylic acid, 1-(2-aminoacetyl)-4-(4-methylbenzamido)pyrrolidine-2-carboxylic acid 1-(2-aminoacetyl)-4-(4-methoxybenzamido)pyrrolidine-2-carboxylic acid, 1-(2-aminoacetyl)-4-(3-methoxybenzamido)pyrrolidine-2-carboxylic acid, 1-(2-aminoacetyl)-4-(4-hydroxybenzamido)pyrrolidine-2-carboxylic acid, and 1-(2-aminoacetyl)-4-(3-hydroxybenzamido)pyrrolidine-2-carboxylic acid.

In some embodiments, B is $NR^5(CH_2)_nC(O)$, n is 0 (i.e., B is $NR^5C(O)$) and Z is $(CH_2)_mC_{6-20}$ aryl optionally substituted with 1-5 Q groups or $(CH_2)_m$-5-20 membered heteroaryl optionally substituted with 1-5 Q groups, wherein m is 1 or 2. A non-limiting example of these embodiments is 1-(2-aminoacetyl)-4-(2-phenylacetamido)pyrrolidine-2-carboxylic acid. In other embodiments, B is $NR^5(CH_2)_nC(O)$ wherein n is 1 or 2. A non-limiting example of these embodiments is 1-(2-aminoacetyl)-4-(2-oxo-2-phenylethylamino)pyrrolidine-2-carboxylic acid).

In other embodiments, B is $NR^5$, $R^5$ is H, Z is $(CH_2)_mC_{6-20}$ aryl optionally substituted with 1-5 Q groups or $(CH_2)_m$-5-20 membered heteroaryl optionally substituted with 1-5 Q groups, and m is 0 (e.g., 1-(2-aminoacetyl)-4-(phenylamino)pyrrolidine-2-carboxylic acid) or 1 (e.g., 1-(2-aminoacetyl)-4-(benzylamino)pyrrolidine-2-carboxylic acid). In still other embodiments, B is $NR^5(CH_2)_nS(O)_2$, n is 0 (i.e., B is $NR^5S(O)_2$) and Z is $(CH_2)_m$—$C_{6-20}$ aryl optionally substituted with 1-5 Q groups or $(CH_2)_m$-5-20 membered heteroaryl optionally substituted with 1-5 Q groups. One non-limiting example of these embodiments is 1-(2-aminoacetyl)-4-(phenylsulfonamido) pyrrolidine-2-carboxylic acid).

In still other embodiments, B is an amide bioisostere, such as, for example, imidazole, oxazole, thiazole, pyrazole, triazole, oxadiazole, thiadiazole, or tetrazole, each of which optionally can be substituted. Exemplary compounds of these embodiments include, but are not limited to, 1-(2-aminoacetyl)-4-(4-phenyloxazol-2-yl)pyrrolidine-2-carboxylic acid, 1-(2-aminoacetyl)-4-(5-phenyloxazol-2-yl)pyrrolidine-2-carboxylic acid, 1-(2-aminoacetyl)-4-(5-phenyl-1H-imidazol-2-yl)pyrrolidine-2-carboxylic acid, and 1-(2-aminoacetyl)-4-(4-phenyl-1H-imidazol-2-yl)pyrrolidine-2-carboxylic acid.

In some embodiments, E is $C(O)OR^6$. Examples include compounds wherein E is C(O)OH. In other embodiments, E is $C(O)NR^6R^7$. In some compounds, E is $C(O)NH_2$. In other compounds, E is $C(O)NR^6R^7$, $R^6$ is H, and $R^7$ is selected from an optionally substituted $C_{1-10}$ alkyl, an optionally substituted $C_{3-20}$ cycloalkyl, an optionally substituted $C_{6-20}$ aryl, an optionally substituted 3-20 membered cycloheteroalkyl, and an optionally substituted 5-20 membered heteroaryl.

In other embodiments, E is a carboxylic acid bioisostere such as, for example, imidazole, oxazole, thiazole, pyrazole, triazole, oxadiazole, thiadiazole, or tetrazole, each of which optionally can be substituted. Exemplary compounds of these embodiments include, but are not limited to, N-[1-(2-aminoacetyl)-5-(1H-tetrazol-5-yl)pyrrolidin-3-yl]benzamide, N-[1-(2-aminoacetyl)-5-(1H-imidazol-2-yl)pyrrolidin-3-yl]benzamide, N-[1-(2-aminoacetyl)-5-(5-methyl-1H-imidazol-2-yl)pyrrolidin-3-yl]benzamide, N-[1-(2-aminoacetyl)-5-(5-isopropyl-1H-imidazol-2-yl)pyrrolidin-3-yl]benzamide, N-[1-(2-aminoacetyl)-5-(oxazol-2-yl)pyrrolidin-3-yl]benzamide, N-[1-(2-aminoacetyl)-5-(5-isopropyloxazol-2-yl)pyrrolidin-3-yl]benzamide, N-[1-(2-aminoacetyl)-5-(5-methyloxazol-2-yl)pyrrolidin-3-yl]benzamide, N-[1-(2-aminoacetyl)-5-(4-methyloxazol-2-yl)pyrrolidin-3-yl]benzamide, N-[1-(2-aminoacetyl)-5-(1H-pyrazol-5-yl)pyrrolidin-3-yl]benzamide, N-[1-(2-aminoacetyl)-5-(3-isopropyl-1H-pyrazol-5-yl)pyrrolidin-3-yl]benzamide, N-[1-(2-aminoacetyl)-5-(3-methyl-1H-pyrazol-5-yl)pyrrolidin-3-yl]benzamide, N-[1-(2-aminoacetyl)-5-(1H-1,2,4-triazol-5-yl)pyrrolidin-3-yl]benzamide, N-[1-(2-aminoacetyl)-5-(3-methyl-1H-1,2,4-triazol-5-yl)pyrrolidin-3-yl]benzamide, N-[1-(2-aminoacetyl)-5-(3-isopropyl-1H-1,2,4-triazol-5-yl)pyrrolidin-3-yl]benzamide, N-[1-(2-aminoacetyl)-5-(1,3,4-oxadiazol-2-yl)pyrrolidin-3-yl]benzamide, and N-[1-(2-aminoacetyl)-5-(5-methyl-1,3,4-oxadiazol-2-yl)pyrrolidin-3-yl]benzamide.

In some embodiments, when A is $(CH_2)_k$—Y', Y' is $NH_2$, k is 0, E is C(O)OH, B is NHC(O), and Z is phenyl, then $R^1$ is not methyl. In other embodiments, when A is $(CH_2)_k$—Y', Y' is $NH_2$, k is 0, $R^1$ is methyl, E is C(O)OH, and Z' is phenyl, then the phenyl is substituted with at least one Q group. In still other embodiments, when A is $(CH_2)_k$—Y', Y' is $NH_2$, k is 0, $R^1$ is methyl, B is NHC(O), and Z is phenyl, then E is not C(O)OH. In other embodiments, when A is $(CH_2)_k$—Y', Y' is $NH_2$, $R^1$ is methyl, E is C(O)OH, B is NHC(O), and Z' is phenyl, then k is 1 or 2. In yet other embodiments, when A is $(CH_2)_k$—Y', k is 0, $R^1$ is methyl, E is C(O)OH, B is NHC(O), and Z' is phenyl, then Y' is not $NH_2$.

Compounds according to the present teachings include those having the following structures:

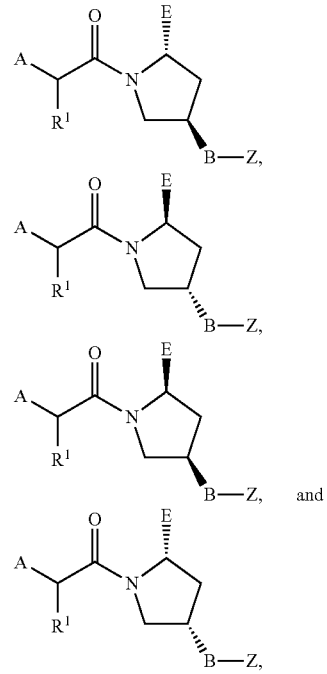

and pharmaceutically acceptable salts, esters, hydrates, and prodrugs thereof.

In another aspect, the present teachings provide compounds having the Formula III:

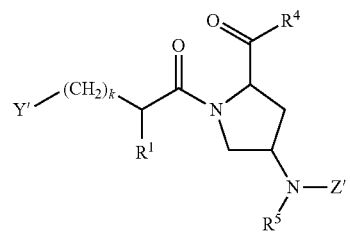

and pharmaceutically acceptable salts, esters, hydrates, and prodrugs thereof, wherein:

Y' is $OR^2$ or $NR^2R^3$;

k is 0, 1, or 2;

Z' is selected from H, $(CH_2)_m$—$C_{6-20}$ aryl, $(CH_2)_m$-5-20 membered heteroaryl, $C(O)(CH_2)_m$—$C_{6-20}$ aryl, $C(O)(CH_2)_m$-5-20 membered heteroaryl, $(CH_2)_mC(O)$—$C_{6-20}$ aryl, $(CH_2)_mC(O)$-5-20 membered heteroaryl, $S(O)_2(CH_2)_m$—$C_{6-20}$ aryl, and $S(O)_2(CH_2)_m$-5-20 membered heteroaryl, wherein each of the $C_{6-20}$ aryl and 5-20 membered heteroaryl is optionally substituted with 1-5 Q groups;

m is 0, 1, or 2;

Q, at each occurrence, independently is selected from an optionally substituted $C_{1-10}$ alkyl, an optionally substituted $C_{2-10}$ alkenyl, an optionally substituted $C_{2-10}$ alkynyl, an optionally substituted $C_{3-20}$ cycloalkyl, an optionally substituted $C_{6-20}$ aryl, an optionally substituted $C_{7-20}$ aralkyl, an optionally substituted 3-20 membered cycloheteroalkyl, an optionally substituted 5-20 membered heteroaryl, F, Cl, Br, I, CN, $CF_3$, $OCF_3$, $NO_2$, $OR^8$, $SR^8$, $S^+R^8{}_2$, $S(O)R^8$, $S(O)_2R^8$, $S(O)_2OH$, $S(O)_2NR^8R^9$, $NR^8S(O)_2R^9$, $C(O)R^8$, $C(O)OR^8$, $C(O)NR^8R^9$, $OC(O)R^8$, $NR^8R^9$, $NR^8C(O)R^9$, $NR^8C(O)OR^9$, $NR^8C(O)NR^8R^9$, and $N^+R^8{}_3$;

$R^1$ is selected from H, an optionally substituted $C_{1-10}$ alkyl, an optionally substituted $C_{6-20}$ aryl, an optionally substituted $C_{7-20}$ aralkyl, and an amino acid side chain;

$R^2$ and $R^3$ each independently is selected from H, an optionally substituted $C_{1-10}$ alkyl, an optionally substituted $C_{3-20}$ cycloalkyl, an optionally substituted $C_{7-20}$ aralkyl, an optionally substituted $C_{6-20}$ aryl, an optionally substituted 3-20 membered cycloheteroalkyl, an optionally substituted 5-20 membered heteroaryl, $C(O)R^6$, $C(O)OR^6$, $C(O)NR^6R^7$, $S(O)_2R^6$, and $S(O)_2NR^6R^7$;

alternatively, $R^2$ and $R^3$ together with the nitrogen atom to which they are bound form a 3-20 membered heterocycle optionally containing 1-4 ring heteroatoms independently selected from O, N or S and optionally substituted with 1-5 Q groups;

$R^4$ is $OR^6$ or $NR^6R^7$;

$R^5$ is H or an optionally substituted $C_{1-10}$ alkyl;

$R^6$ and $R^7$ each independently is selected from H, an optionally substituted $C_{1-10}$ alkyl, an optionally substituted $C_{3-20}$ cycloalkyl, an optionally substituted $C_{2-10}$ alkenyl, an optionally substituted $C_{2-10}$ alkynyl, an optionally substituted $C_{6-20}$ aryl, an optionally substituted $C_{7-20}$ aralkyl, an optionally substituted 3-20 membered cycloheteroalkyl, an optionally substituted 5-20 membered heteroaryl, $C(O)R^8$, $C(O)OR^8$, and $C(O)NR^8R^9$;

alternatively, $R^6$ and $R^7$ together with the nitrogen atom to which they are bound form a 3-20 membered heterocycle optionally containing 1-4 ring heteroatoms independently selected from O, N or S and optionally substituted with 1-5 Q groups; and $R^8$ and $R^9$ each independently is selected from H, an optionally substituted $C_{1-10}$ alkyl, an optionally substituted $C_{3-20}$ cycloalkyl, an optionally substituted $C_{2-10}$ alkenyl, an optionally substituted $C_{2-10}$ alkynyl, an optionally substituted $C_{6-20}$ aryl, an optionally substituted $C_{7-20}$ aralkyl, an optionally substituted 3-20 membered cycloheteroalkyl, and an optionally substituted 5-20 membered heteroaryl;

provided that the compound is not 1-(2-aminopropanoyl)-4-benzamidopyrrolidine-2-carboxylic acid.

In some embodiments k is 0; in others, k is 1.

In some embodiments, Y' is $NR^2R^3$ and $R^2$ is H (i.e., Y' is $NHR^3$) and $R^3$ is selected from H (i.e., Y' is $NH_2$), an optionally substituted $C_{1-10}$ alkyl, $C(O)R^6$, or $C(O)OR^6$. In some embodiments, Y' is $NR^2R^3$, $R^2$ is H, $R^3$ is $C(O)R^6$ and $R^6$ is H (i.e., $R^3$ is $C(O)H$) or an optionally substituted $C_{1-10}$ alkyl (e.g., $R^3$ is $C(O)CH_3$). In other embodiments, Y' is $NR^2R^3$; and $R^2$ and $R^3$ each independently is an optionally substituted $C_{1-10}$ alkyl. In still other embodiments, Y' is $OR^2$ and $R^2$ is H (i.e., Y is OH) or an optionally substituted $C_{1-10}$ alkyl.

In certain embodiments, $R^1$ is H. In other embodiments, $R^1$ is an amino acid side chain and the amino acid is selected from valine, leucine, isoleucine, methionine, alanine, phenylalanine, tyrosine, tryptophan, serine, threonine, cysteine, lysine, argenine, histidine, aspartic acid, glutamic acid, asparagine and glutamine, provided that the compound is not 1-(2-aminopropanoyl)-4-benzamidopyrrolidine-2-carboxylic acid.

Other embodiments of the present teachings include compounds wherein $R^4$ is $OR^6$ (e.g., OH). Alternatively, $R^4$ can be $NR^6R^7$, wherein $R^6$ is H and $R^7$ is selected from H (i.e., $R^4$ is $NH_2$), an optionally substituted $C_{1-10}$ alkyl, an optionally substituted $C_{3-20}$ cycloalkyl, an optionally substituted $C_{6-20}$ aryl, an optionally substituted 3-20 membered cycloheteroalkyl, or an optionally substituted 5-20 membered heteroaryl. In still other alternatives, $R^6$ and $R^7$ together with the nitrogen atom to which they are bound form a 3-20 membered heterocycle selected from piperidine, piperazine, morpholine, thiomorpholine, pyrrolidine, oxazolidine, thiazolidine, and imidazolidine, each of which optionally can be substituted with 1-5 Q groups.

In some embodiments, Z' is $C(O)(CH_2)_m$—$C_{6-20}$ aryl optionally substituted with 1-5 Q groups and m is 0 (i.e., Z is $C(O)$—$C_{6-20}$ aryl optionally substituted with 1-5 Q groups). Exemplary compounds of these embodiments include those wherein Z' is benzoyl. In other examples, Z is benzoyl substituted with 1-5 Q groups, such as, for example, F, Cl, Br, I, $C_{1-10}$ alkyl, $CF_3$, $OCF_3$, $NO_2$, O—$C_{1-10}$ alkyl, OH, $NH_2$, $NH(C_{1-10}$ alkyl), $N(C_{1-10}$ alkyl$)_2$, and $NHC(O)C_{1-10}$ alkyl.

In some embodiments, when Y' is $NH_2$, k is 0, $R^4$ is OH, $R^5$ is H, and Z' is benzoyl, then $R^1$ is not methyl. In other embodiments, when Y' is $NH_2$, k is 0, $R^1$ is methyl, $R^4$ is OH, $R^5$ is H, and Z' is benzoyl, then the benzoyl is substituted with at least one Q group. In still other embodiments, when Y' is $NH_2$, k is 0, $R^1$ is methyl, $R^5$ is H, and Z is benzoyl, then $R^4$ is not OH. In other embodiments, when Y' is $NH_2$, $R^1$ is met$R^4$ is OH, $R^5$ is H, and Z' is benzoyl, then k is 1 or 2. In yet other embodiments, when k is O, $R^1$ is methyl, $R^4$ is OH, $R^5$ is H, and Z' is benzoyl, then Y' is not $NH_2$.

Compounds according to the present teachings include those having the following structures:

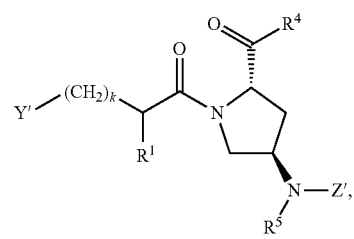

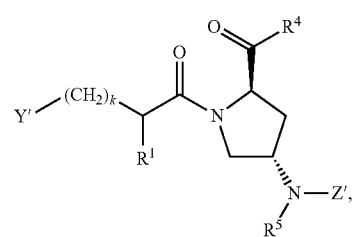

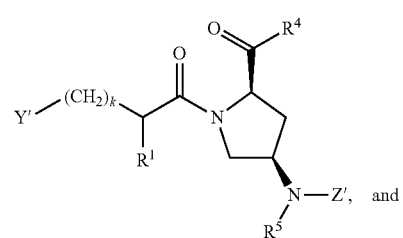

and

-continued

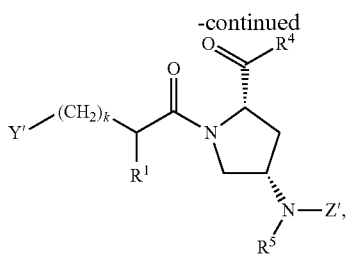

and pharmaceutically acceptable salts, esters, hydrates, and prodrugs thereof.

Examples of suitable prodrugs of any of the compounds of the present teachings include, but are not limited to, oxazolidinone or imidazolidinone prodrugs.

In another aspect, the present teachings provide pharmaceutical compositions comprising a compound according to the present teachings and a pharmaceutically acceptable carrier.

In still another aspect, the present teachings provide methods of preventing or treating a pathological condition comprising administering to a subject in need thereof (e.g., a human being) a therapeutically effective amount of a compound or pharmaceutical composition according to the present teachings. Examples of pathological conditions that can be treated or prevented using compounds of the present teachings include, but are not limited to, cardiovascular disease (e.g., atrial fibrillation, atrial flutter, ventricular tachycardia or ventricular fibrillation); osteoporosis; inflammation of airway epithelium; disorders of alveolar tissue; bladder incontinence; impaired hearing, such as due to diseases of the cochlea; endothelial lesions; diabetes including diabetic retinopathy and diabetic neuropathy; CNS related conditions; ischemia (e.g. ischemia of the central nervous system, spinal cord, brain or brain stem); dental tissue disorders including periodontal disease; kidney diseases; haematologic manifestations (e.g., anaemia, leukopenia, thrombocytopenia, and pancytopenia) especially following treatment with cytostatic compounds or irradiation therapy; wounds such as superficial wounds and deep wounds resulting from trauma; erectile dysfunction; urinary bladder incontinence; neuropathic pain; subchronic and chronic inflammation; cancer; failure of bone marrow and stem cell transplantation; conditions which arise during transplantation of cells and tissues or during medical procedures such as surgery; conditions caused by an excess of reactive oxygen species, free radicals or nitric oxide; diseases or disorders of pregnancy (e.g., preeclampsia and preterm labor); and stroke.

The compounds and pharmaceutical compositions according to the present teachings can be formulated for parenteral or oral administration.

A. Definitions

Unless specified otherwise, the following definitions are provided for specific terms, which are used in the following written description.

Throughout the description and claims the three-letter code for natural amino acids is used as well as generally accepted three letter codes for other α-amino acids, such as sarcosine (Sar). Where the L or D form has not been specified, it is to be understood that the amino acid in question can be either the L or D form. A mixture of equimolar amounts of D and L compounds is termed racemic and is designated by the prefix DL, e.g., DL-leucine. It can alternatively be designated by the prefix rac- (e.g. rac-leucine) or by the prefix [+/−]. The present teachings include all possible stereoisomers of the compounds of Formulae I, II and III as well as of the specific compounds shown herein.

The term "peptide" herein designates a chain of two or more molecules that are linked by means of a peptide bond. Peptides can contain one or more naturally occurring amino acids, one or more unnatural amino acids, one or more molecules that are not amino acids but are capable of forming peptide bonds, or mixtures thereof.

The term "amino acid" refers to a molecule having the general formula NHR—CHR'—COOH (wherein R is H and R' is an amino acid side chain, or R and R' together with the carbon and nitrogen to which they are bonded form a ring, e.g., proline) which is capable of forming a peptide bond with one or more other molecules having the same general formula. The term embraces both L and D amino acids.

A "naturally occurring amino acid" refers to one of the following 20 amino acids: Ala (A), Cys (C), Ser (S), Thr (T), Asp (D), Glu (E), Asn (N), Gln (Q), His (H), Arg (R), Lys (K), Ile (I), Leu (L), Met (M), Val (V), Phe (F), Tyr (Y), Trp (W), Gly (G), and Pro (P). Normally these are L-amino acids, but the present teachings also allow for the use of D-amino acids.

As used herein, the term "lysine mimetic" refers to an unnatural amino acid comprising a $C_{5-6}$ aliphatic or aromatic ring and at least two basic amine functionalities (i.e., at least one basic amine functionality in addition to the N-terminal amine). In some cases, the lysine mimetic has the formula NHR—CHR'—COOH, wherein R and R' together with the carbon and nitrogen to which they are bonded form a 5-6 membered ring, wherein the ring either (a) contains at least one additional ring nitrogen, e.g., imidazolidine-2-carboxylic acid (Ica), or (b) bears an amine substituent, e.g., aminopyrrolidine-2-carboxylic acid (4 Amp) or amino-piperidine-2-carboxylic acid (4 Ampi). In other cases, the lysine mimetic has the formula NHR—CHR'—COOH wherein R is H and R' is a side chain comprising a $C_{5-6}$ aliphatic or aromatic ring, wherein (a) the ring either contains at least one ring nitrogen or bears an amine substituent, and (b) the ring is separated from the amino acid backbone methylene by 1 or 2 atoms. A non-limiting example of such a lysine mimetic is aminophenylalanine (4AmF), wherein 1 atom separates the ring from the backbone. Lysine mimetics can also have the formula NHR—CR'R"—COOH wherein R is H and R' and R" together form a $C_{5-6}$ aliphatic or aromatic ring, wherein the ring either contains at least one ring nitrogen or bears an amine substituent. One non-limiting example of this type of lysine mimetic is 4-amino-piperidine-4-carboxylic acid (Pip). Also included within the definition of "lysine mimetic" are unnatural β- and γ-amino acids comprising a $C_{5-6}$ aliphatic or aromatic ring and at least two basic amine functionalities as described above, such as 3,5-diamino-benzoic acid (Damba). Other lysine mimetics are 4-aminoproline analogs wherein the proline ring nitrogen is not present (e.g., 3-aminocyclopentanecarboxylic acid) or is located in another position in the proline ring (e.g., 3-aminopyrrolidine-1-carboxylic acid or 3-aminopyrrolidine-1-carboxamide). In any of the lysine mimetics, the basic amine functionalities can be a primary amino group (e.g. 4AmF, Damba, 4 Ampi, and 4 Amp) or a secondary amino group (e.g. Pip and Ica). Examples of lysine mimetics having aliphatic cyclic amine groups and aryl amines include Damba, 4 Amp, 4 Ampi, Ica, Pip, and 4AmF, having the following structures:

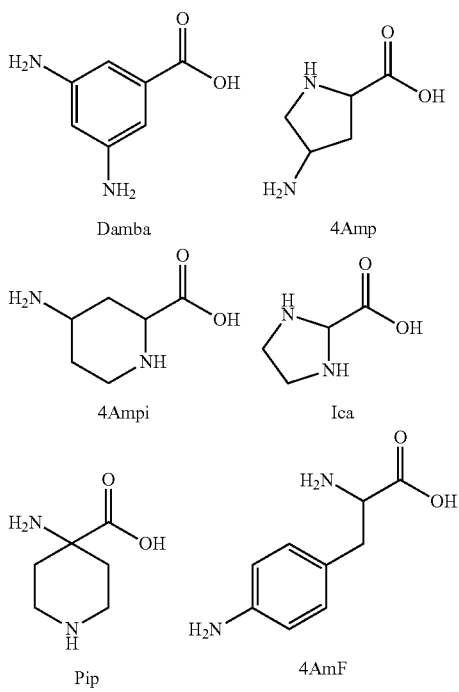

The term "halogen" refers to F, Cl, Br, and I.

The term "alkyl," as used herein either alone or as part of another group, refers to a substituted or unsubstituted aliphatic hydrocarbon chain, e.g., having from 1 to 10 carbon atoms, that can be straight-chain or branched. Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl) and the like. Specifically included within the definition of "alkyl" are those aliphatic hydrocarbon chains that are optionally substituted.

The term "alkenyl," as used herein either alone or as part of another group, refers to a substituted or unsubstituted aliphatic hydrocarbon chain, e.g., having from 2 to 10 carbon atoms, that can be straight-chain or branched and contains one or more carbon-carbon double bonds. The one or more double bonds can be internal (such as in 2-butene) or terminal (such as in 1-butene). Preferably alkenyl moieties contain one or two double bonds. The term "alkenyl" includes both E and Z isomers of each of the one or more double bonds. Specifically included within the definition of "alkenyl" are those aliphatic hydrocarbon chains that are optionally substituted. Examples of alkenyl moieties include vinyl, allyl, and butenyl (e.g., 1-butene and 2-butene).

The term "alkynyl," as used herein either alone or as part of another group, refers to a substituted or unsubstituted aliphatic hydrocarbon chain, e.g., having from 2 to 10 carbon atoms, that can be straight-chain or branched and contains one or more triple carbon-carbon bonds. The one or more triple carbon-carbon bonds can be internal (such as in 2-butyne) or terminal (such as in 1-butyne). Specifically included within the definition of "alkynyl" are those aliphatic hydrocarbon chains that are optionally substituted. Examples of alkynyl groups include ethynyl, propynyl, butynyl, pentynyl, and the like.

As used herein either alone or as part of another group, the term "cycloalkyl" refers to substituted or unsubstituted non-aromatic carbocyclic groups, e.g., having from 3 to 20 ring carbon atoms and optionally containing one or more (e.g., 1, 2 or 3) double or triple bonds, including cyclized alkyl, alkenyl, and alkynyl groups. Cycloalkyl groups can be monocyclic (e.g., cyclohexyl) or poly-cyclic (e.g. fused, bridged, or Spiro ring systems), wherein the carbon atoms are located inside or outside of the ring system. Any suitable ring position of the cycloalkyl moiety can be covalently linked to the defined chemical structure. Examples of cycloalkyl groups include cyclopropyl, cyclopropylmethyl, cyclobutyl, cyclopentyl, cyclohexyl, cyclohexylmethyl, cyclohexylethyl, cycloheptyl, cyclopentenyl, cyclohexenyl, cyclohexadienyl, cycloheptatrienyl, norbornyl, norpinyl, norcarnyl, adamantyl, spiro[4.5]decanyl groups, homologs, isomers, and the like. Also included in the definition of cycloalkyl groups are moieties that have one or more aromatic rings fused (i.e., having a bond in common with) to the cycloalkyl ring, for example, benzo derivatives of cyclopentane (indanyl), cyclohexane (tetrahydronaphthyl), and the like. Specifically included within the definition of "cycloalkyl" are those carbocycles that are optionally substituted.

The term "aryl," as used herein either alone or as part of another group, refers to substituted or unsubstituted aromatic monocyclic or polycyclic hydrocarbons such as, for example, phenyl, naphthyl, anthracenyl, phenanthrenyl, and the like. In some embodiments, aryl groups have from 6 to about 20 carbon atoms. Any suitable ring position of the aryl moiety can be covalently linked to the defined chemical structure (e.g., 1-naphthyl, 2-naphthyl, etc.). Specifically included within the definition of "aryl" are those aromatic hydrocarbons that are optionally substituted.

The term "aralkyl" refers to an aryl moiety, as defined herein, bonded to an alkyl moiety, as defined herein. Aralkyl groups are covalently linked to the defined chemical structure through their alkyl groups. Aralkyl groups optionally can be substituted on the aryl moiety, the alkyl moiety, or both.

As used herein either alone or as part of another group, "cycloheteroalkyl" refers to a substituted or unsubstituted non-aromatic cycloalkyl group, e.g., having from 3 to 20 ring atoms, that contains 1-4 ring heteroatoms independently selected from oxygen (O), nitrogen (N) and sulfur (S), and optionally contains one or more (e.g., 1, 2 or 3) double or triple bonds. The cycloheteroalkyl group can be attached to the defined chemical structure at any heteroatom or carbon atom that results in a stable structure. One or more N or S atoms in a cycloheteroalkyl ring can be oxidized (e.g., N-hydroxypiperidine, morpholine N-oxide, thiomorpholine S-oxide, thiomorpholine S,S-dioxide). Examples of cycloheteroalkyl groups include morpholine, thiomorpholine, pyran, imidazolidine, imidazoline, oxazolidine, pyrazolidine, pyrazoline, pyrrolidine, pyrroline, tetrahydrofuran, tetrahydrothiophene, piperidine, piperazine, and the like. Also included in the definition of cycloheteroalkyl are moieties that have one or more aromatic rings fused (i.e., have a bond in common with) to the cycloheteroalkyl ring, for example, benzimidazoline, chromane, chromene, indolinetetrahydroquinoline, and the like. Cycloheteroalkyl groups can also contain one or more oxo groups, such as phthalimide, piperidone, oxazolidinone, pyrimidine-2,4(1H,3H)-dione, pyridin-2(1H)-one, and the like. Specifically included within the definition of "cycloheteroalkyl" are those ring systems that are optionally substituted on any heteroatom and/or carbon atom that results in a stable structure.

As used herein either alone or as part of another group, "heteroaryl" refers to monocyclic or polycyclic aromatic ring systems having from 5 to 20 ring atoms and containing 1-4 ring heteroatoms independently selected from O, N and S. Generally, heteroaryl rings do not contain O—O, S—S, or S—O bonds. Heteroaryl groups include monocyclic heteroaryl rings fused to a phenyl ring. The heteroaryl group can be attached to the defined chemical structure at any heteroatom or carbon atom that results in a stable structure. One or more N or S atoms in a heteroaryl ring can be oxidized (e.g., N-hydroxypyridine, pyridine N-oxide, thiophene S-oxide, thiophene S,S-dioxide). Examples of heteroaryl groups include, for example, pyrrole, furan, thiophene, pyridine, pyrimidine, pyridazine, pyrazine, triazole, pyrazole, imidazole, isothiazole, thiazole, thiadiazole, isoxazole, oxazole, oxadiazole, indole, isoindole, benzofuran, benzothiophene, quinoline, 2-methylquinoline, isoquinoline, quinoxaline, quinazoline, benzotriazole, benztetrazole, indazole, benzimidazole, benzothiazole, benzisothiazole, benzisoxazole, benzoxadiazole, benzoxazole, cinnoline, 1H-indazole, 2H-indazole, indolizine, isobenzofuran, naphthyridine, phthalazine, pteridine, purine, oxazolopyridine, thiazolopyridine, imidazopyridine, furopyridine, thienopyridine, pyridopyrimidine, pyridopyrazine, pyridopyridazine, thienothiazole, thienoxazole, and thienoimidazole. Specifically included within the definition of "heteroaryl" are those aromatic ring systems that are optionally substituted on any heteroatom and/or carbon atom that results in a stable structure.

The term "heterocycle" means a heteroaryl or cycloheteroalkyl as defined herein.

As used herein, "carboxylic acid bioisostere" means a substituent or group that has chemical or physical properties similar to that of a carboxylic acid moiety and that produces broadly similar biological properties to that of a carboxylic acid moiety. See, generally, R. B. Silverman, The Organic Chemistry of Drug Design and Drug Action (Academic Press, 1992). Examples of carboxylic acid bioisosteres include, but are not limited to, amides, sulfonamides, sulfonic acids, phosphonamidic acids, alkyl phosphonates, N-cyanoacetamides, 3-hydroxy-4H-pyran-4-one, imidazoles, oxazoles, thiazoles, pyrazoles, triazoles, oxadiazoles, thiadiazoles, or tetrazoles, each of which optionally can be substituted (e.g., by $C_{1-10}$ alkyl, OH, etc.).

As used herein, "amide bioisostere" means a substituent or group that has chemical or physical properties similar to that of an amide moiety and that produces broadly similar biological properties to that of an amide moiety. See, generally, R. B. Silverman, The Organic Chemistry of Drug Design and Drug Action (Academic Press, 1992). Examples of amide bioisosteres include, but are not limited to, carboxylic acids, sulfonamides, sulfonic acids, phosphonamidic acids, alkyl phosphonates, N-cyanoacetamides, 3-hydroxy-4H-pyran-4-one, imidazoles, oxazoles, thiazoles, pyrazoles, triazoles, oxadiazoles, thiadiazoles, or tetrazoles, any of which optionally can be substituted (e.g., by $C_{1-10}$ alkyl, OH, etc.).

The phrase "hydrophobic group" refers to an optionally substituted aromatic carbon ring, preferably a 6- to 12-membered aromatic carbon ring. The hydrophobic group can be optionally substituted as discussed below. Illustrative hydrophobic groups include benzyl, phenyl, and napthyl.

The term "optionally substituted" as used herein means one or more hydrogen atoms (e.g., 1, 2, 3, 4, 5, or 6 hydrogen atoms) of the group can each be replaced with a substituent atom or group commonly used in pharmaceutical chemistry. Each substituent can be the same or different. Examples of suitable substituents include, but are not limited to, alkyl, alkenyl, alkynyl, cycloalkyl, aryl, aralkyl, cycloheteroalkyl, heteroaryl, $OR^6$ (e.g., hydroxyl, alkoxy (e.g., methoxy, ethoxy, and propoxy), aryloxy, heteroaryloxy, aralkyloxy, ether, ester, carbamate, etc.), hydroxyalkyl, alkoxycarbonyl, alkoxyalkoxy, perhaloalkyl, perfluoroalkyl (e.g., $CF_3$, $CF_2CF_3$), perfluoroalkoxy (e.g., $OCF_3$, $OCF_2CF_3$), alkoxyalkyl, $SR^6$ (e.g., thiol, alkylthio, arylthio, heteroarylthio, aralkylthio, etc.), $S^+R^6{}_2$, $S(O)R^6$, $SO_2R^6$, $NR^6R^7$ (e.g., primary amine (i.e., $NH_2$), secondary amine, tertiary amine, amide, carbamate, urea, etc.), hydrazide, halide, nitrile, nitro, sulfide, sulfoxide, sulfone, sulfonamide, thiol, carboxy, aldehyde, keto, carboxylic acid, ester, amide, imine, and imide, including seleno and thio derivatives thereof, wherein each of the substituents can be optionally further substituted. Preferably, 1-3 optional substituents can be present, wherein the substituents are Q groups as defined herein. In embodiments in which a functional group with an aromatic carbon ring is substituted, such substitutions will typically number less than about 10 substitutions, more preferably about 1 to 5, with about 1 or 2 substitutions being preferred.

The carbon numbers used in the definitions herein (e.g., $C_{1-10}$ alkyl, $C_{2-10}$ alkenyl, $C_{2-10}$ alkynyl, $C_{6-20}$ aryl, etc.) refer to the carbon backbone and carbon branching, but do not include carbon atoms of substituents.

At various places in the present specification substituents of compounds of the present teachings are disclosed in groups or in ranges. It is specifically intended that the present teachings include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. Similarly, the term "$C_{1-10}$ alkyl" is specifically intended to individually disclose $C_1$, $C_2$, $C_3$, $C_4$, $C_5$, $C_6$, $C_7$, $C_8$, $C_9$, $C_{10}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{19}$, $C_2$-$C_9$, $C_2$-$C_{10}$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{19}$, $C_4$-$C_9$, $C_4$-$C_9$, $C_4$-$C_7$, $C_4$-$C_6$, $C_4$-$C_5$, $C_5$-$C_{10}$, $C_5$-$C_9$, $C_5$-$C_8$, $C_6$-$C_{10}$, $C_6$-$C_9$, $C_6$-$C_9$, $C_6$-$C_7$, $C_7$-$C_{10}$, $C_7$-$C_9$, $C_7$-$C_8$, $C_8$-$C_{10}$, $C_8$-$C_9$, and $C_9$-$C_{10}$ alkyl.

The compounds of the present teachings can contain an asymmetric atom (also referred to as a chiral center), and some of the compounds can contain one or more asymmetric atoms or centers, which can thus give rise to optical isomers (enantiomers) and diastereomers. The present teachings include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

The terms "intercellular communication modulator", "gap junction facilitator", "compound that facilitates gap junction communication" and "gap junction opener", etc., all refer to a compound that facilitates, or maintains, or normalizes, gap junction intercellular communication (GJIC), irrespective of the particular mechanism behind this action. More specifically, the term "gap junction opener" can refer to a substance that normalizes (i.e., increases) the exchange of molecules that are able to pass through gap junctions between extracellular and intracellular spaces and/or which can normalize or increase GJIC.

The term "agonist"" refers to an compound that can interact with a tissue, cell or cell fraction which is the target of an AAP, AAP10, or HP5 compound (or functional analogue thereof), to cause substantially the same physiological responses in the tissue, cell or cell fraction as the AAP, AAP10, or HP5 compound (or functional analogue thereof). In one aspect, the physiological response is one or more of contraction, relaxation, secretion, enzyme activation, etc. Preferably, the compound binds to the tissue, cell or cell fraction. In one aspect, the compound binds to a receptor on the tissue, cell, or cell fraction, which binds to AAP, AAP10, or HP5 (or a functional analogue thereof).

The term "antagonist" refers to a compound which inhibits or antagonizes one or more physiological responses observed in a tissue, cell or cell fraction after contacting the tissue, cell, or cell fraction with AAP, AAP10, or HP5 compound (or functional analogue thereof). In one aspect, the physiological response is one or more of contraction, relaxation, secretion, enzyme activation, etc. Preferably, the compound binds to the tissue, cell or cell fraction. In one aspect, the compound binds to a receptor on the tissue, cell, or cell fraction which binds to AAP, AAP10, or HP5 (or functional analogue thereof) and/or which inhibits binding of one or more of AAP, AAP10, or HP5 (or functional analogue thereof) to the receptor.

As used herein, "normalize" refers to a change in a physiological response such that the response becomes insignificantly different from one observed in a normal patient. Thus, normalization can involve an increase or decrease in the response depending on the pathology involved.

B. Exemplary Compounds

Exemplary compounds according to the present teachings are listed below. In some cases, alternate names for the compounds are included in parentheses after the chemical name.

Compound 1: (2S,4R)1-(2-Amino-acetyl)-4-(4-nitro-benzoylamino)-pyrrolidine-2-carboxylic acid (H-Gly-(2S, 4R)-4 Amp(4-Nitrobenzoyl)-OH)

Compound 2: (2S4R)1-(2-Amino-acetyl)-4-benzoylamino-pyrrolidine-2-carboxylic acid ((2S,4R)-1-(2-aminoacetyl)-4-benzamidopyrrolidine-2-carboxylic acid, H-Gly-(2S,4R)-4 Amp(Benzoyl)-OH)

Compound 3: (2S,4R)1-(2-Amino-acetyl)-4-(4-methyl-benzoylamino)-pyrrolidine-2-carboxylic acid (H-Gly-(2S, 4R)-4 Amp(4-methylbenzoyl)-OH)

Compound 4: (2S,4R)1-(2-Amino-acetyl)-4-(4-methoxy-benzoylamino)-pyrrolidine-2-carboxylic acid (H-Gly-(2S, 4R)-4 Amp(4-methoxybenzoyl)-OH)

Compound 5: (2S,4R)1-(3-Amino-propionyl)-4-benzoylamino-pyrrolidine-2-carboxylic acid (H-Ala-(2S,4R)-4 Amp(benzoyl)-OH)

Compound 6: (2S,4R)1-(2-Amino-4-carboxy-butyryl)-4-benzoylamino-pyrrolidine-2-carboxylic acid (H-Glu-(2S, 4R)-4 Amp(benzoyl)-OH)

Compound 7: (2S,4R)1-[2-Amino-3-(1H-indol-3-yl)-propionyl]-4-benzoylamino-pyrrolidine-2-carboxylic acid (H-Trp-(2S,4R)-4 Amp(benzoyl)-OH)

Compound 8: (2S,4R)1-(2-Amino-4-methyl-pentanoyl)-4-benzoylamino-pyrrolidine-2-carboxylic acid (H-Leu-(2S, 4R)-4 Amp(benzoyl)-OH)

Compound 9: (2S,4R)1-(2-Amino-3-phenyl-propionyl)-4-benzoylamino-pyrrolidine-2-carboxylic acid (H-Phe-(2S, 4R)-4 Amp(benzoyl)-OH)

Compound 10: (2S,4R)1-(2-Amino-acetyl)-4-(4-hydroxy-benzoylamino)-pyrrolidine-2-carboxylic acid (H-Gly-(2S, 4R)-4 Amp(4-hydroxybenzoyl)-OH)

Compound 11: (2S,4S)1-(2-Amino-acetyl)-4-(4-methoxy-benzoylamino)-pyrrolidine-2-carboxylic acid (H-Gly-(2S, 4S)-4 Amp(4-methoxybenzoyl)-OH)

Compound 12: (2S,4S)1-(2-Amino-acetyl)-4-(4-methyl-benzoylamino)-pyrrolidine-2-carboxylic acid (H-Gly-(2S, 4S)-4 Amp(4-methylbenzoyl)-OH)

Compound 13: (2S,4S)1-(2-Amino-acetyl)-4-(4-nitro-benzoylamino)-pyrrolidine-2-carboxylic acid (H-Gly-(2S, 4S)-4 Amp(4-nitrobenzoyl)-OH)

Compound 14: (2S,4S)1-(2-Amino-acetyl)-4-benzoylamino-pyrrolidine-2-carboxylic acid (H-Gly-(2S,4S)-4 Amp(benzoyl)-OH)

Compound 15: (2S4S) 1-(2-Amino-4-carboxy-butyryl)-4-benzoylamino-piperidine-2-carboxylic acid (H-Glu-(2S4S)-4 Ampi(benzoyl)-OH)

Compound 16: (2S4S) 1-(2-Amino-4-methyl-pentanoyl)-4-benzoylamino-piperidine-2-carboxylic acid (H-Leu-(2S4S)-4 Ampi(benzoyl)-OH)

Compound 17: (2S4S) 4-Benzoylamino-1-(2,6-diamino-hexanoyl)-piperidine-2-carboxylic acid (H-Lys-(2S4S)-4 Ampi(benzoyl)-OH)

Compound 18: (2S4S) 1-(2-Amino-acetyl)-4-benzoylamino-piperidine-2-carboxylic acid (H-Gly-(2S4S)-4 Ampi(Benzoyl)-OH)

Compound 19: (2S4S) 1-(3-Amino-propionyl)-4-benzoylamino-piperidine-2-carboxylic acid (H-Ala-(2S4S)-4 Ampi(benzoyl)-OH)

Compound 20: (2S4S) 1-[2-Amino-3-(1H-indol-3-yl)-propionyl]-4-benzoylamino-piperidine-2-carboxylic acid (H-Trp-(2S4S)-4 Ampi(Benzoyl)-OH)

Compound 21: (2S4S) 1-(2-Amino-3-phenyl-propionyl)-4-benzoylamino-piperidine-2-carboxylic acid (H-Phe-(2S4S)-4 Ampi(Benzoyl)-OH)

Compound 22: 1-(2-Amino-4-carboxy-butyroyl)-3-benzoyl-imidazolidine-2-carboxylic acid (H-Glu-Ica(Benzoyl)-OH)

Compound 23: 4-(2-Amino-acetylamino)-1-benzoyl-piperidine-4-carboxylic acid (H-Gly-Pip(Benzoyl)-OH)

Compound 24: 3-(2-Amino-acetylamino)-5-(4-methyl-benzoylamino)-benzoic acid (H-Gly-Damba(4-methylbenzoyl)-OH)

Compound 25: 3-(2-Amino-3-carbamoyl-propionylamino)-5-benzoylamino-benzoic acid (H-Asn-Damba(Benzoyl)-OH)

Compound 26: 3-(2-Amino-acetylamino)-5-benzoylamino-benzoic acid (H-Gly-Damba(Benzoyl)-OH)

Compound 27: (2S,4R) 3-[(4-Benzoylamino-pyrrolidine-2-carbonyl)-amino]-propionic acid ((2S4R)H-4 Amp(benzoyl)-betaAla-OH)

Compound 28: (2S,4R) {[4-(4-Nitro-benzoylamino)-pyrrolidine-2-carbonyl]-amino}-acetic acid ((2S4R)H-4 Amp(4-Nitrobenzoyl)-Gly-OH)

Compound 29: (2S,4R) {[4-(4-Methoxy-benzoylamino)-pyrrolidine-2-carbonyl]-amino}-acetic acid ((2S4R)H-4 Amp(4-Methoxybenzoyl)-Gly-OH)

Compound 30: (2S,4R) 2-{[4-(4-Methyl-benzoylamino)-pyrrolidine-2-carbonyl]-amino}-acetic acid ((2S4R)H-4 Amp(Toluoyl)-Gly-OH)

Compound 31: (2S,4R) 2-[(4-Benzoylamino-pyrrolidine-2-carbonyl)-amino]-3-phenyl-propionic acid ((2S4R)H-4 Amp(benzoyl)-Phe-OH)

Compound 32: (2S,4R) 2-[(4-Benzoylamino-pyrrolidine-2-carbonyl)-amino]-4-methyl-pentanoic acid ((2S4R)H-4 Amp(benzoyl)-Leu-OH)

Compound 33: (2S,4R) 4-Benzoylamino-pyrrolidine-2-carboxylic acid (5-amino-1-formyl-pentyl)amide ((2S4R) H-4 Amp(benzoyl)-Lys-OH)

Compound 34: (2S,4R) 2-[(4-Benzoylamino-pyrrolidine-2-carbonyl)-amino]-succinamic acid ((2S4R)H-4 Amp(benzoyl)-Asn-OH)

Compound 35: (2S,4S) [(4-Benzoylamino-pyrrolidine-2-carbonyl)-amino]-acetic acid ((2S4S)H-4 Amp(Benzoyl)-Gly-OH)

Compound 36: (2S,4S) [(4-(4-Methoxy-benzoylamino)-pyrrolidine-2-carbonyl)-amino]-acetic acid ((2S4S)H-4 Amp(4-Methoxybenzoyl)-Gly-OH)

Compound 37: (2S,4S) [(4-(4-Nitro-benzoylamino)-pyrrolidine-2-carbonyl)-amino]-acetic acid ((2S4S)H-4 Amp(4-Nitrobenzoyl)-Gly-OH)

Compound 38: (2S,4S) [(4-(4-Methyl-benzoylamino)-pyrrolidine-2-carbonyl)-amino]-acetic acid ((2S4S)H-4 Amp(Toluoyl)-Gly-OH)

Compound 39: [2-Amino-3-(4-benzoylamino-phenyl)-propionylamino]-acetic acid (H-4AmF(Benzoyl)-Gly-OH)

Compound 40: [2-Amino-3-(4-(4-Methoxy-benzoylamino-phenyl)-propionylamino]-acetic acid (H-4AmF(4-Methoxybenzoyl)-Gly-OH)

Compound 41: [2-Amino-3-(4-(4-Nitro-benzoylamino-phenyl)-propionylamino]-acetic acid (H-4AmF(4-Nitrobenzoyl)-Gly-OH)

Compound 42: [2-Amino-3-(4-(4-Methyl-benzoylamino-phenyl)-propionylamino]-acetic acid (H-4AmF(Toluoyl)-Gly-OH)

Compound 43: [(1-Benzoyl-imidazolidine-2-carbonyl)-amino]acetic acid (H-Ica(Benzoyl)-Gly-OH)

Compound 44: {[1-(4-Nitro-benzoyl]-imidazolidine-2-carbonyl]amino}acetic acid (H-Ica(4-Nitrobenzoyl)-Gly-OH)

Compound 45: (2S,4S) {[4-Benzoylamino-piperidine-2-carbonyl]-amino}-acetic acid ((2S4S)H-4 Ampi(Benzoyl)-Gly-OH)

Compound 46: (2S,4S) {[4-Benzoylamino-piperidine-2-carbonyl]-amino}-propionic acid ((2S4S)H-4 Ampi(benzoyl)-betaAla-OH)

Compound 47: [(4-Amino-1-benzoyl-piperidine-4-carbonyl)-amino]-acetic acid (H-Pip(Benzoyl)-Gly-OH)

Compound 48: (3-Amino-5-benzoylamino-benzoylamino)-acetic acid (H-Damba(Benzoyl)-Gly-OH)

Compound 49: (3-Amino-5-(4-Methoxy-benzoylamino)-benzoylamino)-acetic acid (H-Damba(4-Methoxybenzoyl)-Gly-OH)

Compound 50: (3-Amino-5-(4-Methyl-benzoylamino)-benzoylamino)-acetic acid (H-Damba(Toluoyl)-Gly-OH)

Compound 51: (3,5-Diamino-benzoylamino)-acetic acid (H-Damba-Gly-OH)

Compound 52: (2S,4R) 4-Benzoylamino-1-(2-hydroxy-acetyl)-pyrrolidine-2-carboxylic acid (HAA-(2S,4R)4-Amp(benzoyl)-OH)

Compound 53: 4-Benzoylamino-1-(2-hydroxy-acetylamino)-cyclohexanecarboxylic acid (HAA-Pip(benzoyl)-OH)

Compound 54: 3-Benzoylamino-5-(2-hydroxy-acetylamino)-benzoic acid (HAA-Damba(benzoyl)-OH)

Compound 55: (2S,4S) 4-Benzoylamino-1-(2-hydroxy-acetyl)-piperidine-2-carboxylic acid (HAA-(2S4S)4-Ampi(benzoyl)-OH)

Compound 56: 1-Benzoyl-3-(2-hydroxy-acetyl)-imidazolidine-2-carboxylic acid amide (HAA-Ica(benzoyl)-NH$_2$)

Compound 57: 1-Benzoyl-3-(2-hydroxy-acetyl)-imidazolidine-2-carboxylic acid (HAA-Ica(benzoyl)-OH)

Compound 58: 3-(4-Benzoylamino-phenyl)-2-(2-hydroxy-acetylamino)-propionic acid (HAA-4AmF(benzoyl)-OH)

Compound 59: N-{4-[2-Carbamoyl-2-(2-hydroxy-acetylamino)-ethyl]-phenyl}-benzamide (HAA-4AmF(benzoyl)-NH$_2$)

Compound 60: (2S,4R) 4-Benzoylamino-1-(2-mercaptoacetyl)-pyrrolidine-2-carboxylic acid (THAA-(2S4R)-4 Amp(benzoyl)-OH)

Compound 61: (2S,4S) 4-Benzoylamino-1-(2-mercaptoacetyl)-piperidine-2-carboxylic acid (THAA-(2S4S)-4 Ampi(benzoyl)-OH)

Compound 62: (2S,4S) 1-(2-Amino-acetyl)-4-benzoylamino-piperidine-2-carboxylic acid (H-Gly-(2S4S)-4 Ampi(benzoyl)-OH)

Compound 63: (2S,4S) [(4-Benzoylamino-piperidine-2-carbonyl)-amino]-acetic acid ((2S4S)H-4 Ampi(benzoyl)-Gly-OH)

Compound 64: (2S,4R) 1-(2-aminoacetyl)-4-benzamidopyrrolidine-2-carboxamide

Compound 65: (2S,4R) 1-(2-aminoacetyl)-4-benzamido-N-methylpyrrolidine-2-carboxamide Compound 66: (2S,4R) 1-(2-aminoacetyl)-4-benzamido-N-ethylpyrrolidine-2-carboxamide Compound 67: (2S,4R) 1-(2-aminoacetyl)-4-benzamido-N-isopropylpyrrolidine-2-carboxamide Compound 68: (2S,4R) 1-(2-aminoacetyl)-4-benzamido-N-cyclopropylpyrrolidine-2-carboxamide Compound 69: (2S,4R) 4-benzamido-1-(2-(tert-butoxycarbonylamino)acetyl) pyrrolidine-2-carboxamide Compound 70: (2S,4R) 1-(2-aminoacetyl)-4-benzamido-N-(pentan-3-yl)pyrrolidine-2-carboxamide Compound 71: (2S,4R) 1-(2-aminoacetyl)-4-benzamido-N-cyclopentylpyrrolidine-2-carboxamide Compound 72: (2S,4R) 1-(2-aminoacetyl)-4-benzamido-N-isobutylpyrrolidine-2-carboxamide Compound 73: (2S,4R) 1-(2-aminoacetyl)-4-benzamido-N-cyclobutylpyrrolidine-2-carboxamide Compound 74: (2S,4R) 1-(2-aminoacetyl)-4-benzamido-N-tert-butylpyrrolidine-2-carboxamide Compound 75: (2S,4R) 1-(2-aminoacetyl)-4-benzamido-N-(tetrahydro-2H-pyran-4-yl)pyrrolidine-2-carboxamide Compound 76: (2S,4R) 1-(2-aminoacetyl)-4-benzamido-N—((R)-3-methylbutan-2-yl)pyrrolidine-2-carboxamide Compound 77: (2S,4R) 1-(2-aminoacetyl)-4-benzamido-N—((R)-3,3-dimethylbutan-2-yl)pyrrolidine-2-carboxamide Compound 78: (2S,4R) 1-(2-aminoacetyl)-4-benzamido-N-phenylpyrrolidine-2-carboxamide Compound 79: (2S,4R) 1-(2-aminoacetyl)-4-benzamido-N—((R)-tetrahydrofuran-3-yl)pyrrolidine-2-carboxamide Compound 80: (2S,4R) 1-(2-acetamidoacetyl)-4-benzamidopyrrolidine-2-carboxylic acid Compound 81: (2S,4R) 4-benzamido-1-(2-(methylamino)acetyl)-pyrrolidine-2-carboxylic acid Compound 82: (2S,4R) 4-benzamido-1-(2-(2,2,2-trifluoroacetamido)acetyl)pyrrolidine-2-carboxylic acid Compound 83: (2S,4R) 4-benzamido-1-(2-(tert-butoxycarbonylamino)acetyl) pyrrolidine-2-carboxylic acid Compound 84: (2S,4R) 4-benzamido-1-(2-(dimethylamino)acetyl)pyrrolidine-2-carboxylic acid Compound 85: (2S,4R) 4-benzamido-1-(2-formamidoacetyl)pyrrolidine-2-carboxylic acid Compound 86: (2S,4R) 4-benzamido-1-(1H-imidazole-2-carbonyl)pyrrolidine-2-carboxylic acid Compound 87: (2S,4R) 4-benzamido-1-(1H-pyrazole-5-carbonyl)pyrrolidine-2-carboxylic acid Compound 88: (2S,4R) 4-benzamido-1-(1H-imidazole-5-carbonyl)pyrrolidine-2-carboxylic acid Compound 89: (2S,4R) 1-(2-aminoacetyl)-4-(picolinamido) pyrrolidine-2-carboxylic acid Compound 90: (2S,4R) 1-(2-aminoacetyl)-4-(nicotinamido) pyrrolidine-2-carboxylic acid Compound 91: (2S,4R) 1-(2-aminoacetyl)-4-(isonicotinamido)pyrrolidine-2-carboxylic acid Compound 92: (2S,4R) 1-(2-aminoacetyl)-4-(pyrimidine-5-carboxamido)pyrrolidine-2-carboxylic acid Compound 93: (2S,4R) 1-(2-aminoacetyl)-4-(2-fluorobenzamido)pyrrolidine-2-carboxylic acid Compound 94: (2S,4R) 1-(2-aminoacetyl)-4-(3-fluorobenzamido)pyrrolidine-2-carboxylic acid Compound 95: (2S,4R) 1-(2-aminoacetyl)-4-(4-fluorobenzamido)pyrrolidine-2-carboxylic acid Compound 96: (2S,4R) 1-(2-aminoacetyl)-4-(2-methylbenzamido)pyrrolidine-2-carboxylic acid Compound 97: (2S,4R) 1-(2-aminoacetyl)-4-(3-methylbenzamido)pyrrolidine-2-carboxylic acid Compound 98: (2S,4R) 1-(2-aminoacetyl)-4-(4-methylbenzamido)pyrrolidine-2-carboxylic acid Compound 99: (2S,4R) 1-(2-aminoacetyl)-4-(4-methoxybenzamido)pyrrolidine-2-carboxylic acid Compound 100: (2S,4R) 1-(2-aminoacetyl)-4-(3-methoxybenzamido)pyrrolidine-2-carboxylic acid Compound 101: (2S,4R) 1-(2-aminoacetyl)-4-(4-hydroxybenzamido)pyrrolidine-2-carboxylic acid Compound 102: (2S,4R) 1-(2-aminoacetyl)-4-(3-hydroxybenzamido)pyrrolidine-2-carboxylic acid Compound 103: (2S,4R) 1-(2-aminoacetyl)-4-(2-phenylacetamido)pyrrolidine-2-carboxylic acid Compound 104: (2S,4R) 1-(2-aminoacetyl)-4-(2-oxo-2-phenylethylamino)pyrrolidine-2-carboxylic acid Compound 105: (2S,4R) 1-(2-aminoacetyl)-4-(phenylamino)pyrrolidine-2-carboxylic acid Compound 106: (2S,4R) 1-(2-aminoacetyl)-4-(benzylamino)pyrrolidine-2-carboxylic acid Compound 107: (2S,4R) 1-(2-aminoacetyl)-4-(phenylsulfonamido)pyrrolidine-2-carboxylic acid Compound 108: N-((3R,5S) 1-(2-aminoacetyl)-5-(1H-tetrazol-5-yl)pyrrolidin-3-yl)benzamide Compound 109: N-((3R,5S) 1-(2-aminoacetyl)-5-(1H-imidazol-2-yl)pyrrolidin-3-yl)benzamide Compound 110: N-((3R,5S) 1-(2-aminoacetyl)-5-(5-methyl-1H-imidazol-2-yl)pyrrolidin-3-yl)benzamide Compound III: N-((3R,5S) 1-(2-aminoacetyl)-5-(5-isopropyl-1H-imidazol-2-yl)pyrrolidin-3-yl)benzamide Compound 112: N-((3R,5S) 1-(2-aminoacetyl)-5-(oxazol-2-yl)pyrrolidin-3-yl)benzamide Compound 113: N-((3R,5S) 1-(2-aminoacetyl)-5-(5-isopyloxazol-2-yl)pyrrolidin-3-yl)benzamide Compound 114: N-((3R,5S) 1-(2-aminoacetyl)-5-(5-methyloxazol-2-yl)pyrrolidin-3-yl)benzamide Compound 115: N-((3R,5S) 1-(2-aminoacetyl)-5-(4-methyloxazol-2-yl)pyrrolidin-3-yl)benzamide Compound 116: N-((3R,5S) 1-(2-aminoacetyl)-5-(1H-pyrazol-5-yl)pyrrolidin-3-yl)benzamide Compound 117: N-((3R,5S) 1-(2-aminoacetyl)-5-(3-isopropyl-1H-pyrazol-5-yl)pyrrolidin-3-yl)benzamide Compound 118: N-((3R,5S) 1-(2-aminoacetyl)-5-(3-methyl-1H-pyrazol-5-yl)pyrrolidin-3-yl)benzamide Compound 119: N-((3R,5S) 1-(2-aminoacetyl)-5-(1H-1,2,4-triazol-5-yl)pyrrolidin-3-yl)benzamide Compound 120: N-((3R,5S) 1-(2-aminoacetyl)-5-(3-methyl-1H-1,2,4-triazol-5-yl)pyrrolidin-3-yl)benzamide Compound 121: N-((3R,5S) 1-(2-aminoacetyl)-5-(3-isopropyl-1H-1,2,4-triazol-5-yl)pyrrolidin-3-yl)benzamide Compound 122: N-((3R,5S) 1-(2-aminoacetyl)-5-(1,3,4-oxadiazol-2-yl)pyrrolidin-3-yl)benzamide Compound 123: N-((3R,5S) 1-(2-aminoacetyl)-5-(5-methyl-1,3,4-oxadiazol-2-yl)pyrrolidin-3-yl)benzamide Compound 124: (2S,4R) 4-benzamido-1-(2-(4,5-dihydro-1H-imidazol-2-ylamino)acetyl)pyrrolidine-2-carboxylic acid Compound 125: (2S,4R) 1-(2-(1H-imidazol-2-ylamino)acetyl)-4-benzamidopyrrolidine-2-carboxylic acid Compound 126: (2S,4R) 1-(2-(1H-pyrazol-5-ylamino)acetyl)-4-benzamidopyrrolidine-2-carboxylic acid Compound 127: (2S,4R) 4-benzamido-1-(2-(pyridin-2-ylamino)acetyl)pyrrolidine-2-carboxylic acid Compound 128: (2S,4R) 4-benzamido-1-(2-(pyrimidin-4-ylamino)acetyl)pyrrolidine-2-carboxylic acid Compound 129: (2S,4R) 4-benzamido-1-(2-(pyrimidin-2-ylamino)acetyl)pyrrolidine-2-carboxylic acid Compound 130: (2S,4R) 1-(2-(1H-imidazol-4-ylamino)acetyl)-4-benzamidopyrrolidine-2-carboxylic acid Compound 131: (2S,4R) 4-benzamido-1-(2-(3-phenylureido)acetyl)pyrrolidine-2-carboxylic acid Compound 132: (2S,4R) 4-benzamido-1-(2-(3-methylureido)acetyl)pyrrolidine-2-carboxylic acid Compound 133: (2S,4R) 4-benzamido-1-(2-(3-isopropylureido)acetyl)pyrrolidine-2-carboxylic acid Compound 134: (2S,4R) 4-benzamido-1-(2-(methylsulfonamido)acetyl)pyrrolidine-2-carboxylic acid Compound 135: (2S,4R) 4-benzamido-1-(2-(phenylsulfonamido)acetyl)pyrrolidine-2-carboxylic acid Compound 136: (2S,4R) 4-benzamido-1-(2-(1-methylethylsulfonamido)acetyl) pyrrolidine-2-carboxylic acid Compound 137: (2S,4R) 4-benzamido-1-(2-(ethylsulfonamido)acetyl)pyrrolidine-2-carboxylic acid Compound 138: (2S,4R) 1-(2-aminoacetyl)-4-(4-phenyloxazol-2-yl)pyrrolidine-2-carboxylic acid Compound 139: (2S,4R) 1-(2-aminoacetyl)-4-(5-phenyloxazol-2-yl)pyrrolidine-2-carboxylic acid Compound 140: (2S,4R) 1-(2-aminoacetyl)-4-(5-phenyl-1H-imidazol-2-yl)pyrrolidine-2-carboxylic acid Compound 141: (2S,4R) 1-(2-aminoacetyl)-4-(4-phenyl-1H-imidazol-2-yl)pyrrolidine-2-carboxylic acid Compound 142: (2S,4R) 1-(2-aminoacetyl)-4-benzamido-N-(furan-3-yl)pyrrolidine-2-carboxamide Compound 143: (2S,4R) 1-(2-aminoacetyl)-4-benzamido-N-(piperidin-4-yl)pyrrolidine-2-carboxamide Compound 144: (2S,4R) 1-(2-aminoacetyl)-4-benzamido-N-(oxazol-4-yl)pyrrolidine-2-carboxamide Compound 145: (2S,4R) 1-(2-aminoacetyl)-4-benzamido-N-(isoxazol-4-yl)pyrrolidine-2-carboxamide Compound 146: (2S,4R) 1-(2-aminoacetyl)-4-benzamido-N-(oxazol-2-yl)pyrrolidine-2-carboxamide Compound 147: (2S,4R) 1-(2-aminoacetyl)-4-benzamido-N-benzylpyrrolidine-2-carboxamide Compound 148: (2S,4R) 1-(2-aminoacetyl)-4-benzamido-N-(pyridin-4-ylmethyl)pyrrolidine-2-carboxamide Compound 149: (2S,4R) 1-(2-aminoacetyl)-4-benzamido-N-(pyridin-4-yl)pyrrolidine-2-carboxamide Compound 150: (2S,4R) 1-(2-aminoacetyl)-4-benzamido-N-(pyridin-2-yl)pyrrolidine-2-carboxamide Compound 151: (2S,4R) 1-(2-aminoacetyl)-4-benzamido-N-(pyridin-3-yl)pyrrolidine-2-carboxamide The present teachings also encompass isomers and/or enantiomers of the compounds listed above (e.g., 2S4S,2S4R, 2R4R,2R4S,3S5S,3S5R,3R5R,3R5S), as well as their salts, esters, hydrates, and prodrugs.

Pharmaceutically acceptable salts of the compounds of the present teachings having an acidic moiety can be formed using organic and inorganic bases. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di- or trihydroxy lower alkylamine (e.g., mono-, di- or triethanolamine). Internal salts also can be formed. Similarly, when a compound of the present teachings contains a basic moiety, salts can be formed using organic and inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, and camphorsulfonic as well as other known pharmaceutically acceptable acids. Amino acid addition salts can also be formed with amino acids such as lysine, glycine, or phenylalanine.

The present teachings also include prodrugs of the compounds described herein. As used herein, "prodrug" refers to a moiety that produces, generates or releases a compound of the present teachings when administered to a mammalian subject. Prodrugs can be prepared by modifying functional groups present in the compounds in such a way that the modifications are cleaved, either by routine manipulation or in vivo, from the parent compounds. Examples of prodrugs include compounds of the present teachings as described herein that contain one or more molecular moieties appended to a hydroxyl, amino, sulfhydryl, or carboxyl group of the compound, and that when administered to a mammalian subject, is cleaved in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the present teachings. Examples of preferred prodrugs include oxazolidinone or imidazolidinone prodrugs. Ester prodrugs are preferably formed with lower alcohols, such as $C_{1-6}$ alcohols. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987.

In a further aspect, the present teachings provide derivatives of the compounds, and more particularly protected forms of the compounds. By way of example, the compounds can be protected at their N- and/or C-termini, and/or at the amino acid side chain (in those compounds wherein $R^1$ is an amino acid side chain). Examples of protecting groups include tBu, Boc, Fmoc, Fm, Benzyl, Dde and Z and also include the compounds when coupled to a solid phase, e.g. when they have been made by solid phase synthesis.

C. Pharmaceutical Compositions

The compounds of the present teachings can serve as medicaments in their pure form or as pharmaceutical compositions, which can be administered via any acceptable method known in the art, either singly or in combination. Pharmaceutical compositions according to the present teachings can comprise a compound of the present teachings in admixture with one or more pharmaceutically acceptable carrier, diluent, vehicle or excipient. Such compositions can be formulated to oral administration (including buccal cavity or sublingually) or by parenteral administration (including intravenous (i.v.), subcutaneous (s.c.), intramuscular (i.m.), intraperitoneal (i.p.)) administration. Other administration routes include epidural, rectal, intranasal or dermal administration or by pulmonary inhalation. Especially preferred formulations provide sustained release of the compounds of the present teachings. The compositions are preferably in the form of solid or liquid formulations and methods for their preparation are generally described in "Remington's Pharmaceutical Sciences", 17th Ed., Alfonso R. Gennaro (Ed.), Mark Publishing Company, Easton, Pa., U.S.A., 1985.

Such compositions generally contain an effective amount of the one or more active compounds of the present teachings, together with a suitable carrier in order to provide the dosage in a form compatible with the route of administration selected. Preferably, the carrier is in the form of a vehicle, a diluent, a buffering agent, a tonicity adjusting agent, a preservative and stabilizers. The excipients constituting the carrier must be compatible with the active pharmaceutical ingredient(s) and are preferably capable of stabilizing the compounds without being deleterious to the subject being treated.

A form of repository or sustained-release formulation can be used so that therapeutically effective amounts of the preparation are delivered into the bloodstream over many hours or days following administration of the compound or composition, e.g., by transdermal injection or deposition. Formulations suitable for sustained release include biodegradable polymers, such as L-lactic acid, D-lactic acid, DL-lactic acid, glycolide, glycolic acid, and isomers thereof. Similarly, the carrier or diluent can include any sustained release material known in the art, such as glyceryl monostearate or glyceryl distearate, alone or mixed with a wax.

Other sustained release formulations can include, but are not limited to, formulations that include at least one of the compounds disclosed herein combined with liposomes, microspheres, emulsions or micelles and liquid stabilizers.

The doses the compounds and compositions of the present teachings required for the desired therapeutic effects will depend upon on the potency of the compound, the particular composition used and the route of administration selected. The compounds will typically be administered in the range of about 0.001 g to 10 g per patient per day. For example, the compounds can be administered in the range from about 1 mg to about 1000 mg per patient per day, from about 10 mg to about 100 mg per patient per day, or about 50 mg per patient per day.

The most suitable dosing regimen can best be determined by a medical practitioner for each patient individually. The optimal dosing regimen with the compounds and pharmaceutical compositions according to the present teachings depends on factors such as the particular disease or disorder being treated, the desired effect, and the age, weight or body mass index, and general physical conditions of the patient. The administration can be conducted in a single unit dosage form to alleviate acute symptoms or as a continuous therapy in the form of multiple doses over time. Alternatively, continuous infusion systems or slow release depot formulations can be employed. Two or more compounds or pharmaceutical compositions according to the present teachings can be co-administered simultaneously or sequentially in any order. In addition, the compounds and compositions can be administered in a similar manner for prophylactic purposes. Ultimately, the best dosing regimen will be decided by the attending physician for each patient individually.

D. Therapeutic Uses

Compounds according to the present teachings can facilitate and/or maintain the intercellular communication mediated by gap junctions. In one aspect, the compounds according to the present teachings target the same cells targeted by AAP, AAP10, HP5, and/or functional analogues thereof, i.e. the compounds are able to modulate the function of these cells by agonizing or antagonizing the function of AAP, AAP10, HP5, and/or functional analogues thereof. The scope of the present teachings is, however, not limited to compounds having specific AAP agonistic or antagonistic properties. The present teachings also relate to the preparation and use of pharmaceutical compositions for the treatment of pathologies which can be associated with impaired intercellular gap junction communication and methods for using these compositions, e.g. as disclosed in WO 02/077017 "New Medical Uses of Intercellular Communication Facilitating Compounds".

The present also provides methods of treating a subject having, or preventing a subject at risk from developing, a condition associated with impaired GJIC (e.g., cardiac arrhythmia or osteoporosis) comprising administering a therapeutically effective amount of any of the compounds of the present teachings. Individuals who can be treated using compounds according to the present teachings include, but are not limited to, animals, preferably mammals, e.g., rodents (including mice, rats, hamsters, and lagomorphs, such as rabbits), dogs, pigs, goats (generally any domestic animal), and primates. In one preferred aspect, the subject is a human being.

Examples of conditions which can be treated or prevented using compounds of the present teachings include, but are not limited to, cardiovascular disease; osteoporosis; inflammation of airway epithelium; disorders of alveolar tissue; bladder incontinence; impaired hearing (e.g. due to diseases of the cochlea); endothelial lesions; diabetes (Type I or Type II) and diabetic complications (including diabetic retinopathy and diabetic neuropathy); atherosclerosis; CNS related conditions; seizures; ischemia (e.g. ischemia of the central nervous system, spinal cord, brain or brain stem); dental tissue disorders (including periodontal disease); kidney diseases; haematologic manifestations (e.g., anaemia, leukopenia, thrombocytopenia, and pancytopenia, especially following treatment with cytostatic compounds or irradiation therapy); wounds (e.g., superficial wounds and deep wounds resulting trauma); bone fracture; erectile dysfunction; urinary bladder incontinence; neuropathic pain; subchronic and chronic inflammation; cancer; failure of bone marrow and stem cell transplantation; conditions which arise during transplantation of cells and tissues or during medical procedures such as surgery; conditions caused by an excess of reactive oxygen species and/or free radicals and/or nitric oxide; diseases or disorders of pregnancy (e.g., preeclampsia and preterm labor); female infertility; and stroke. Compounds according to the present teachings can also be used to induce labor (e.g., by facilitating the effect of oxytocin on uterus contraction).

In one preferred aspect, the present teachings provide a pharmacologically active antiarrhythmic compound for treatment or prevention of arrhythmias and thrombotic complications arising during cardiovascular disorders, such as acute ischemic heart disease (e.g., stable angina pectoris, unstable angina pectoris, acute myocardial infarction), congestive heart failure (e.g., systolic, diastolic, high-output, low-output, right or left sided heart failure), congenital heart diseases, cor pulmonale, cardiomyopathies, myocarditis, hypertensive heart disease, during coronary revascularization, and the like. In specific embodiments, compounds according to the present teachings can be used to treat and/or prevent bradyarrhythmias (e.g., due to disease in sinus node, AV node, bundle of His, right or left bundle branch), and tachyarrhythmias associated with reentry (e.g., atrial premature complexes, AV junctional complexes, ventricular premature complexes, atrial fibrillation, atrial flutter, paroxymal supraventricular tachycardia, sinus node reentrant tachycardia, AV nodal reentrant tachycardia, and non-sustained ventricular tachycardia). Furthermore, compounds according to the present teachings can be useful in alleviation of a pathological condition wherein slowing of conduction velocity is an important factor, e.g. ventricular tachycardia, ventricular fibrillation, and atrial fibrillation. Compounds according to the present teachings can be administered either alone or in combination with other antiarrhythmic compounds, such as class I agents (e.g., lidocaine), class II agents (e.g., metoprolol or propranolol), class III agents (e.g., amiodarone or sotalol) or class IV agents (e.g., verapamil).

Compounds according to the present teachings can also be used to treat or prevent one or more of reentry arrhythmia, ventricular reentry (e.g., arising during acute myocardial infarction, chronic myocardial infarction, stable angina pectoris and unstable angina pectoris), infectious or autonomic cardiomyopathy, atrial fibrillation, repolarization alternans, monomorphic ventricular tachycardia, T-wave alternans, bradyarrhythmias, reduced contractility of cardiac tissue, thrombosis, and the like.

Additional functions in which endothelial gap-junctional intercellular communication has been implicated are the migratory behavior of endothelial cells after injury, angiogenesis, endothelial growth and senescence and the coordination of vasomotor responses (Christ et al. Braz. *J Med. Biol. Res.*, 33, 423-429 (2000)). Therefore, compounds according to the present teachings can be used to enhance conducted vascular responses and to improve blood supply during conditions with increased metabolic demand (e.g., physical exercise, tachycardia), and during ischemia.

Compounds according to the present teachings can be used to cytoprotect a tissue or organ of a mammal in need of such treatment. Cytoprotecting refers to reducing, preventing or alleviating symptoms associated with unwanted cell swelling. Particular tissues and organs that will benefit from the method include those confined or otherwise impacted by a fibrous capsule such as heart or kidney. Also included are tissues associated with bone such as brain, spinal cord and bone marrow. Compounds of the present teachings can be used to prevent or treat ischemic injury in the organs of a mammal in need of such treatment, including, for example, the heart, central nervous system, kidney, gastrointestinal tract, liver, lungs, and limbs.

In another aspect, the present teachings provide the use of the compounds to treat or prevent haematologic manifestations following treatment with cytostatic compounds or irradiation therapy. Impaired haematopoiesis recovery is observed in patients after 5-fluorouracil (5-FU) cytostatic treatment. This includes absence of recovery of peripheral blood counts, including severe neutropenia, severe anemia with reticulocytopenia and presence of abnormal peripheral erythrocytes and severe thrombocytopenia. In addition, 5-8-fold decreases of bone marrow cellularity and hematopoietic progenitor content (granulomacrophagic colony-forming-units (CFU-GM), erythroid burst forming units (BFU-E), mixed colony forming units (CFU-mix), and overall colony forming units (CFU-C) in bone marrow are observed. (See, e.g., Montecino-Rodriguez et al., *Blood*, 96, 917-924, (2000); Presley et al., Abstract #55, IGJC 2005, Whistler, Canada (2005)). Included in this aspect of the present teachings are the treatment or prevention of general clinical situations commonly associated with iatrogenic pancytopenia.

Compounds according to the present teachings can be use to treat or prevent osteoporosis. It is known that that GJIC is important in bone formation. The efficacy of the compounds can be assessed, for example, by an increase in osteoblast activity in a standard osteoblast activity assay which measures either calcium wave formation and/or alkaline phosphatase activity of osteoblast cells in the presence of the compounds. Alkaline phosphatase activity also can be used to provide a measure of osteoblast activity using standard colorimetric assays.

Preferably, one or more of the compounds or pharmaceutical compositions according to the present teachings are administered to an individual in need thereof in a therapeutically effective amount. As used herein, "a therapeutically effective amount" refers to an amount that reduces symptoms of a given condition or pathology, and preferably which normalizes physiological responses in a subject with the condition or pathology. Reduction of symptoms or normalization of physiological responses can be determined using methods routine in the art and can vary with a given condition or pathology. In one aspect, a therapeutically effective amount of one or more compounds or pharmaceutical compositions is an amount which restores a measurable physiological parameter to substantially the same value (preferably to within ±30%, more preferably to within ±20%, and still more preferably, to within ±10% of the value) of the parameter in a subject without the condition or pathology.

The effective amount will be determined by the skilled person taking into account such factors as potency of the drug, age and constitution of the patient, body weight, pharmacokinetic profile of the drug, and in general the drug will be prescribed for each patient or group of patients. However, the effective amount of the compound can be at least about 10 μg/kg body weight/day, such as at least about 100 μg/kg body weight/day, at least about 300 μg/body weight/day, and at least about 1000 μg/kg body weight/day. On the other hand, the effective amount of the compound or dimer can be at most about 100 mg/kg body weight/day, such as at most about 50 mg/kg body weight/day and at most about 10 mg/kg body weight/day. It is expected that the effective amount of the compound will be about 100 μg/kg body weight/day, about 300 μg/kg body weight/day or about 1000 μg/kg body weight.

E. Biological Assays

Preferred compounds of the present teachings can show binding, preferably specific binding, to a tissue, cell, or cell fraction in what is referred to herein as a "standard AAP site binding test". The test can detect and optionally quantify binding of a subject compound, e.g., AAP, AAP10, HP5, or a functional analogue thereof. In one preferred embodiment, the compound can be a modulator of the function of such a tissue, cell, or cell fraction (i.e. the compound agonizes or antagonizes the function of the antiarrhythmic peptide). In another embodiment, the compound can be a modulator of a receptor for the antiarrhythmic peptide (i.e. the compound is an agonist or antagonist of the receptor). Additionally preferred compounds according to the present teachings can show good function as modulators of gap junctional communication (e.g., as agonists or antagonists of AAP). In one aspect, the compounds can function as antiarrhythmic drugs.

Preferred agonist compounds of the present teachings can provide an intracellular conductance (Gj) that is substantially the same as, or is greater than, the Gj of AAP in what is referred to herein as a "standard cardiomyocyte assay". Preferred antagonist compounds can provide a Gj that is less (e.g., at least about 10%, or at least about 20% less) than the Gj of AAP and/or block the ability of AAP to normalize the Gj of an ischemic cell, i.e., to return the Gj to substantially the same values found in non-ischemic cells. Additionally preferred compounds according to the present teachings can increase the time to an AV block in a mouse after infusion of $CaCl_2$, in what is referred to herein as a "standard calcium-induced arrhythmia assay." Compounds of the present teachings can prevent cardiac conduction slowing in the presence of various form of metabolic stress (e.g. ischemia, hypoglycaemia or acidosis) in what is referred to herein as a "standard isolated atrial strip model of metabolic stress induced conduction slowing." Compounds of the present teachings can additionally show decreases in the incidence of reentry arrhythmias or in the size of an infarct zone observed in what is referred to herein as a "standard ventricular reentry assay."

In some embodiments, compounds of the present teachings can exhibit a good half-life according to what is referred to herein as an "in vitro plasma stability assay". Compounds that show a good stability in the assay have in one embodiment a half-life of more than about 48 hours, or more than 24 hours, or more than 12 hours, or more than 6 hours, or more than 3 hours, or more than 1 hour, or more than 30 minutes, or more than 20 minutes, or more than 15 minutes, or more than 10 minutes, or more than 5 minutes, or more than 1 minute. In these embodiments, compounds of the present teachings can show enhanced stability in the bloodstream.

Particular assays useful for identifying and optionally quantifying the activity of compounds of the present teachings are further described below.

1. Standard Plasma Stability Assays

The present teachings provide compounds that have enhanced stability in vitro or in vivo. By way of example, compounds of the present teachings that comprise a peptide bond can be alkylated or otherwise modified to stabilize the compound against enzymatic degradation. Alternatively or additionally, the compounds can comprise one or more D-amino acids. It is possible to test whether a compound has enhanced stability in a standard stability assay.

In one example of an in vitro plasma stability assay, compounds are incubated in plasma or serum and samples are taken at regular intervals for analysis by HPLC or LC/MS/MS, to quantitate the amount of undegraded compound. (See, e.g., WO 02/077017, the entire disclosure of which is incorporated by reference herein). Appropriate conditions (column, solvent, gradient, and temperature) for such analyses are estimated to ensure that the compound peak and the plasma peaks do not have the same retention time. This is done by subsequent injections of a compound, plasma, and a co-injection with the compound and the plasma, followed by optimization of LC method parameters until a satisfactory separation is obtained. A control plasma sample without the peptide compound, treated in the same manner, also is taken and evaluated. The samples can include, but are not limited to, a blank, the compound at a suitable concentration (e.g., 0.1 mg/mL), plasma without compound, one or more samples for t=0, and one or more samples at each regular interval. Preferably, multiple samples are taken in parallel. The sample concentrations (peak height in mAU or ion counts) are plotted vs. time and fitted to a function describing a mono exponential decay (e.g., using a standard Excel package). Preferably, a compound according to the present teachings has a half-life of more than about 30 minutes (e.g., more than about 1 hour, or more than about 3 hours, or more than about 6 hours, or more than about 12 hours, or more than about 24 hours, or more than about 48 hours) as determined using this assay.

Plasma stability can be examined in vivo using standard assays. For example, compounds can be administered to a mammal, such as a rat, by bolus injections in volumes of about 1 ml/kg for both i.v. and p.o. dosing. Preferably, compounds are tested in parallel with control samples such as buffer or an antiarrythmic peptide with a known stability. Blood samples are collected at different time periods (e.g., at B.D. 5, 15, 30, 60, 90, 120, 180, and 240 minutes, where B.D. refers to before dose). Amounts of compounds in samples can be quantified using methods of routine in the art, such as LC/MS/MS. For example, the concentrations of compounds in plasma samples can be calculated from an external standard curve covering concentration ranges of compound from 1.00 to 1000 nM. The plasma concentrations versus time data can be used for pharmacokinetic modelling in WinNonLin 3.5 (Pharsight, Mountain view, Calif.) using non-compartmental analysis and the resulting parameters of AUC, Fpo, CIb, t1/2, $C_{max}$ and tmax can be determined as is known in the art.

2. Standard Cardiomyocyte Assays

Compounds of the present teachings can be tested in a cardiomyocyte assay, which measures the gap junction function of cardiac cells after administration of the compounds. In one example, cardiac cells are isolated from a mammal, such as a guinea pig hearts, by perfusion with collagenase according to the Langendorf method. The cells are exposed to compound and evaluated for GJIC by patch clamp using methods known in the art. Intercellular conductance (Gj) is calculated using the formula:

$$G_j = \frac{\Delta I_p}{\Delta U_j} = \frac{I_{p,pulse} - I_{p,rest}}{U_p - U_a} \quad \text{(Equation 1)}$$

where Ip,pulse and Ip,rest represent the current in the passive cell during the pulse and before the pulse respectively, and Up and Ua represent the voltage of the passive and active cell. The change in Gj value upon compound administration is analyzed by comparing the relative changes in Gj. For example, the relative Gj as a function of time before, and during, stimulation with compound (e.g., at about $10^{-8}$ M) can be determined. Preferably, the compound provides a Gj, which is substantially the same as the Gj (±10%) of an anti-arrhythmic peptide such as AAP, AAP10, HP5, and functional analogues thereof. In one example, the cell is an ischemic cell, and the compound provides a Gj, which is substantially the same as that of a non-ischemic cell (±20%, preferably, ±10%). Additional details concerning performing cardiomyocyte assays are provided in WO 02/077017.

3. Standard Calcium-induced Arrhythmia Assay

Peptides suitable for administration to cardiac cells can be identified in an in vivo model of calcium-induced arrhythmias according to the model of Lynch et al. (1981) *J Cardiovasc. Pharmacol.* 3: 49-60. Male CD-1 mice are anaesthetized with Ketamine (75 mg/kg) and medetomidine (1 mg/kg) IP. An i.v. cannula is inserted into the tail vein. A lead II ECG signal is recorded continuously by positioning stainless steel ECG electrodes on the right forelimb and left forelimb. The ground electrode is placed on the right hind limb. The signal is amplified and filtered using Gould physiograph components and po-ne-mah data acquisition software. After a 90 sec equilibration period test compound is injected into the tail vein (over 30 seconds). Mice pre-treated with vehicle are tested as control animals. The injection volume is 100 µl/30 g mice in all experiments. Infusion of $CaCl_2$ (30 mg/mL, 0.1 mL/min/30 g mice, 100 mg/kg/min) is started 3 min after IV administration of drug or vehicle (0.9% saline). The time lag to onset of cardiac conduction block is determined as the time from the start of $CaCl_2$ infusion until the first arrhythmic event occurred. The first conduction block is defined as the first RR-interval, larger than or equal to 3 times one RR-interval from the pre-treatment period. The first arrhythmic event occurring is either a second degree AV-block (intermittent failure of the AV conduction characterized by a P-wave without the concomitant QRS complex) or a second degree SA block (prolonged RR-interval and a QRS-complex without a preceding P-wave). Responses are expressed relative to the time until 2nd degree AV-block occurred in vehicle treated mice.

4. Standard Isolated Atrial Strip Model of Metabolic Stress Induced Conduction Slowing Peptides suitable for administration to cardiac cells can be identified in an in vitro model as described by Haugan et al. (*J. Cardiovasc. Electrophysiol.*, 16, 537-545 (2005)).

Rats (300-400 g) are killed by a sharp blow on the neck. The heart is rapidly excised and transferred to a small dish containing 37° oxygenated modified Tyrodes buffer containing (in mM): NaCl 136, KCl 4, $MgCl_2$ 0.8, $CaCl_2$ 1.8 HEPES 5, MES 5, Glucose 6, pH 7.3. The left atrium is carefully dissected and a tissue sample of approximately 2×6 mm is taken from the left atrial appendage and placed in a tissue chamber (volume 5 ml), (Steiert Organ Bath, Hugo Sach Electronic, Germany). The chamber is perfused throughout the study with 37° C. oxygenated Tyrodes buffer at a rate of 10 ml/min.

A bipolar stimulation electrode (Teflon coated stainless steel, diameter 75 µM) is placed at one end of the tissue. Stimulation is performed at 1 Hz using rectangular pulses at double threshold (duration of stimulus 0.2 ms) delivered by a stimulator (Hugo Sachs, Type 215) through an isolation unit (Universal Isolated Stimulator Unit type 263, Hugo Sachs, Germany).

Two separate microelectrodes of pure iridium (World Precision Instruments, tip-impedance 3.5-4.0 MΩ) are placed on a line along the long-axis of the preparation for recording of atrial CV. The distances from the stimulating electrode to the first and second microelectrode is 1.5-2.0 mm and 3.0-4.0 mm, respectively. Each microelectrode is connected to a head-stage preamplifier (10× amplification of the signals). The preamplifiers are connected to a bio potential amplifier module that is connected to the data acquisition system through a Hugo Sachs PLUGSYS. Signals are filtered at 1 kHz and sampled at 10 kHz.

Following a 30 minutes equilibration period, pacing at 1 Hz is initiated. During the first 20 minutes recording period (baseline period), the chamber is perfused with 37° C. oxygenated Tyrodes buffer, pH 7.3. Compounds (e.g., modified lysine mimetic compounds of the present teachings, AAP, AAP10 or controls) are then added to the perfusion buffer for another 20 minute period (pre-treatment period). Following the 20 minutes of pretreatment, perfusion is changed to a 37° C. glucose-free, non-oxygenated Tyrodes buffer, pH 7.3 (with or without compounds of interest) for 40 minutes (metabolic stress period).

The change in conduction velocity during metabolic stress is compared to a group of untreated controls. In untreated preparations, conduction decreases by 15-45% during the 40 minute period of metabolic stress. In some embodiments, compounds according to the present teachings can prevent metabolic stress induced conduction slowing during the 40 minutes period comparable to the compounds AAP, AAP10, HP5, or a functional analogue thereof, i.e., the compounds can preserve normal conduction during an episode of metabolic stress.

5. Haematologic Assay

Compounds of the present teachings can also be tested to determine their effects in accelerating recovery following 5-fluorouracil (5-FU) induced stress on bone marrow proliferation. Male rats are treated with 5-FU (75-100 nmol/kg i.p.) for 4 days. Blood samples are collected from tail tip before 5-FU treatment (Day 0), and 4, 8, 12, 16, 20, 24, 28 days following first 5-FU dose. Measurement of peripheral blood counts (granulocytes, lymphocytes, erythrocytes, thrombocytes, reticulocytes) and plasma haemoglobin are taken. After identification of window with severe pancytopenia, the study is repeated during concomitant treatment with a compound of the present teachings.

F. Preparation of Exemplary Compounds

The following non-limiting examples are presented merely in order to illustrate the present teachings. The skilled person in the area will understand that there are numerous equivalents and variations not exemplified but still form part of the present teachings.

Lysine mimetic compounds of the present teachings can be synthesized by means of solid phase or solution phase synthesis. In this context, reference is given to, amongst many others, Fields et al., "Principles and practice of solid-phase peptide synthesis", Synthetic Peptides (2002, 2nd Edition).

Scheme 1 depicts an exemplary synthesis of a compound of Formula III, (2S,4R)-4-benzamido-1-(2-(4,5-dihydro-1H-imidazol-2-ylamino)acetyl)pyrrolidine-2-carboxylic acid, wherein Y' is NHR³ and R³ is not hydrogen.

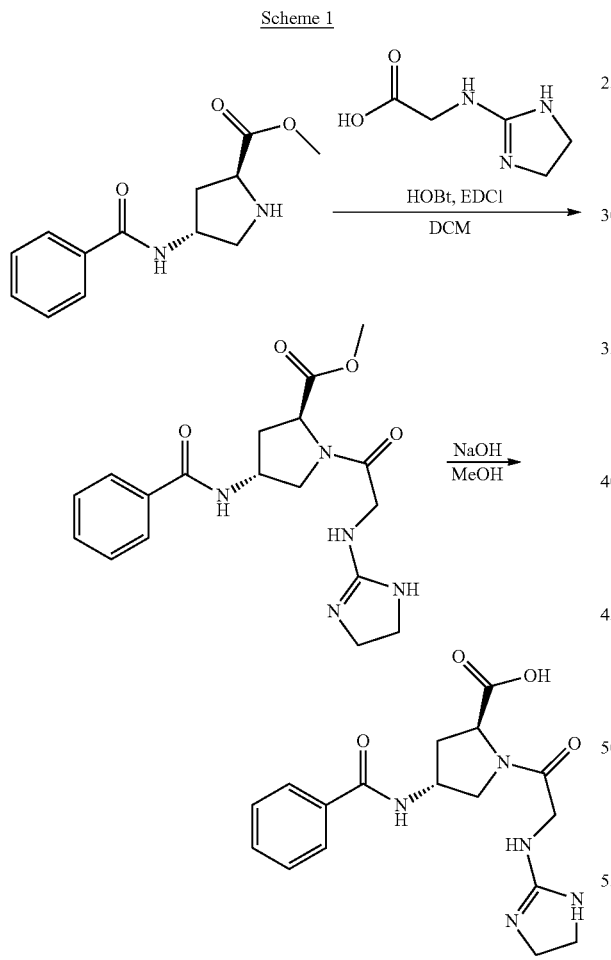

Different N-substituted amino acid derivatives can be used to synthesize other compounds of Formula III wherein Y' is NHR³ and R³ is not hydrogen. For example, 2-chloro-1H-imidazole or 4-bromo-1H-imidazole can be treated with glycine in water (for example, according to the procedure set forth in European Journal of Medicinal Chemistry (1989), 24(6), 623-5) to form 2-(1H-imidazol-2-ylamino)acetic acid or 2-(1H-imidazol-4-ylamino)acetic acid, respectively, which can then be used to synthesize (2S,4R)-1-(2-(1H-imidazol-2-ylamino)acetyl)-4-benzamidopyrrolidine-2-carboxylic acid or (2S,4R)-1-(2-(1H-imidazol-4-ylamino)acetyl)-4-benzamidopyrrolidine-2-carboxylic acid in a manner similar to Scheme 1. Compounds such as (2S,4R)-4-benzamido-1-(2-(pyridin-2-ylamino)acetyl)pyrrolidine-2-carboxylic acid, (2S,4R)-4-benzamido-1-(2-(pyrimidin-4-ylamino)acetyl)pyrrolidine-2-carboxylic acid, and (2S,4R)-4-benzamido-1-(2-(pyrimidin-2-ylamino)acetyl)pyrrolidine-2-carboxylic acid can be similarly synthesized from 2-(pyridin-2-ylamino)acetic acid, 2-(pyrimidin-4-ylamino)acetic acid, and 2-(pyrimidin-2-ylamino)acetic acid, respectively.

Alternatively, the glycine derivative can be synthesized according to Scheme 2.

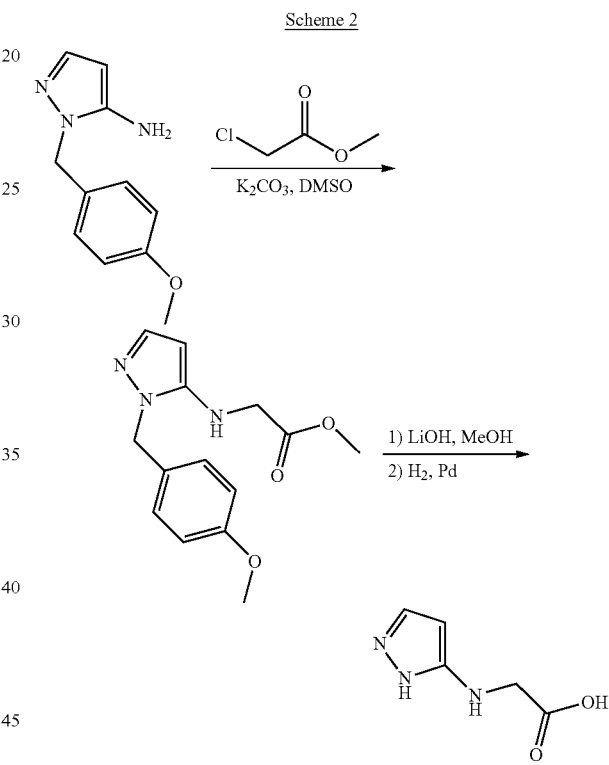

In the above example, the 2-(1H-pyrazol-5-ylamino)acetic acid thus produced can be used to synthesize (2S,4R)-1-(2-(1H-pyrazol-5-ylamino)acetyl)-4-benzamidopyrrolidine-2-carboxylic acid using the method shown in Scheme 1.

Compounds of Formula II wherein A and R¹ together with the carbon to which they are bound form a 5-20 membered heteroaryl containing one or more N, O, or S atoms can be synthesized according to Scheme 1 utilizing the appropriate carboxylic acid starting materials. For example, (2S,4R)-4-benzamido-1-(1H-imidazole-2-carbonyl)pyrrolidine-2-carboxylic acid, (2S,4R)-4-benzamido-1-(1H-pyrazole-5-carbonyl)pyrrolidine-2-carboxylic acid, or (2S,4R)-4-benzamido-1-(1H-imidazole-5-carbonyl)pyrrolidine-2-carboxylic acid can be synthesized according to Scheme 1 using 1H-imidazole-2-carboxylic acid, 1H-pyrazole-5-carboxylic acid, or 1H-imidazole-5-carboxylic acid, respectively.

Scheme 3 depicts another exemplary synthesis of a compound of Formula III wherein Y' is NHR³ and R³ is not hydrogen. In this example, (2S,4R)-4-benzamido-1-(2-(3-phenylureido)acetyl)pyrrolidine-2-carboxylic acid, $R^3$ is $C(O)NR^6R^7$.

Scheme 4 depicts an exemplary synthesis of (2S,4R)-4-benzamido-1-(2-(methylsulfonamido)acetyl)pyrrolidine-2-carboxylic acid, a compound of Formula III wherein Y' is $NHR^3$ and $R^3$ is $S(O)R^6$.

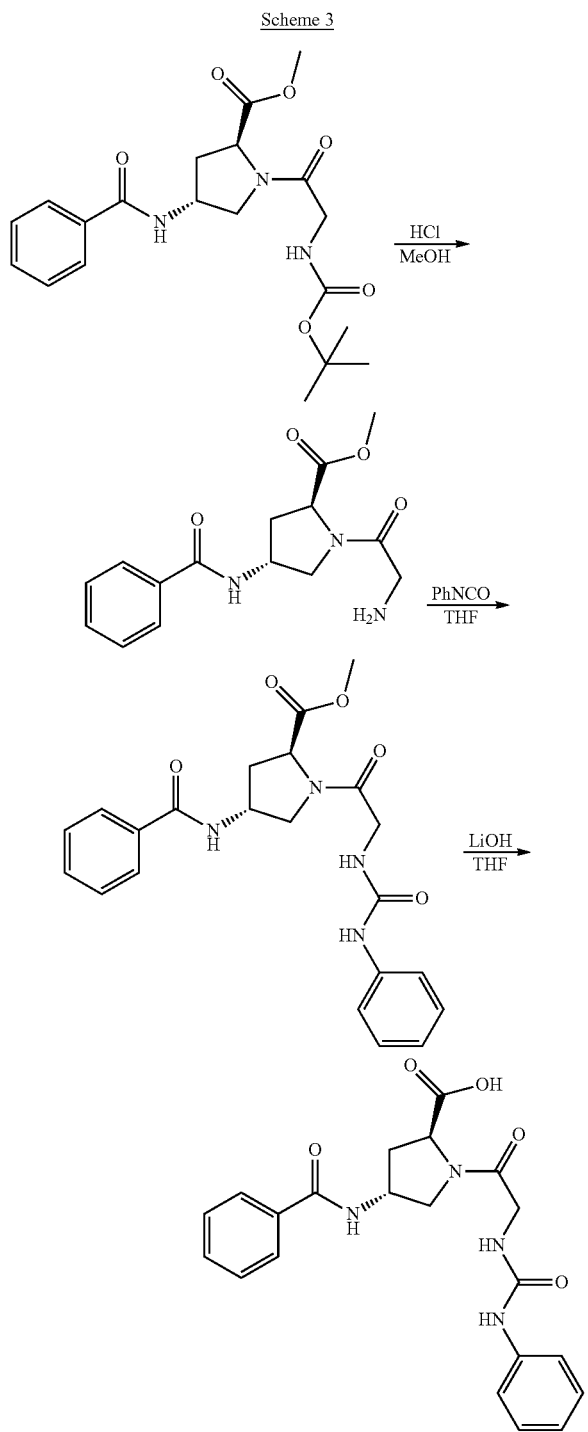

Scheme 3

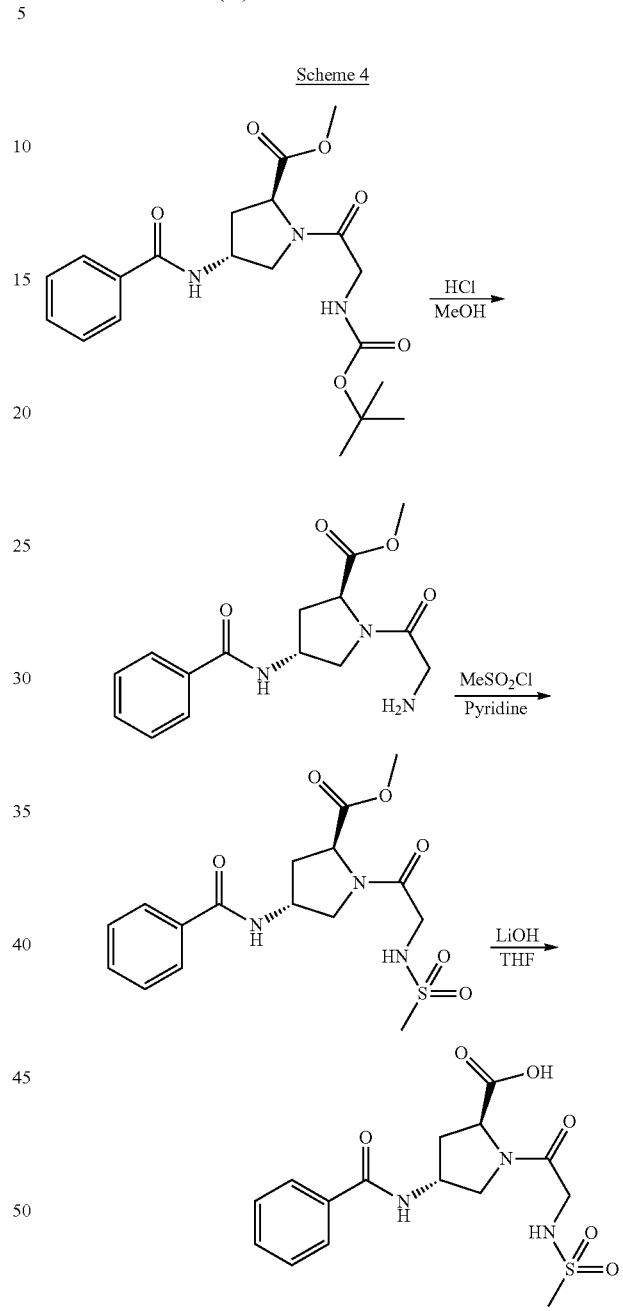

Scheme 4

Different isocyanates (e.g., methylisocyanate or isopropylisocyanate) can be employed in the synthesis of Scheme 3 to produce other ureas of Formula III (e.g., (2S,4R)-4-benzamido-1-(2-(3-methylureido)acetyl)pyrrolidine-2-carboxylic acid or (2S,4R)-4-benzamido-1-(2-(3-isopropylureido)acetyl)pyrrolidine-2-carboxylic acid).

Starting with other sulfonyl chlorides (e.g., ethanesulfonyl chloride or proane-2-sulfonyl chloride), different sulfonamides of Formula III (e.g., (2S,4R)-4-benzamido-1-(2-(ethylsulfonamido)acetyl)pyrrolidine-2-carboxylic acid or (2S,4R)-4-benzamido-1-(2-(1-methylethylsulfonamido)acetyl)pyrrolidine-2-carboxylic acid) can be prepared using the method shown in Scheme 4.

Compounds of Formula III wherein k is 1 or 2 (e.g., (2S,4R)-1-(3-aminopropanoyl)-4-benzamidopyrrolidine-2-carboxylic acid) can be synthesized, for example, according to Scheme 5.

Scheme 5

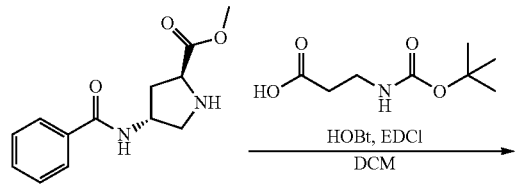

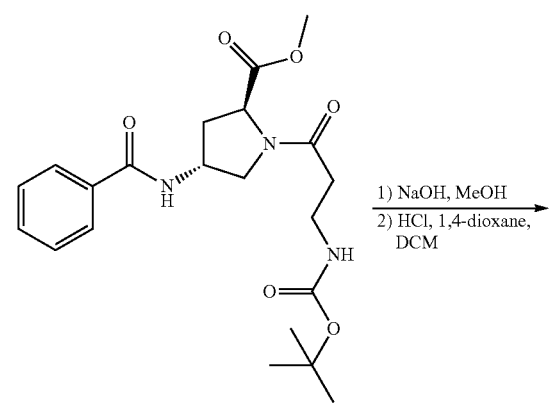

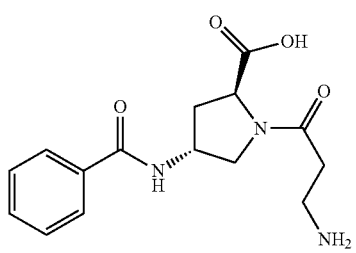

Scheme 6 shows an exemplary synthesis of a compound of Formula III, (2S,4R)-1-(2-aminoacetyl)-4-(phenylamino) pyrrolidine-2-carboxylic acid, wherein Z' is $(CH_2)_m$—$C_{6-20}$ aryl and m is 0.

Scheme 6

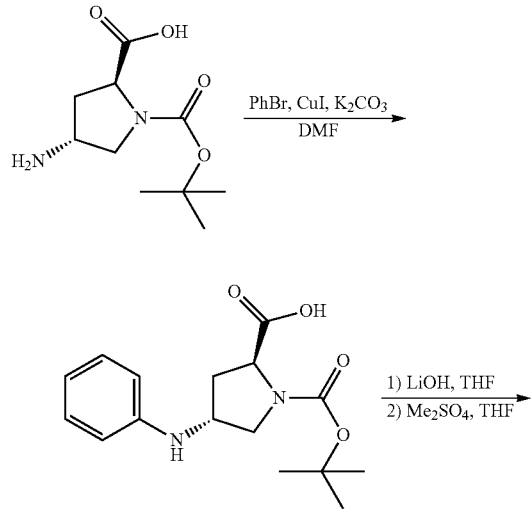

-continued

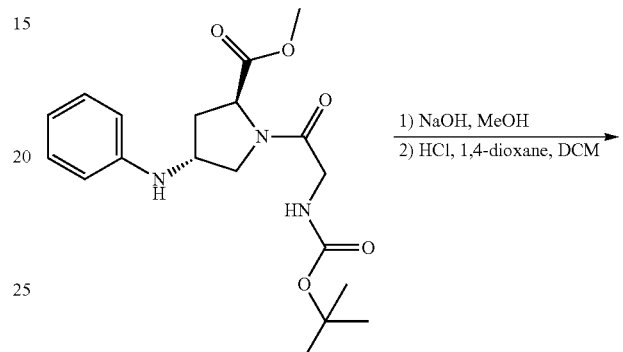

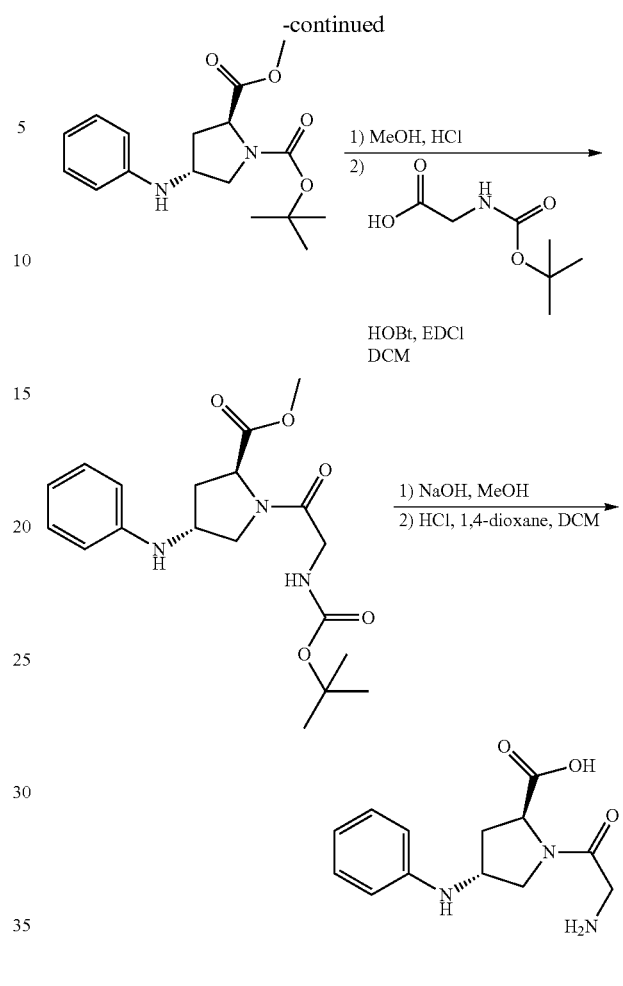

Similarly, Scheme 7 depicts an exemplary synthesis a compound of Formula III, (2S,4R)-1-(2-aminoacetyl)-4-(benzylamino)pyrrolidine-2-carboxylic acid, wherein Z' is $(CH_2)_m$—$C_{6-20}$ aryl and m is 1.

Scheme 7

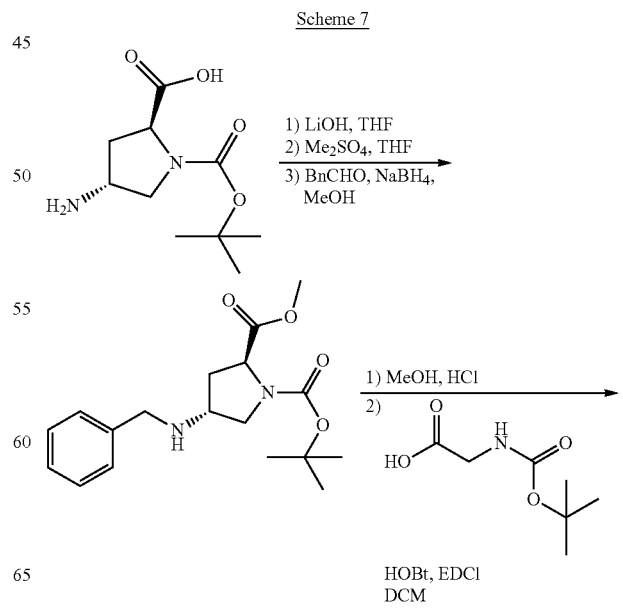

47

-continued

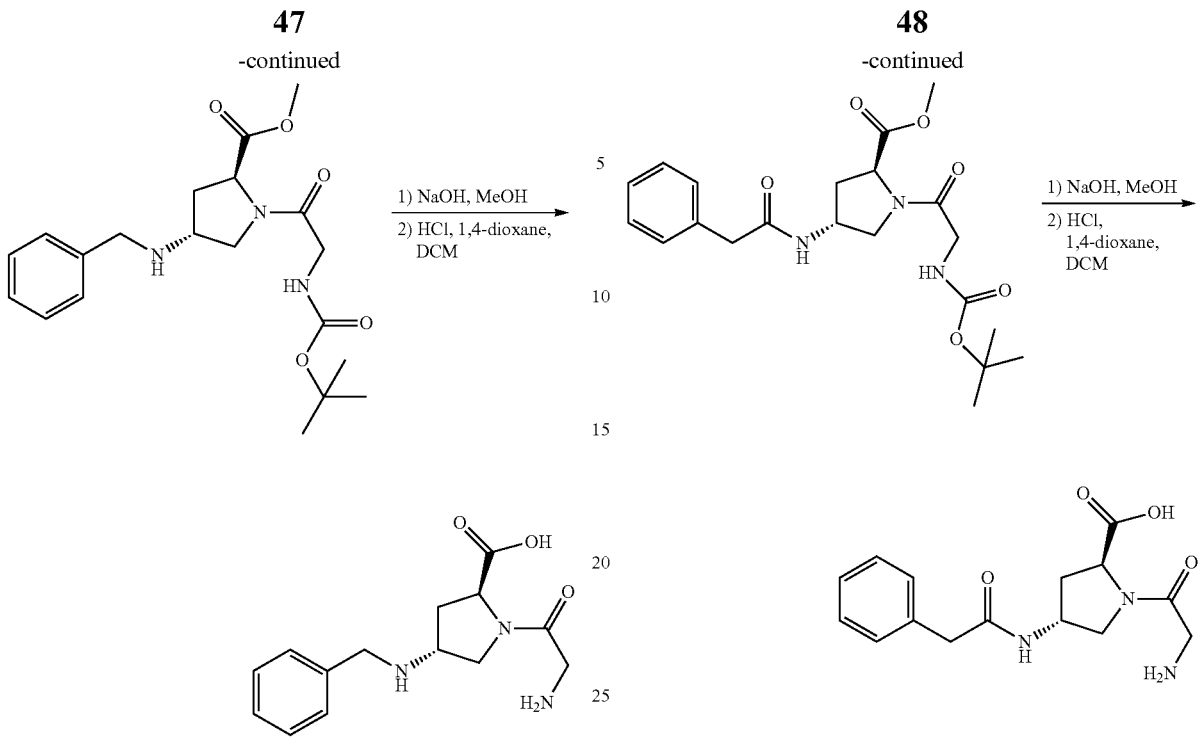

Compounds wherein Z' is $(CH_2)_m$-5-20 membered heteroaryl and m is 0 or 1 also can be prepared using the appropriate starting materials according to the methods of Schemes 6 or 7.

Scheme 8 shows an exemplary synthesis of a compound Formula III, (2S,4R)-1-(2-aminoacetyl)-4-(2-phenylacetamido)pyrrolidine-2-carboxylic acid, wherein Z' is C(O)(CH$_2$)$_m$—C$_{6-20}$ aryl and m is 1.

Scheme 8

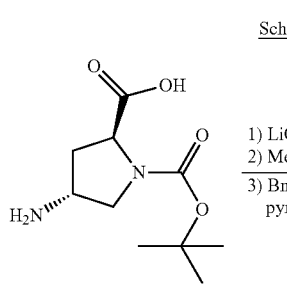

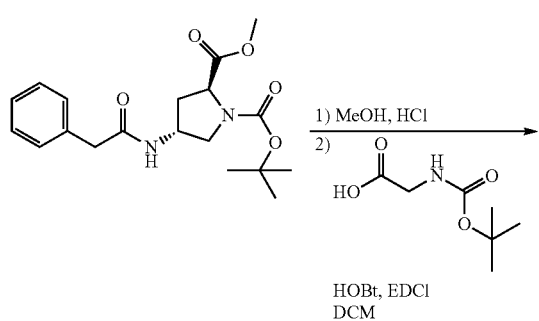

48

-continued

Compounds wherein Z' is C(O)(CH$_2$)$_m$—C$_{6-20}$ aryl and m is 2, or Z' is C(O)(CH$_2$)$_m$-5-20 membered heteroaryl and m is 1 or 2, also can be prepared using the appropriate starting materials according to the method of Scheme 8.

Compounds of Formula III wherein Z' is S(O)$_2$(CH$_2$)$_m$—C$_{6-20}$ aryl or S(O)$_2$(CH$_2$)$_m$-5-20 membered heteroaryl can be synthesized, for example, according to Scheme 9, which depicts the synthesis of (2S,4R)-1-(2-aminoacetyl)-4-(phenylsulfonamido) pyrrolidine-2-carboxylic acid.

Scheme 9

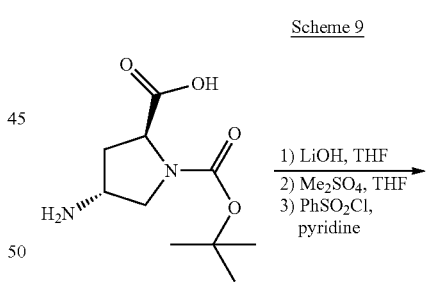

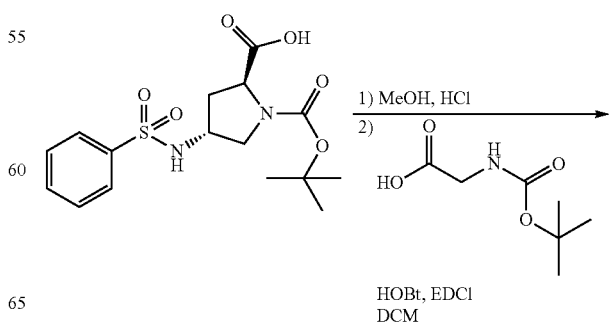

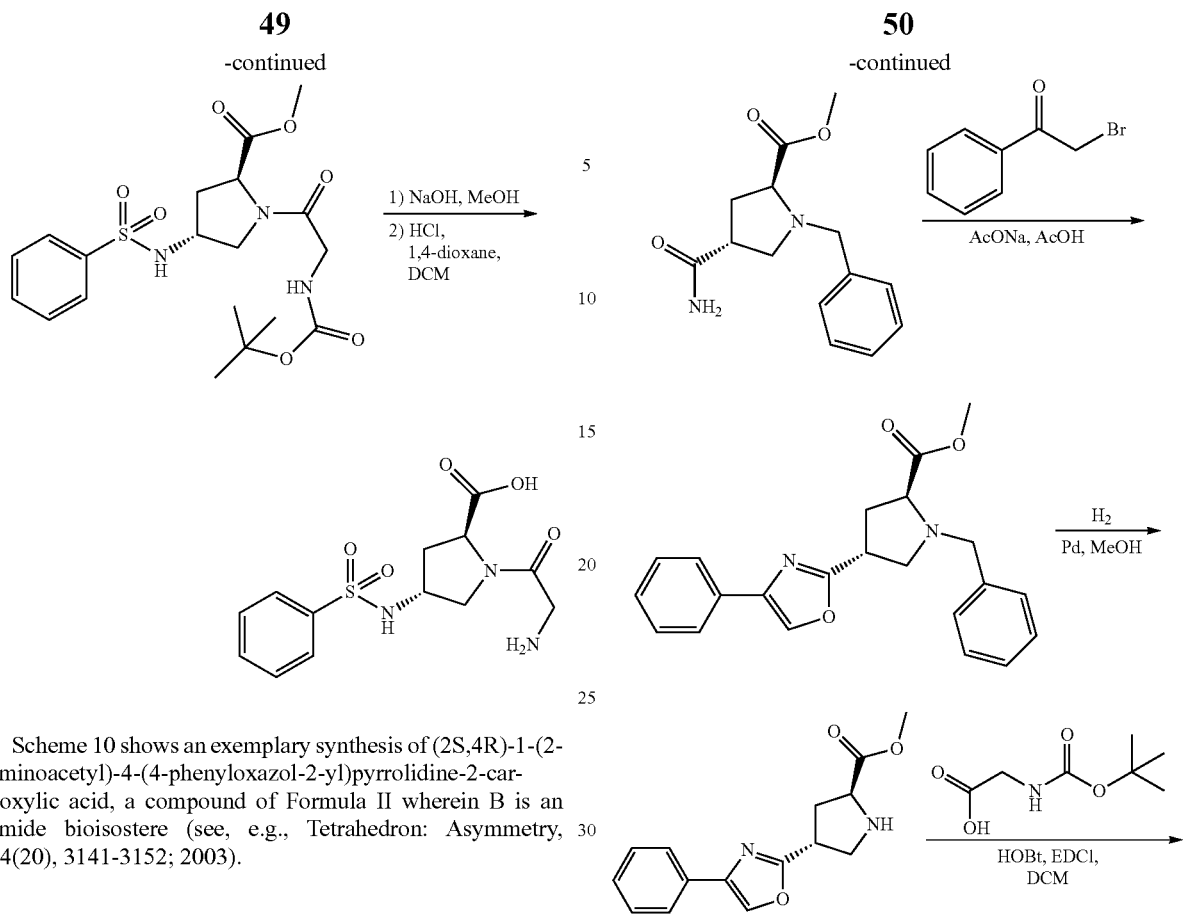

Scheme 10 shows an exemplary synthesis of (2S,4R)-1-(2-aminoacetyl)-4-(4-phenyloxazol-2-yl)pyrrolidine-2-carboxylic acid, a compound of Formula II wherein B is an amide bioisostere (see, e.g., Tetrahedron: Asymmetry, 14(20), 3141-3152; 2003).

Scheme 10

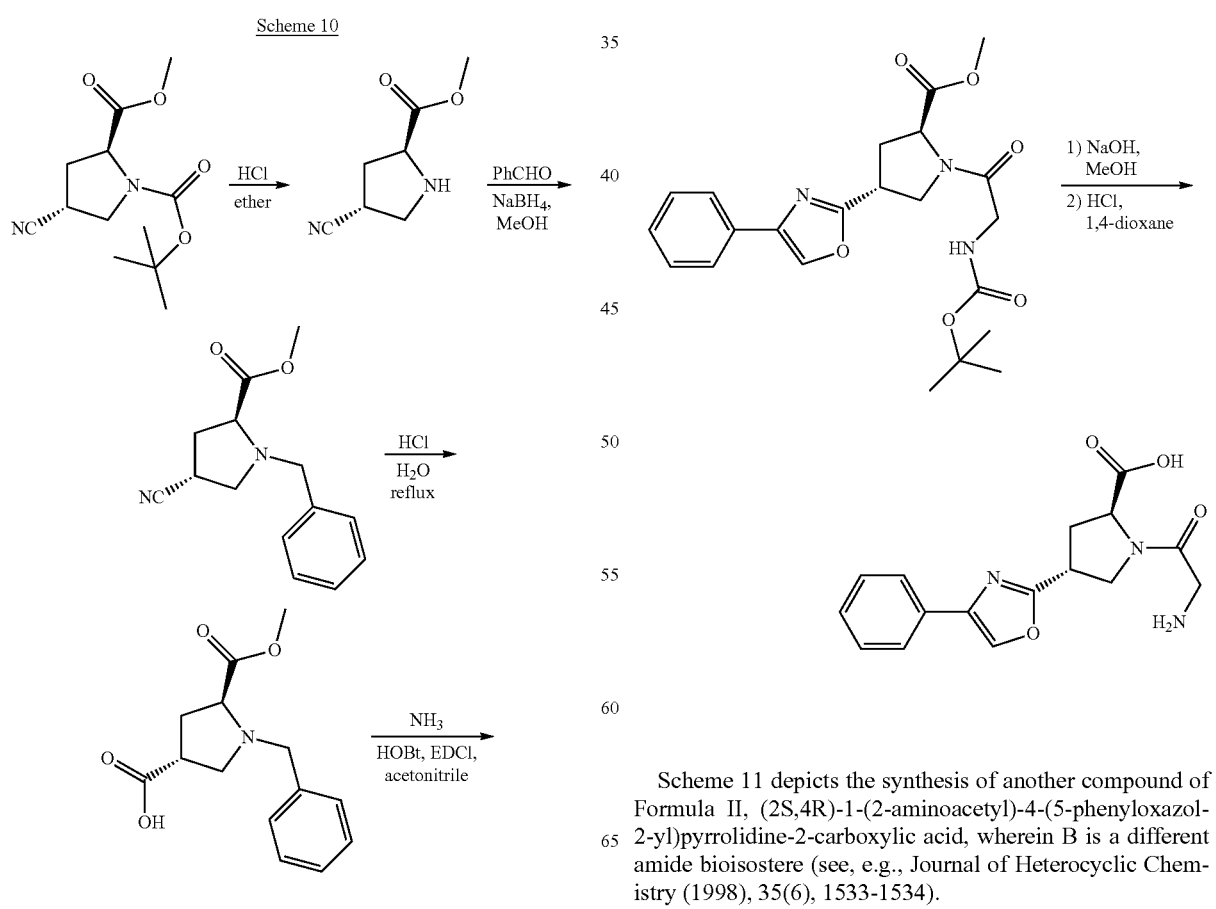

Scheme 11 depicts the synthesis of another compound of Formula II, (2S,4R)-1-(2-aminoacetyl)-4-(5-phenyloxazol-2-yl)pyrrolidine-2-carboxylic acid, wherein B is a different amide bioisostere (see, e.g., Journal of Heterocyclic Chemistry (1998), 35(6), 1533-1534).

Scheme 11
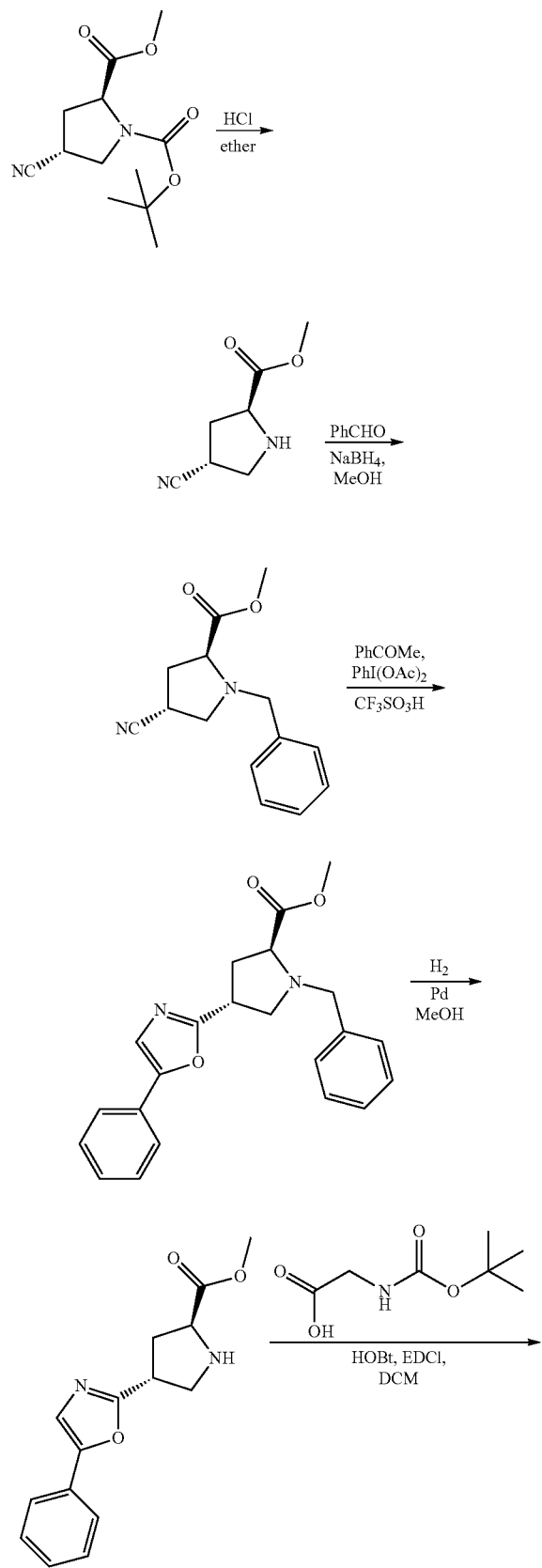
The synthesis of yet another compound of Formula II wherein B is an amide bioisostere, (2S,4R)-1-(2-aminoacetyl)-4-(4-phenyl-1H-imidazol-2-yl)pyrrolidine-2-carboxylic acid, is shown in Scheme 12 (see, e.g., Tetrahedron: Asymmetry, 14(20), 3141-3152; 2003; Journal of Medicinal Chemistry, 44(18), 2990-3000; 2001).
Scheme 12
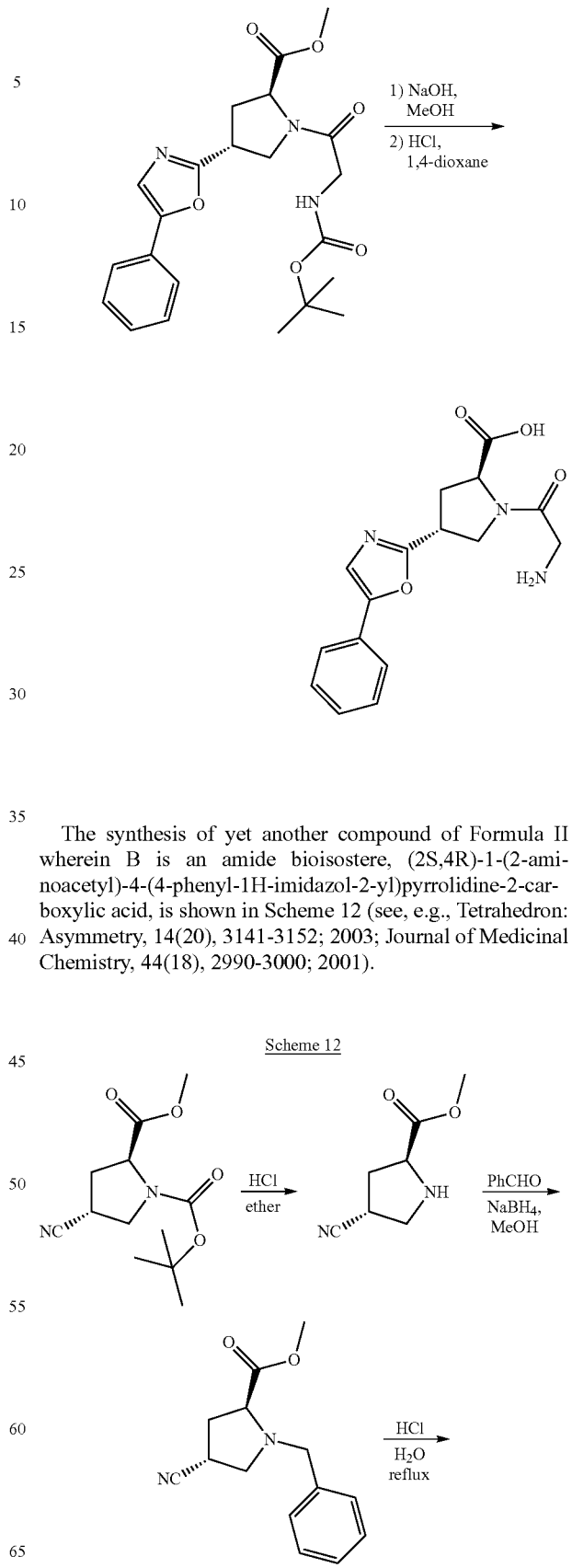

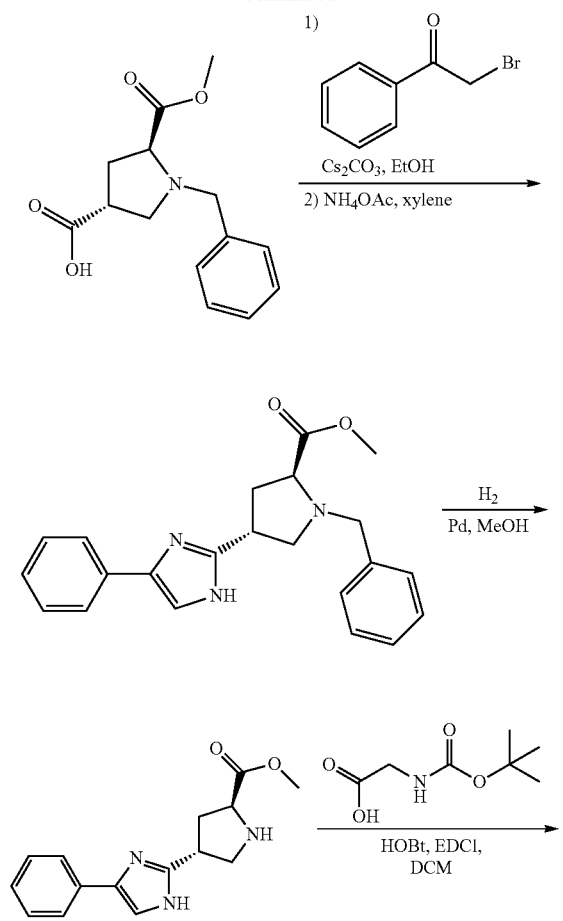
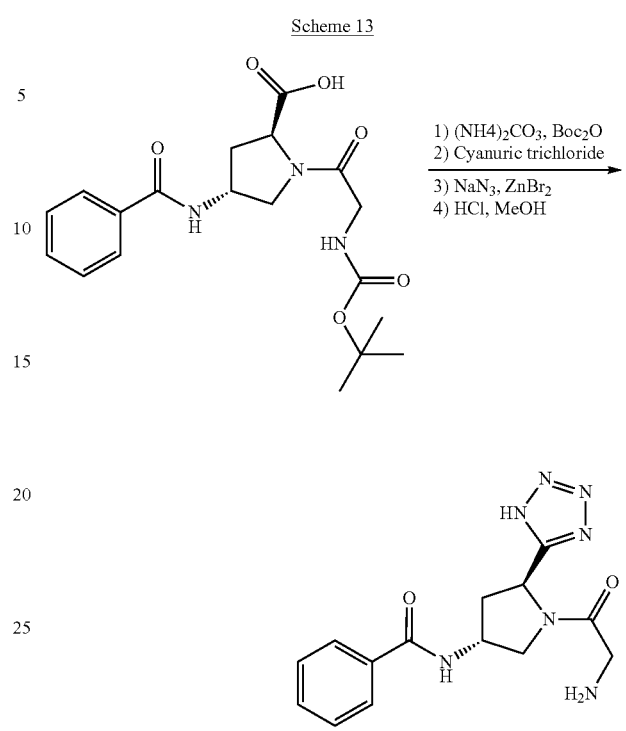
Scheme 14 shows another method by which compounds of Formula II, wherein E is a carboxylic acid bioisostere, can be synthesized (see, e.g., Journal of Medicinal Chemistry, 44(18), 2990-3000; 2001).
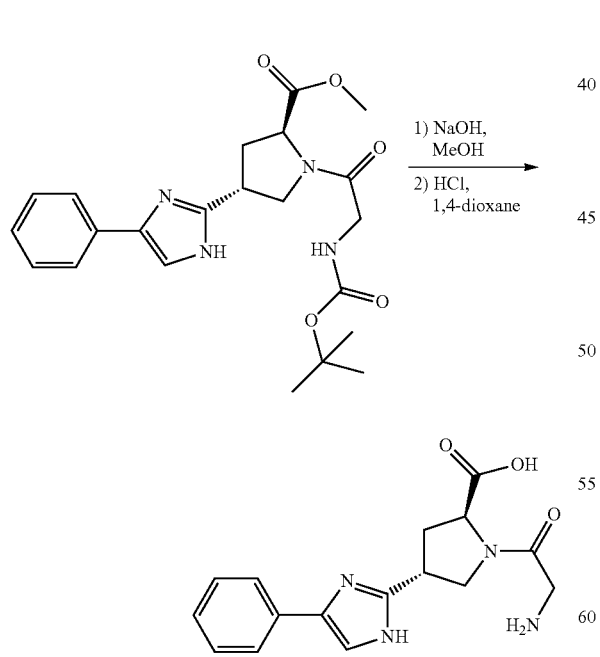
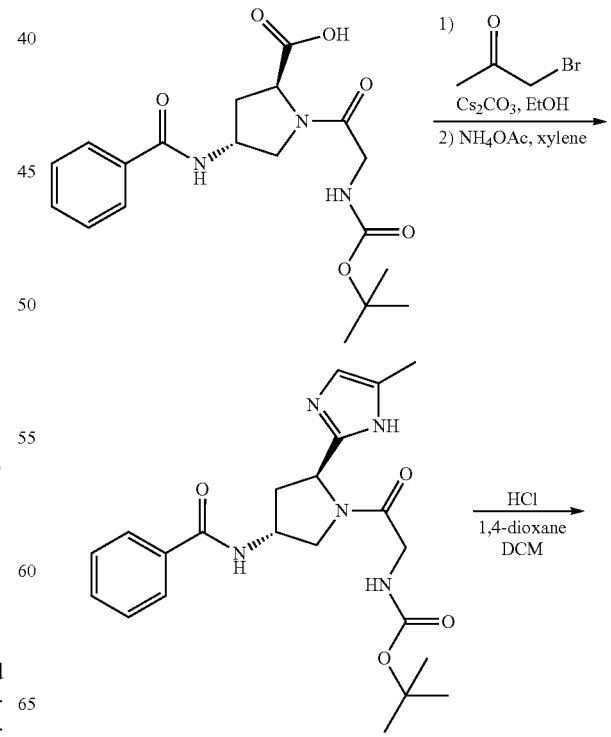
Scheme 13 depicts an exemplary synthesis of a compound of Formula II, N-((3R,5S)-1-(2-aminoacetyl)-5-(1H-tetrazol-5-yl)pyrrolidin-3-yl)benzamide, wherein E is a carboxylic acid bioisostere.

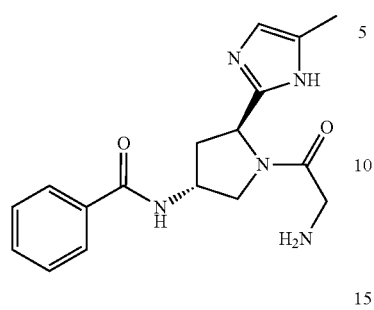

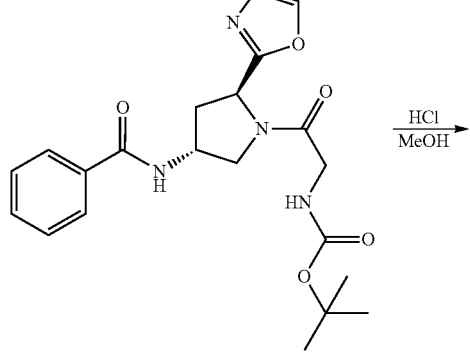

In addition to N-((3R,5S)-1-(2-aminoacetyl)-5-(5-methyl-1H-imidazol-2-yl)pyrrolidin-3-yl)benzamide shown in Scheme 14, compounds of Formula II having different carboxylic acid bioisosteres can be synthesized according to this method by using different bromocarbonyl reagents (e.g., N-((3R,5S)-1-(2-aminoacetyl)-5-(1H-imidazol-2-yl)pyrrolidin-3-yl)benzamide or N-((3R,5S)-1-(2-aminoacetyl)-5-(5-isopropyl-1H-imidazol-2-yl)pyrrolidin-3-yl)benzamide).

Schemes 15-17 depict other exemplary methods for synthesizing compounds of Formula II wherein E is a carboxylic acid bioisostere.

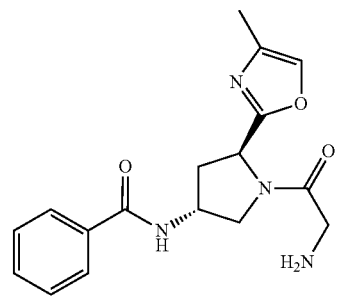

N-((3R,5S)-1-(2-aminoacetyl)-5-(4-methyloxazol-2-yl)pyrrolidin-3-yl)benzamide

Scheme 15

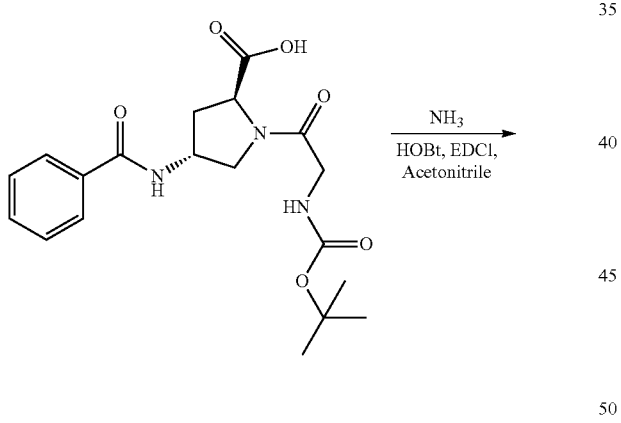

Scheme 16

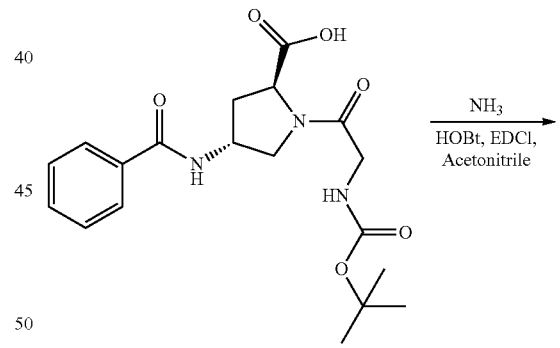

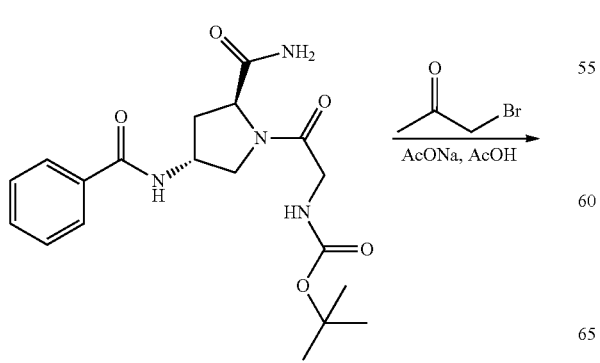

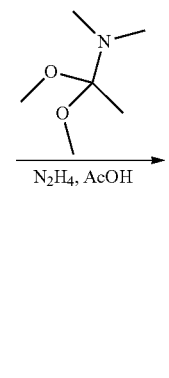

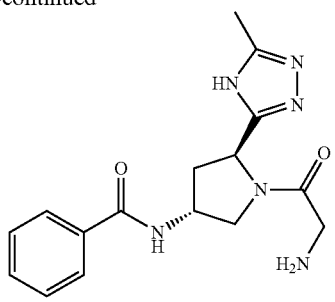

N-((3R,5S)-1-(2-aminoacetyl)-5-(5-methyl-4H-1,2,4-triazol-3-yl)pyrrolidin-3-yl)benzamide Scheme 17

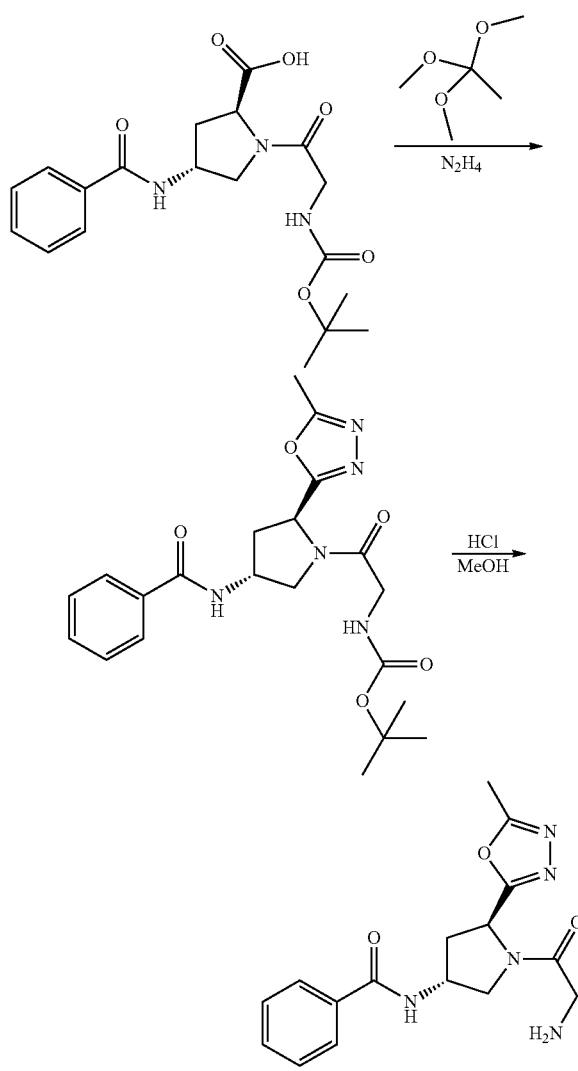

N-((3R,5S)-1-(2-aminoacetyl)-5-(5-methyl-1,3,4-oxadiazol-2-yl)pyrrolidin-3-yl)benzamide In addition to the compounds shown in Schemes 15-17, compounds having different carboxylic bioisosteres can be synthesized according to these methods by varying the reagents. For example different bromide reagents can be used in Scheme 15 (e.g., to produce N-((3R,5S)-1-(2-aminoacetyl)-5-(oxazol-2-yl)pyrrolidin-3-yl)benzamide); different dimethylaminoketals can be used in Scheme 16 (e.g., to produce N-((3R,5S)-1-(2-aminoacetyl)-5-(4H-1,2,4-triazol-3-yl)pyrrolidin-3-yl)benzamide or N-((3R,5S)-1-(2-aminoacetyl)-5-(5-isopropyl-4H-1,2,4-triazol-3-yl)pyrrolidin-3-yl)benzamide); and different ortho esters can be used in Scheme 17 (e.g., to produce N-((3R,5S)-1-(2-aminoacetyl)-5-(1,3,4-oxadiazol-2-yl)pyrrolidin-3-yl)benzamide).

1. General Peptide Synthesis

Compounds of the present teachings can be prepared using the method of synthesis disclosed, for example, in WO 98/11125 (the entire disclosure of which is incorporated by reference herein). Said methods of synthesis will result in a primary peptide or peptide like product having a trifluoroacetate counterion and which can be suitable for the preparation of a medicament. In some instances, however, it can be advantageous to perform a counter ion exchange from trifluoroacetate to a pharmaceutically acceptable or preferred anion (e.g., acetate) by, for example, ion exchange chromatography. Alternatively, the primary peptide or peptide like product can be repeatedly freeze dried and dissolved in diluted hydrochloric acid to obtain the purified hydrochloride.

Apparatus and Synthetic Strategy

When using solid phase methodology, the modified peptides were synthesized batchwise in a polyethylene vessel equipped with a polypropylene filter for filtration using 9-fluorenylmethyloxycarbonyl (Fmoc) and tert.-butyloxycarbonyl (Boc) or otherwise suitable protecting groups for the N-amino and the side chain functionalities such as Allyl, Alloc, Dde, Z etc. When using solution phase techniques, the modified peptides were synthesized using standard equipment throughout the syntheses.

Solvents

Solvent DMF (N,N-dimethylformamide, Riedel de-Häen, Germany) was purified by passing through a column packed with a strong cation exchange resin (Lewatit S100 MB/H strong acid, Bayer AG Leverkusen, Germany) and analyzed for free amines prior to use by addition of 3,4-dihydro-3-hydroxy-4-oxo-1,2,3-benzotriazine (Dhbt-OH) giving rise to a yellow colour (Dhbt-O— anion) if free amines are present. Solvent DCM (dichloromethane, analytical grade, Riedel de-Häen, Germany) was used directly without purification. Acetonitril (HPLC-grade, Lab-Scan, Dublin Ireland) was used directly without purification.

Amino Acids

Fmoc- and Boc-protected amino acids were purchased from Advanced ChemTech (ACT), Bachem and NeoMPS in suitable side-chain protected forms.

Benzoic Acid Derivatives

Benzoic acid derivatives were purchased from Aldrich and used without further purification.

Coupling Reagents

Coupling reagent diisopropylcarbodiimide (DIC) was purchased from (Riedel de-Häen, Germany).

Solid Supports

Peptides were synthesized on TentaGel (e.g. SRam) and Polystyrene (e.g. PAM resin) from Advanced ChemTech and Rapp.

Catalysts and other Reagents

Diisopropylethylamine (DIEA) was purchased from Aldrich, Germany, and ethylenediamine from Fluka, hydrazine, piperidine and pyridine from Riedel-de Häen, Frankfurt, Germany. 4-(N,N-dimethylamino)pyridine (DMAP) was purchased from Fluka, Switzerland and used as a catalyst in coupling reactions involving symmetrical anhydrides. Ethandithiol and Thioanisol were purchased from Riedel-de Häen, Frankfurt, Germany. 3,4-dihydro-3-hydroxy-4-oxo-1,2,3-benzotriazine (Dhbt-OH), 1-hydroxybenzotriazole (HOBt) (HOAt) were obtained from Fluka, Switzerland.

Coupling Procedures

The first amino acid can be coupled as a symmetrical anhydride in DMF generated from the appropriate N-□-protected amino acid and the subsequent amino acids can be coupled as in situ generated HOBt or HOAt esters made from appropriate N-□-protected amino acids and HOBt or HOAt by means of DIC in DMF. The acylations were checked by the ninhydrin test performed at 80° C. in order to prevent Fmoc deprotection during the test (B. D. Larsen, A. Holm, *Int. J. Pept. Protein Res.*, 43, 1-9 (1994)).

Deprotection of the Protecting Group (Fmoc and Fm)

Deprotection of the Fmoc and the Fm group was performed by treatment with 20% piperidine in DMF (1×5 and 1×10 min.), followed by washing with DMF (5×15 ml, 5 min. each) until no yellow colour could be detected after addition of Dhbt-OH to the drained DMF.

Deprotection of the Protecting Group (Boc and tBu)

Deprotection of the Boc and tBu group was performed by treatment with 50% TFA in DCM v/v (2×2 min, 1×30 min) followed by washing with DCM (6×2 min) and then with DMF (2×2 min) treatment with 5% DIEA in DMF v/v (3×2 min) and finally followed by washing with DMF (6×2 min).

Deprotection of the Aloc and Allyl

A solution of 3 eq. $Pd(PPh_3)_4$ dissolved in 15-20 ml $CHCl_3$, AcOH, NMM (37:2:1) was added to the peptid resin. The treatment was continued for three hours at room temperature accompanied by bubbling a stream of $N_2$ through the mixture.

Coupling of Hobt-Esters 3 eq N-α-amino protected amino acid was dissolved in DMF together with 3 eq. HOBt and 3 eq. DIC and then added to the resin.

Preformed Symmetrical Anhydride

Six eq. N-α-amino protected amino acid was dissolved in DCM and cooled to 0° C. DIC (3 eq.) was added and the reaction continued for 10 minutes. The solvent was removed in vacuo and the remainder dissolved in DMF. The solution was immediately added to the resin followed by 0.1 eq. of DMAP.

Cleavage Of the Compound from the Resin Using TFMSA

The Peptidyl-resin was treated with 90% trifluoroacetic acid (TFA, Riedel-de Häen, Frankfurt, Germany) 4% trifluoromethanesulfonic acid (TFMSA, Aldrich) 2% ethandithiol, 4% thioanisol v/v at r.t. for 30-60 minutes. The filtered resin was washed with TFA and filtrates and washings evaporated under reduced pressure. The residue was washed with ether and freeze-dried from trifluoroacetic acid-water. The crude freeze-dried product was analyzed by high-performance liquid chromatography (HPLC) and identified by electrospray ionisation mass spectrometry (ESMS).

Cleavage of the Compound from Resin Using TFA

The Peptidyl-resin was treated with 95% trifluoroacetic acid (TFA, Riedel-de Häen, Frankfurt, Germany)-water v/v or with 95% TFA and 5% ethandithiol v/v at r.t. for 2 hours. The filtered resin was washed with 95% TFA-water and filtrates and washings evaporated under reduced pressure. The residue was washed with ether and freeze-dried from acetic acid-water. The crude freeze-dried product was analyzed by high-performance liquid chromatography (HPLC) and identified by electrospray ionisation mass spectrometry (ESMS).

Preparative HPLC Conditions

Preparative chromatography was carried out using a VISION Workstation (PerSeptive Biosystem) equipped with AFC2000 automatic fraction collector/autosampler. VISION-3 software was used for instrument control and data acquisition.

Column

Kromasil (EKA Chemicals) KR100-10-C8 100 Å, C-8, 10 μm; CER 2230, 250×50.8 mm or a VYDAC 218TP101550, 300 Å, C-18, 10-15 μm, 250×50 mm. The buffer system used included A: 0.1% TFA in MQV; B: 0.085% TFA, 10% MQV, 90% MeCN. Flow rates were 35-40 ml/min and the column temperature was 25° C. UV detection was performed at 215 nm and 280 nm. Suitable gradients were optimized for individual peptides.

Analytical HPLC Conditions

Gradient HPLC analysis was done using a Hewlett Packard HP 1100 HPLC system consisting of a HP 1100 Quaternary Pump, a HP 1100 Autosampler a HP 1100 Column Thermostat and HP 1100 Multiple Wavelength Detector. Hewlett Packard Chemstation for LC software (rev. A.06.01) was used for instrument control and data acquisition. For analytical HPLC, different columns were used as appropriate, such as VYDAC 238TP5415, C-18, 5 μm, 300 Å, or a Jupiter, Phenomenex 00E-4053-E0; 5 μm C-18, 300 Å 150×4.6 mm and others. The buffer system included A: 0.1% TFA in MQV; B: 0.085% TFA, 10% MQV, 90% MeCN. Flow rates were 1 ml/min. The preferred column temperature was 40° C. UV detection was performed at 215 nm. As above, suitable gradients were optimized for the individual peptides.

Mass Spectroscopy

The peptides were dissolved in super gradient methanol (Labscan, Dublin, Ireland), Milli-Q water (Millipore, Bedford, Mass.) and formic acid (Merck, Damstadt, Germany) (50:50:0.1 v/v/v) to give concentrations between 1 and 10 ring/ml. The peptide solutions (20 ml) were analysed in positive polarity mode by ESI-TOF-MS using a LCT mass spectrometer (Micromass, Manchester, UK) accuracy of +/−0.1 m/z.

Solid Phase Synthesis

In all syntheses, dry resin was placed in a polyethylene vessel equipped with a polypropylene filter for filtration. The resin was swelled in DMF. The first amino acid was coupled either as a preformed symmetrical anhydride or as a preactivated HOBt ester as descrbed above. The following amino acid according to the sequence was coupled as a preformed HObt ester as described above. All couplings were continued for at least 2 hours unless otherwise specified. Coupling of the benzoic acid derivative to the side-chain amino functionality on the lysine mimetic amino acid was in all cases performed using a preformed HObt-ester. The final peptide product were cleaved from the solid support and analysed by HPLC and MS as described above.

In all cases the benzoic acid derivative is functionalised as a carboxylic acid and was coupled as an in situ generated HOBt ester by means of DIC in THF.

All couplings were continued for at least 2 hours. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo. The peptide was then cleaved from the resin as described above and freeze-dried.

After purification using preparative HPLC as described above, the peptide product was collected and the identity of the peptide was confirmed by ES-MS.

Exemplary Solution Phase Synthesis

A suitable protected amino acid or a hydroxy- or thiohydroxy acetic acid with a non-protected carboxylic acid (1 eq) is dissolved in DMF together with DIC (1 eq) and HOBt (1 eq). After 1 hour of pre-activation a suitable protected lysine mimetic building block (LM) is added with a non-protected amino group (1.1 eq) together with TEA (1.3 eq) and the mixture is stirred over night at room temperature.

The reaction mixture is evaporated to dryness and the residue is dissolved in ethyl acetate. The ethyl acetate phase is extracted with (1) an aqueous solution of hydrochloric acid (0.1 M) and (2) an aqueous solution of sodium hydroxide (0.1 M) (3) water in order to remove excess of starting material. The organic phase is treated with $MgSO_4$ (dessicated) filtered and evaporated to dryness.

The remaining protected amino group of the LM is deprotected using TFA/DCM if the protecting group is based on tBu, Pd cyclohexen if based on benzyl, piperidine/DCM if based on fluorenyl, hydrazine if based on Dde. After finishing the deprotection reaction (1-2 hours) the reaction mixture is evaporated to dryness. The residue is washed with diethyl ether and dissolved in DMF together with 1.3 eq TEA and finally added to a solution of a substituted benzoic acid (1 eq) that has been preactivated by treatment with DIC (1 eq) and HOBt (1 eq) in DMF. The coupling reaction is continued over night.

The reaction mixture is evaporated to dryness and the residue is dissolved in ethyl acetate. The ethyl acetate phase is extracted with (1) an aqueous solution of hydrochloric acid (0.1 M) and (2) an aqueous solution of sodium hydroxide (0.1 M) (3) water in order to remove excess of starting material. The organic phase is treated with $MgSO_4$ (dessicated) filtered and evaporated to dryness.

The remaining protecting groups are deprotected using TFA/DCM if the protection groups are based on tBu, Pd Cyclohexen if based on Benzyl, Piperidine/DCM if based on Fluorenyl, Hydrazine if based Dde. After finishing the deprotection reaction (1-2 hours) the reaction mixture is evaporated to dryness. The residue is washed with diethyl ether and dissolved in TFA/Water and purified using preparative HPLC. After purification using preparative HPLC as described above, the peptide product was collected and the identity of the peptide was confirmed by ES-MS.

2. Solid Phase Synthesis of Compound 2: (2S4R) 1-(2-Amino-acetyl)-4-benzoylamino-pyrrolidine-2-carboxylic acid PAM-resin (Advanced Chemtech) was swelled in DMF, washed with 5% Triethyl amine (TEA) in DMF and washed with DMF until no yellow color could be detected after adding Dhbt-OH to the drained DMF. (2S4R) Boc-4 Amp (Fmoc)-OH was coupled as symmetrical anhydride as follows.

3 eq (2S4R) Boc-4 Amp(Fmoc)-OH was dissolved in DCM and cooled to 0° C. DIC (1.5 eq.) was added and the reaction continued for 10 minutes. The solvent was removed in vacuo and the residue dissolved in DMF. The solution was immediately added to the resin followed by 0.1 eq. of DMAP. The coupling was continued over night. Excess coupling reagent was removed by washing with DMF. Deprotection of the Fmoc group was performed by treatment with 20% piperidine in DMF (1×5 and 1×10 min.), followed by washing with DMF until no yellow colour could be detected after addition of Dhbt-OH to the drained DMF.

Coupling of benzoic acid was carried out as follows. 3 eq. benzoic acid was dissolved in DMF together with 3 eq. HOBt and 3 eq. DIC and then added to the resin. The coupling was continued over night. Excess coupling reagent was removed by washing with DMF. Prior to the deprotection of the Boc group the resin was treated with DCM. Deprotection of the Boc group was performed by treatment with 50% TFA in DCM v/v (2×2 min, 1×30 min) followed by washing with DCM and then with DMF and then treatment with 5% DIEA in DMF v/v and finally followed by washing with DMF.

Coupling of Boc-Gly-OH was carried out as follows. 3 eq. Boc-Gly-OH was dissolved in DMF together with 3 eq. HOBt and 3 eq. DIC and then added to the resin. The coupling was continued 2 hours. Excess coupling reagent was removed by washing with DMF. The coupling was repeated and continued over night. Before cleavage of the peptide from the solid support the peptide resin was washed with DCM and then with ether and finally dried under vacuum.

Cleavage of the dipeptide from the PAM-Resin was carried out as follows. The peptide-resin was treated with trifluoroacetic acid (TFA, Riedel-de Häen) and after 10 min a volume corresponding to 10% of the TFA total volume of trifluoromethanesulfonic acid (TFMSA, Aldrich) was added at room temperature and the reaction was continued for 2 hours. The filtered resins were washed with TFA. The raw material was precipitated from the TFA-solution by adding diethylether. The raw material was collected as a brown oil. The ether solution was further extracted with water and the water phase was evaporated. The total amount of raw material was purified using prep. HPLC (Vydac C18—column): Buffer A: 0.1% TFA in Water; Buffer B: 90% AcCN; 0.1% TFA; 9.9% Water. Flow: 35 ml/min. Gradient: 0-47 min 100% A to 75% A (Linear). HPLC purity: 99%. MS: calculated M+H=291.12. found M+H=291.7.

3. Solution Phase Synthesis of Compound 2

To a solution of $NaHCO_3$ (58.64 g, 0.698 mol) in water (625 mL) N-BOC-trans-4-amino-L-proline methyl ester hydrochloride (50 g, 0.1745 mol, CNH Technologies, 98%) was added in portions, followed by EtOAc (500 mL). The mixture was cooled to 0° C. A solution of benzoyl chloride (20.26 mL, 0.1745 mol) in EtOAc (100 mL) was added over 25 min at 0° C. The reaction mixture was stirred at 0° C. for 1 h. The phases were separated and the aqueous phase was extracted with 2×200 mL of EtOAc. The combined organic fraction was washed with 200 mL of 1N HCl, 100 mL of saturated $NaHCO_3$ solution, 100 mL of brine, dried over $MgSO_4$, and concentrated to afford 60.67 g of (2S,4R)-1-tert-butyl-2-methyl-4-benzamidopyrrolidine-1,2-dicarboxylate as a heavy oil (99.8% yield; 94% yield adjusted to residual EtOAc). $^1H$ NMR ($CDCl_3$, δ, ppm; for two conformers): 7.78-7.7 (m, 2 H), 7.56-7.4 (m, 3 H), 6.25-6.1 (m, 1 H), 4.8-4.67 (m, 1 H), 4.51-4.41 (m, 0.4 H), 4.34 (dd, J=7, 7 Hz, 0.6 H), 3.97-3.84 (m, 1 H), 3.76 (s, 3H), 3.52 (dd, J=11, 4 Hz, 0.6 H), 3.39 (dd, J=11, 4 Hz, 0.4 H), 2.47-2.21 (m, 2 H), 1.46 (s, 3.6 H), 1.43 (s, 5.4 H). MS (m/z, positive ESI, for M+Na): 371.

(2S,4R)-1-tert-Butyl-2-methyl-4-benzamidopyrrolidine-1,2-dicarboxylate (60.19 g, contains 5.6% EtOAc; 0.1631 mol) was dissolved in $Et_2O$ (100 mL), and the solvent was evaporated under vacuum to remove residual EtOAc. The residual oil was dissolved in $Et_2O$ (100 mL). 2N HCl solution in $Et_2O$ (700 mL) was added (mild exotherm; precipitation commenced after about 5 min). The mixture was stirred at ambient temperature for 21 h. At that point, 200 mL of 2N HCl solution in $Et_2O$ was added, and the mixture was stirred for additional 24 h. The precipitate was filtered, washed with 500 mL of diethyl ether, and dried in vacuum at ambient temperature for 24 h to afford 46.03 g of (2S,4R)-methyl 4-benzamidopyrrolidine-2-carboxylate hydrochloride (99% yield). $^1$H NMR (CD$_3$OD, δ, ppm): 7.91-7.84 (m, 2 H), 7.6-7.44 (m, 3 H), 4.78 (t, J=8.5 Hz, 1 H), 4.69-4.59 (m, 1 H), 3.77 (dd, J=12, 6.6 Hz, 1 H), 3.52 (dd, J=12, 5 Hz, 1 H), 2.67-2.5 (m, 2 H). MS (m/z, positive ESI, for M+H): 249.

To a solution of BOC-Gly-OH (28.13 g, 0.1606 mol) and 1-hydroxybenzotriazole (0.1686 mol, 25.64 g; contains 11.12 wt % H$_2$O) in THF (1.3 L) was added N-(3-dimethylaminopropyl)-N'-ethylcarbodiimide hydrochloride (0.1686 mol, 32.328 g) (Flask A). The mixture was stirred at ambient temperature for 4 h, then the stirring was stopped and the oily residue was allowed to settle. In a separate flask (Flask B), NaOH (0.1606 mol; 32 mL of 5N solution) was added to a suspension of (2S,4R)-methyl 4-benzamidopyrrolidine-2-carboxylate hydrochloride (0.1606 mol, 45.73 g) in THF (0.52 L) over 15 min. The mixture was stirred at ambient temperature for 10 min, during which time the solids mostly dissolved. The solution of HOBt ester prepared in Flask A was added to Flask B at ambient temperature over 15 min, leaving the oily residue behind. The residue in Flask A was washed with 250 mL of THF, and the THF solution was decanted from the heavy oil and added to the mixture in Flask B. The reaction mixture was stirred at ambient temperature for 40 min. Water (500 mL) was added, and the mixture was concentrated under vacuum to remove THF (~550 mL residual volume). EtOAc (500 mL) was added, followed by brine (300 mL). The phases were separated and the aqueous phase was extracted with 2×300 mL of EtOAc. The combined organic fraction was washed with 2×250 mL of 1N HCl, 2×250 mL of sat. NaHCO$_3$ solution, and 150 mL of brine, then dried over MgSO$_4$, and concentrated to afford 48.31 g of (2S,4R) methyl-4-benzamido-1-(2-(tert-butoxycarbonylamino)acetyl)pyrrolidine-2-carboxylate as a foamy solid (74% yield).

$^1$H NMR (CDCl$_3$, δ, ppm; for two conformers): 7.81-7.72 (m, 2 H), 7.57-7.39 (m, 3 H), 6.41 (d, J=6 Hz, 0.8 H), 6.25 (d, J=6 Hz, 0.2 H), 5.32 (br. s, 1 H), 4.88-4.74 (m, 1 H), 4.65 (t, J=7 Hz, 1 H), 4.11-3.86 (m, 2 H), 3.83-3.78 (m, 1 H), 3.76 (s, 3 H), 3.69-3.56 (M, 1 H), 2.65-2.3 (m, 2 H), 1.43 (s, 9 H). MS (m/z, positive ESI, for M+Na): 428.

To a solution of (2S,4R) methyl-4-benzamido-1-(2-(tert-butoxycarbonyl-amino)acetyl)pyrrolidine-2-carboxylate (23.33 g, 0.0575 mol) in methanol (450 mL) was added NaOH (0.2875 mol, 144 mL of 2N aqueous solution) at −1 to 1° C. over 15 min. The mixture was stirred at −5 to −1° C. for 2.5 h. HCl (0.2875 mol, 144 mL of 2N aqueous solution) was added at −3 to 1° C. over 25 min. MeOH was distilled off under vacuum, then 500 mL of EtOAc was added. The aqueous phase was saturated with NaCl and the phases were separated. The aqueous phase was extracted with 2×250 mL EtOAc and the combined EtOAc solution was dried over MgSO$_4$, and concentrated to afford 22.54 g of (2S,4R) 4-benzamido-1-(2-(tert-butoxycarbonylamino)acetyl)pyrrolidine-2-carboxylic acid as a white foamy solid (contains 6.6 wt % EtOAc; 94% yield adjusted to residual EtOAc). $^1$H NMR (CD$_3$OD, δ, ppm): 7.87-7.79 (m, 2 H), 7.58-7.42 (m, 3 H), 4.81-4.7 (m 1 H), 4.69-4.56 (m, 1 H), 4.05-3.72 (m, 3 H), 3.67-3.49 (m, 1 H), 2.64-2.28 (m, 2 H), 1.43 (s, 9 H). MS (m/z, positive ESI) for M+H: 392; for M+Na: 414.

(2S,4R) 4-Benzamido-1-(2-(tert-butoxycarbonylamino)acetyl)pyrrolidine-2-carboxylic acid (21.97 g; contains 6.6 wt % EtOAc; 0.0524 mol, adjusted to residual EtOAc) was dissolved in dioxane (100 mL). The solvent was evaporated under vacuum to remove residual EtOAc. The residue was dissolved in anhydrous dioxane (200 mL) and HCl (100 mL of freshly prepared ~3.6 N solution in dioxane) was added at 10-12° C. The solution was allowed to warm to ambient temperature (precipitation commenced after about 2 min). The reaction mixture was stirred at ambient temperature for 21 h, at which time 30 mL of ~3.6N HCl solution was added, and the mixture was stirred for additional 5.5 h. Precipitated solids were filtered using N$_2$ pressure, washed with 4×25 mL of dioxane, and dried under vacuum at room temperature for 24 h to afford 18.7 g of crude product as white solid. The crude product was dissolved in i-PrOH (104 mL) and 210 mL of diethyl ether was added over 1 h (precipitate formed immediately upon ether addition). The mixture was stirred for 1 h, filtered using N$_2$ pressure, washed with 2×50 mL of 3:1 Et$_2$O-i-PrOH solution, and dried under vacuum at room temperature for 24 h and at 40° C. for 48 h to afford 15.7 g of (2S,4R)-1-(2-aminoacetyl)-4-benzamidopyrrolidine-2-carboxylic acid hydrochloride. $^1$H NMR (DMSO-d6, δ, ppm, for two conformers): 8.77 (d, J=7 Hz, 0.8 H), 8.71 (d, J=7 Hz, 0.2 H), 8.68-7.95 (br, 2 H), 7.92-7.83 (m, 2 H), 7.59-7.43 (m, 3 H), 4.87-4.79 (m, 0.2 H), 4.68-4.54 (m, 0.8 H), 4.54-4.44 (m, 1 H), 4.0-3.47 (m, 4 H), 2.47-2.12 (m, 2 H). HRMS calc. for C$_{14}$H$_{18}$N$_3$O$_4$ (M+H): 292.1297. found: 292.1294.

4. Synthesis of Compounds 64-68 and 70-78

(2S,4R)-4-benzamido-1-(2-(tert-butoxycarbonylamino)acetyl)pyrrolidine-2-carboxylic acid (0.05 g, 0.1 mmol), 1-hydroxybenzotriazole monohydrate (Aldrich, 0.021 g, 0.15 mmol, 1.2 equivalents) and 1-(3,3-dimethylaminopropyl)-3-ethylcarbodiimide hydrochloride (Aldrich, 0.029 g, 0.15 mmol, 1.2 equivalents) were dissolved in acetonitrile (15 mL) under nitrogen atmosphere with ice cooling. The temperature was gradually increased to room temperature over 2 hour time period, and the mixture was then stirred at room temperature overnight. The reaction solution was again cooled to 0° C., 25-30% aqueous solution of the corresponding amine (prepared from a pure reagent obtained from Aldrich) (0.1 mL) was added, and stirring was continued with cooling for 30 minutes and then at room temperature for 2 hours. Acetonirile (5 mL) was added to the reaction mixture, and the volatiles were removed in vacuo. The semi-solid residue was purified by silica-gel (EMD, 0.040-0.063 mm) chromatography (developing solvent: 3-5% gradient methanol-dichloromethane) to afford the corresponding amides in 80-87% yield.

The product from the previous step was dissolved in dry dichloromethane (10 mL) under nitrogen atmosphere and 1 M ethereal solution of hydrochloric acid (Aldrich) (1 mL) was added while keeping the temperature below 30° C. The reaction mixture was stirred overnight under nitrogen atmosphere. The precipitate was filtered, washed with dichloromethane (2 mL) and diethyl ether (2 mL) and dried under high vacuum to afford a hydrochloride salt of corresponding compounds 64-68 and 70-78 in 75-84% yield and at least 98% purity.

5. Synthesis of Compound 80: (2S,4R)-1-(2-acetamidoacetyl)-4-benzamidopyrrolidine-2-carboxylic acid To a solution of (2S4R) 1-(2-Amino-acetyl)-4-benzoylamino-pyrrolidine-2-carboxylic acid (0.05 g, 0.17 mmol) and triethylamine (Aldrich) (0.19 mL, 1.37 mmol, 8 equivalents) in acetone (3 mL) was slowly added acetic anhydride (0.13 mL, 1.37 mmol, 8 equivalents) with stirring at room temperature under nitrogen atmosphere. The mixture was stirred for 3 hours while monitored by LCMS. Upon completion, the volatiles were removed in vacuo and the residue was purified by preparative HPLC (column: Xterra MSC18 50×250 mm, 10 u) using 40/60 to 90/10 methanol/water gradient (0.1% formic acid in methanol and 0.1 formic acid in water) to afford 0.020 g (35% yield) of the desired product as white solid with limited solubility in organic solvents.

6. Synthesis of Compound 81: (2S,4R)-4-benzamido-1-(2-(methylamino)acetyl) pyrrolidine-2-carboxylic acid To a solution of (2S,4R)-methyl 4-benzamidopyrrolidine-2-carboxylate (intermediate in the synthesis of Compound 2) (0.05 g, 0.20 mmol), 1-(3,3-dimethylaminopropyl)-3-ethyl-carbodiimide hydrochloride (Aldrich) (0.043 g, 0.22 mmol, 1.1 equivalents), 1-hydroxybenzotriazole monohydrate (Aldrich) (0.030 g, 0.22 mmol, 1.1 equivalents) and 2-(tert-butoxycarbonyl(methyl)amino)acetic acid (Aldrich) (0.038 g, 0.20 mmol) in anhydrous dichloromethane (10 mL) was added N-methylmorpholine (0.05 mL) under nitrogen atmosphere at 0° C. The reaction mixture was allowed to warm to room temperature during 2 hour time period and stirred overnight at ambient temperature. The volitiles were removed in vacuo and the residue was purified by silica-gel (EMD, 0.040-0.063 mm) chromatography (developing solvent: 3-5% gradient methanol/dichloromethane) to afford 0.064 g (75% yield) of the coupling product (2S,4R)-methyl 4-benzamido-1-(2-(tert-butoxycarbonyl(methyl)amino)acetyl) pyrrolidine-2-carboxylate.

To a solution of the abovementioned amide (0.064 g, 0.15 mmol) in methanol (5 mL) was added 2N aqueous solution of sodium hydroxide (0.38 mL, 0.75 mmol, 5 equivalents) at 0° C. under nitrogen atmosphere over 5 minutes. The reaction was monitored by LCMS and was finished in 2 hours. 2N aqueous hydrochloric acid (Aldrich) (0.38 mL, 0.75 mmol, 5 equivalents) was added at 0° C. over 5 min. Methanol was distilled off under vacuum. Ethyl acetate (10 mL) and water (1 mL) were added. The aqueous phase was saturated with sodium chloride and the phases were separated. The aqueous phase was extracted with ethyl acetate (2×10 mL). The combined organic fractions were dried over magnesium sulfate and concentrated to afford a white foamy product (2S,4R)-4-benzamido-1-(2-(tert-butoxycarbonyl (methyl)amino) acetyl)pyrrolidine-2-carboxylic acid that was used in the next step without purification.

The acid from the previous step was dissolved in dry dichloromethane (10 mL) under nitrogen atmosphere and 1 M ethereal solution of hydrochloric acid (Aldrich) (1 mL) was added while keeping the temperature below 30° C. The reaction mixture was stirred overnight under nitrogen atmosphere. The formed precipitate was filtered, washed with dichloromethane (2 mL), diethyl ether (2 mL) and dried under high vacuum. The product was further purified by preparative HPLC (column: Xterra MSC18 19×150 mm) using 5% to 95% methanol/water gradient (0.1% formic acid in methanol and 0.1% formic acid in water) to afford 0.026 g (38% over 3 steps) of the desired product.

7. Synthesis of Compound 82: (2S,4R)-4-benzamido-1-(2-(2,2,2-trifluoroacetamido)acetyl)pyrrolidine-2-carboxylic acid To a solution of (2S4R) 1-(2-Amino-acetyl)-4-benzoylamino-pyrrolidine-2-carboxylic acid (Compound 2, 0.05 g, 0.17 mmol) and triethylamine (Aldrich) (0.048 mL, 0.34 mmol, 2 equivalents) in acetone (3 mL) was added slowly trifluoroacetic anhydride (0.024 mL, 0.17 mmol) with stirring at room temperature under nitrogen atmosphere. The mixture was stirred for 1.5 hours with careful monitoring by LCMS. Upon completion, the volatiles were removed in vacuo and the residue was purified by preparative HPLC (column: Xterra MSC18 50×250 mm, 10 u) using 5% to 90% methanol/water gradient (0.1% formic acid in methanol and 0.1% formic acid in water) to afford 0.012 g (18% yield) of the desired product.

8. Synthesis of Compound 84: (2S,4R)-4-benzamido-1-(2-(dimethylamino) acetyl)pyrrolidine-2-carboxylic acid To a solution of (2S4R) 1-(2-Amino-acetyl)-4-benzoylamino-pyrrolidine-2-carboxylic acid (Compound 2, 0.05 g, 0.17 mmol) in methanol (3 mL) at room temperature was added 37% aqueous formaldehyde (Aldrich) (0.1 mL). The resulting mixture was stirred at this temperature for 3 hours, then cooled to 0° C., and sodium cyanoborohydride (Aldrich) (0.043 g, 0.69 mmol, 4 equivalents) was added portion-wise over 5 minutes. After stirring for 1 hour at room temperature, the solvent was removed in vacuo and the solid residue was purified by preparative HPLC (column: XTerra MS C18, 5 u, 19×150 mm) using 5% to 95% methanol/water gradient (0.1% formic acid in methanol and 0.1% formic acid in water) to afford 0.017 g (31% yield) of the desired product.

9. Synthesis of Compound 85: (2S,4R)-4-benzamido-1-(2-formamidoacetyl) pyrrolidine-2-carboxylic acid Acetic anhydride (Acros) (0.32 mL, 3.4 mmol, 10 equivalents) was added dropwise to a solution of (2S4R) 1-(2-Amino-acetyl)-4-benzoylamino-pyrrolidine-2-carboxylic acid (Compound 2, 0.1 g, 0.34 mmol, 1 equivalent) in formic acid (J. T. Baker) (1 mL) at 0° C. After the addition was complete, the reaction mixture was allowed to warm to room temperature and stirred an additional 24 hours. The reaction mixture was monitored by TLC and LCMS. An additional amount of acetic anhydride (0.32 mL, 3.4 mmol, 10 equivalents) was added and the reaction mixture stirred for 24 hours at room temperature. Ice-water (1 mL) was added and the volatiles were removed in vacuo to yield an oily crude product that was further purified by HPLC (column: Waters Atlantis 19×150 mm) using 0.1% formic acid in H2O/MeOH 20-40% MeOH over 15 minute gradient to afford 0.031 g (29%) of the desired product.

The general procedures outlined above were used for the synthesis of the exemplary compounds listed in Table 1.

TABLE 1

| Compound | Name | MH+ found | MH+ calculated | HPLC purity | Yield % |
| --- | --- | --- | --- | --- | --- |
| 1 | (2S4R) 1-(2-Amino-acetyl)-4-(4-nitro-benzoylamino)-pyrrolidine-2-carboxylic acid | 336.17 | 336.11 | 89 | 18 |
| 3 | (2S4R) 1-(2-Amino-acetyl)-4-(4-methyl-benzoylamino)-pyrrolidine-2-carboxylic acid | 305.2 | 305.14 | 87 | 28 |

TABLE 1-continued

| Compound | Name | MH+ found | MH+ calculated | HPLC purity | Yield % |
|---|---|---|---|---|---|
| 4 | (2S4R) 1-(2-Amino-acetyl)-4-(4-methoxy-benzoylamino)-pyrrolidine-2-carboxylic acid | 321.18 | 321.13 | 95 | 37 |
| 6 | (2S4R)1-(2-Amino-4-carboxy-butyryl)-4-benzoylamino-pyrrolidine-2-carboxylic acid | 363.16 | 363.14 | 97 | 18 |
| 11 | (2S4S) 1-(2-Amino-acetyl)-4-(4-methoxy-benzoylamino)-pyrrolidine-2-carboxylic acid | 321.05 | 321.13 | 99 | 35 |
| 12 | (2S4S) 1-(2-Amino-acetyl)-4-(4-methyl-benzoylamino)-pyrrolidine-2-carboxylic acid | 305.27 | 305.14 | 99 | 37 |
| 13 | (2S4S) 1-(2-Amino-acetyl)-4-(4-nitro-benzoylamino)-pyrrolidine-2-carboxylic acid | 336.18 | 336.11 | 99 | 40 |
| 14 | (2S4S) 1-(2-Amino-acetyl)-4-(benzoylamino)-pyrrolidine-2-carboxylic acid | 291.29 | 291.12 | 99 | 15 |
| 24 | 3-(2-Amino-acetylamino)-5-(4-methyl-benzoylamino)-benzoic acid | 327.22 | 327.12 | 99 | 25 |
| 26 | 3-(2-Amino-acetylamino)-5-benzoylamino-benzoic acid | 313.13 | 313.11 | 99 | 10 |
| 28 | (2S4R) {[4-(4-Nitro-benzoylamino)-pyrrolidine-2-carbonyl]-amino}-acetic acid | 336.19 | 336.11 | 97 | 39 |
| 29 | (2S4R) {[4-(4-Methoxy-benzoylamino)-pyrrolidine-2-carbonyl]-amino}-acetic acid | 321.29 | 321.13 | 97 | 30 |
| 30 | (2S4R)2-{[4-(4-Methyl-benzoylamino)-pyrrolidine-2-carbonyl]-amino}-acetic acid | 305.28 | 305.14 | 98 | 28 |
| 35 | (2S4S) {[4-(benzoylamino)-pyrrolidine-2-carbonyl]-amino}-acetic acid | 291.29 | 291.12 | 95 | 24 |
| 36 | (2S4S) {[4-(4-Methoxy-benzoylamino)-pyrrolidine-2-carbonyl]-amino}-acetic acid | 321.35 | 321.13 | 97 | 33 |
| 37 | (2S4S) {[4-(4-Nitro-benzoylamino)-pyrrolidine-2-carbonyl]-amino}-acetic acid | 336.09 | 336.11 | 92 | 37 |
| 38 | (2S4S) {[4-(4-Methyl-benzoylamino)-pyrrolidine-2-carbonyl]-amino}-acetic acid | 305.29 | 305.14 | 95 | 41 |
| 39 | [2-Amino-3-(4-benzoylamino-phenyl)-acetylamino]-acetic acid | 341.22 | 341.14 | 98 | 20 |
| 40 | {2-Amino-3-[4-(4-methoxy-benzoylamino)-phenyl]-acetylamino}-acetic acid | 371.28 | 371.15 | 93 | 56 |
| 41 | {2-Amino-3-[4-(4-Nitro-benzoylamino)-phenyl]-acetylamino}-acetic acid | 386.28 | 386.12 | 93 | 45 |
| 42 | {2-Amino-3-[4-(4-methyl benzoylamino)-phenyl]-acetylamino}-acetic acid | 355.25 | 355.15 | 77 | 40 |
| 43 | [(1-Benzoyl-imidazolidine-2-carbonyl)-amino]-acetic acid | 277.17 | 277.11 | 90 | 22 |
| 44 | {[1-(4-nitro-benzoyl)-imidazolidine-2-carbonyl]-amino}-acetic acid | 322.15 | 322.09 | 95 | 24 |
| 48 | (3-Amino-5-benzoylamino-benzoylamino)-acetic acid | 313.33 | 313.11 | 98 | 22 |
| 49 | (3-Amino-5-(4-methoxy-benzoylamino)-benzoylamino)-acetic acid | 343.29 | 343.12 | 89 | 45 |
| 50 | (3-Amino-5-(4-methyl-benzoylamino)-benzoylamino)-acetic acid | 327.21 | 327.12 | 96 | 40 |
| 51 | (3,5-di-Amino-benzoylamino)-acetic acid | 209.11 | 209.08 | 98 | 51 |
| 52 | (2S4R)4-Benzoylamino-1-(2-hydroxy-acetyl)-pyrrolidine-2-carboxylic acid | 292.15 | 292.29 | 93 | 25 |
| 54 | 3-Benzoylamino-5-(2-hydroxy-acetylamino)-benzoic acid | 314.10 | 314.09 | 96 | 12 |
| 56 | 1-Benzoyl-3-(2-hydroxy-acetyl)-imidazolidine-2-carboxylic acid amide | 278.12 | 278.09 | 95 | 17 |

TABLE 1-continued

| Compound | Name | MH+ found | MH+ calculated | HPLC purity | Yield % |
|---|---|---|---|---|---|
| 64 | (2S,4R) 1-(2-aminoacetyl)-4-benzamidopyrrolidine-2-carboxamide | 291 | 291.1 | 98 | 77 |
| 65 | (2S,4R) 1-(2-aminoacetyl)-4-benzamido-N-methylpyrrolidine-2-carboxamide | 305 | 305.1 | >99 | 82 |
| 66 | (2S,4R) 1-(2-aminoacetyl)-4-benzamido-N-ethylpyrrolidine-2-carboxamide | 317.1 | 318.1 | >99 | 76 |
| 67 | (2S,4R) 1-(2-aminoacetyl)-4-benzamido-N-isopropylpyrrolidine-2-carboxamide | 333.2 | 333.2 | >99 | 81 |
| 68 | (2S,4R) 1-(2-aminoacetyl)-4-benzamido-N-cyclopropylpyrrolidine-2-carboxamide | 331.3 | 331.2 | 99 | 84 |
| 69 | (2S,4R) 4-benzamido-1-(2-(tert-butoxycarbonylamino)acetyl)pyrrolidine-2-carboxamide | 391 | 391.2 | >99 | 80 |
| 70 | (2S,4R) 1-(2-aminoacetyl)-4-benzamido-N-(pentan-3-yl)pyrrolidine-2-carboxamide | 361.1 | 361.2 | >99 | 81 |
| 71 | (2S,4R) 1-(2-aminoacetyl)-4-benzamido-N-cyclopentylpyrrolidine-2-carboxamide | 359 | 359.2 | 99 | 81 |
| 72 | (2S,4R) 1-(2-aminoacetyl)-4-benzamido-N-isobutylpyrrolidine-2-carboxamide | 347 | 347.2 | 99 | 79 |
| 73 | (2S,4R) 1-(2-aminoacetyl)-4-benzamido-N-cyclobutylpyrrolidine-2-carboxamide | 345 | 345.2 | >99 | 78 |
| 74 | (2S,4R) 1-(2-aminoacetyl)-4-benzamido-N-tert-butylpyrrolidine-2-carboxamide | 346.9 | 347.2 | >99 | 83 |
| 75 | (2S,4R) 1-(2-aminoacetyl)-4-benzamido-N-(tetrahydro-2H-pyran-4-yl)pyrrolidine-2-carboxamide | 374.9 | 375.2 | >99 | 75 |
| 76 | (2S,4R) 1-(2-aminoacetyl)-4-benzamido-N-((R)-3-methylbutan-2-yl)pyrrolidine-2-carboxamide | 361 | 361.2 | 99 | 80 |
| 77 | (2S,4R) 1-(2-aminoacetyl)-4-benzamido-N-((R)-3,3-dimethylbutan-2-yl)pyrrolidine-2-carboxamide | 374.9 | 375.2 | 99 | 83 |
| 78 | (2S,4R) 1-(2-aminoacetyl)-4-benzamido-N-phenylpyrrolidine-2-carboxamide | 367.2 | 366.9 | 99 | 82 |
| 79 | (2S,4R) 1-(2-aminoacetyl)-4-benzamido-N-((R)-tetrahydrofuran-3-yl)pyrrolidine-2-carboxamide | 360.3 | 360.2 | >99 | 13 |
| 80 | (2S,4R) 1-(2-acetamidoacetyl)-4-benzamidopyrrolidine-2-carboxylic acid | 334.1 | 334.1 | >99 | 35 |
| 81 | (2S,4R) 4-benzamido-1-(2-(methylamino)acetyl)-pyrrolidine-2-carboxylic acid | 306.2 | 306.1 | >99 | 38 |
| 82 | (2S,4R) 4-benzamido-1-(2-(2,2,2-trifluoroacetamido)acetyl)pyrrolidine-2-carboxylic acid | 388 | 388.1 | >99 | 18 |
| 83 | (2S,4R) 4-benzamido-1-(2-(tert-butoxycarbonylamino)acetyl)pyrrolidine-2-carboxylic acid | 392.3 | 392.2 | >99 | 30 |
| 84 | (2S,4R) 4-benzamido-1-(2-(dimethylamino)acetyl)pyrrolidine-2-carboxylic acid | 320 | 320.1 | >99 | 31 |
| 85 | (2S,4R) 4-benzamido-1-(2-formamidoacetyl)pyrrolidine-2-carboxylic acid | 320.1 | 320.1 | >99 | 29 |

G. Biological Assay Data

1. Effect of the Compounds on Calcium Induced Arrhythmias

The anti-arrhythmic effect of compounds according to the present teachings was tested in a model of calcium-induced arrhythmias according to the model of Lynch et al., *J. Cardiovasc. Pharmacol.* (1981), 3: 49-60. Male CD-1 mice were anaesthetized with Ketamine (75 mg/kg) and medetomidine (1 mg/kg) IP. An i.v. cannula was inserted into the tail vein. A lead II ECG signal was recorded continuously by positioning stainless steel ECG electrodes on the right forelimb and left forelimb. The ground electrode was placed on the right hind limb. The signal was amplified and filtered using Gould physiograph components and po-ne-mah data acquisition software. After a 90 sec equilibration period test compound was injected into the tail vein (over 30 seconds). Mice pre-treated with vehicle (0.9% saline) were tested as control animals. The injection volume was 100 µl/30 g mice in all experiments. Infusion of $CaCl_2$ (30 mg/mL, 0.1 mL/min/30 g mice, 100 mg/kg/min) was started 3 min after IV administration of drug or vehicle. The time lag to onset of cardiac conduction block was determined as the time from the start of $CaCl_2$ infusion until the first arrhythmic event occurred. The first conduction block was defined as the first RR-interval, larger/or equal to, 3 times one RR-interval from the pre-treatment period. The first arrhythmic event occurring was either a second degree AV-block (intermittent failure of the AV conduction characterized by a P-wave without the concomitant QRS complex) or a second degree SA block (prolonged RR-interval and a QRS-complex without a preceding P-wave).

Mice pre-treated with vehicle (0.9% saline) were tested on all days as a measure for control level in untreated animal. Injection volume was 100 µL in all experiments. The time lag to onset of arrhythmias was determined as the time from the start of $CaCl_2$ infusion until the first event of conduction block defined as intermittent failure of the SA or AV conduction characterized by delayed P-wave activation (SA block) or by a P-wave without the concomitant QRS complex (AV block). The time lag to onset of AV block is given below in Table 2.

TABLE 2

| Compound | Time to AV block (sec.) |
|---|---|
| Saline (control) | 62-78 |
| 2 | 134.7 |
| 6 | 117.9 |
| 26 | 122.8 |
| 52 | 135.6 |
| 54 | 121.7 |
| 56 | 128.1 |
| 64 | 111.7 |
| 65 | 115.2 |
| 66 | 122.7 |
| 67 | 134.4 |
| 68 | 143.8 |
| 80 | 111.5 |
| 81 | 123.2 |
| 82 | 113.8 |
| 83 | 110.9 |
| 84 | 108.8 |

It follows from the data presented in Table 2 that pre-treatment of a mouse with a range of compounds of the present teachings resulted in a consistent increase in the time to an AV block in the mouse after infusion of $CaCl_2$. Compounds of the present teachings thus exhibit anti-arrhythmic properties.

2. Effect of the Compounds on Metabolic Stress Induced Atrial Conduction Slowing The ability to maintain conduction during metabolic stress was tested in an in vitro model as described by Haugan et al (*J. Cardiovasc. Electrophysiol.*, 2005:16:537-545). Rats (300-400 g) were killed by a sharp blow on the neck. The heart was rapidly excised and transferred to a small dish containing 37° oxygenated modified Tyrodes buffer containing (in mM): NaCl 136, KCl 4, $MgCl_2$ 0.8, $CaCl_2$ 1.8 HEPES 5, MES 5, Glucose 6, pH 7.3. The left atrium was carefully dissected and a tissue sample of approximately 2×6 mm was taken from the left atrial appendage and placed in a tissue chamber (volume 5 ml), (Steiert Organ Bath, Hugo Sach Electronic, Germany). The chamber was perfused throughout the study with 37° C. Tyrodes buffer at a rate of 10 ml/min.

A bipolar stimulation electrode (Teflon coated stainless steel, diameter 75 NM) was placed at one end of the tissue. Stimulation was performed at 1 Hz using rectangular pulses at double threshold (duration of stimulus 0.2 ms) delivered by a stimulator (Hugo Sachs, Type 215) through an isolation unit (Universal Isolated Stimulator Unit type 263, Hugo Sachs, Germany).

Two separate microelectrodes of pure iridium (World Precision Instruments, tip-impedance 3.5-4.0 MΩ) were placed on a line along the long-axis of the preparation for recording of atrial CV. The distances from the stimulating electrode to the first and second microelectrode is 1.5-2.0 mm and 3.0-4.0 mm, respectively. Each microelectrode was connected to a head-stage preamplifier (10× amplification of the signals). The preamplifiers were connected to a bio potential amplifier module that was connected to the data acquisition system through a Hugo Sachs PLUGSYS. Signals were filtered at 1 kHz and sampled at 10 kHz.

Following a 30 minute equilibration period, pacing at 1 Hz was initiated. During the first 20 minute recording period (baseline period), the chamber was perfused with 37° C. oxygenated Tyrodes buffer, pH 7.3. Then the test sample (Compound 2) or control was added to the perfusion buffer for another 20 minute period (pre-treatment period). Following the 20 minutes of pretreatment, perfusion was changed to a 37° C. glucose-free, non-oxygenated Tyrodes buffer, pH 7.3 (with or without compounds of interest) for 40 minutes (metabolic stress period). The results of these experiments are shown graphically in FIG. 1.

Referring to FIG. 1, in preparations containing the control, conduction velocity decreased by 22%. In contrast, in preparations treated with Compound 2, atrial conduction velocity did not change compared to baseline.

It follows from the data presented in FIG. 1 that pre-treatment of an isolated rat atrial strip with a compound of the present teachings significantly prevented metabolic stress induced cardiac conduction slowing. Cardiac diseases such as atrial fibrillation, atrial flutter, ventricular tachycardia and ventricular fibrillation are all characterized by the presence of abnormal cardiac conduction slowing. Thus, through the effect on cardiac conduction, compounds of the present teachings are expected to exert anti-arrhythmic effects.

3. Plasma Stability Assay

To predict its plasma stability, compounds of the present teachings were incubated in male rat plasma (1:1 plasma:pH 7.4 buffer) at 1 µM concentration at 37° C. After 3 hours, the reaction was quenched with cold acetonitrile. The solution was centrifuged and the supernatant was analyzed with LC-MS using the following HPLC conditions: Thermo Hypersil-Keystone Aquasil C18 column (50 mm×2.1 mm, 5 µM) at ambient temperature; Solvent A: 0.1% formic acid in water; Solvent B: 0.1% formic acid in acetonitrile; solvent gradient: 100% A to 50% A over 2.5 min, to 10% A over 1.5 min, and returning to 100% A and re-equilibrating for 1.5 min; flow-rate: 0.8 mL/min. The percent of the compound remaining was calculated by dividing the 3-hour incubation sample LC-MS signal area counts by the time=0 area counts. The results of these experiments are summarized in Table 3 below.

TABLE 3

| Compound | % Remaining |
|---|---|
| 2 | 93 |
| 64 | 27 |
| 65 | 87 |
| 66 | 100 |

TABLE 3-continued

| Compound | % Remaining |
|---|---|
| 67 | 100 |
| 68 | 96 |
| 69 | 92 |
| 70 | 93 |
| 71 | 90 |
| 72 | 88 |
| 73 | 95 |
| 80 | 100 |
| 81 | 100 |
| 82 | 34 |
| 83 | 100 |
| 84 | 100 |
| 85 | 107 |

4. Metabolic Stability Assay

To predict the stability of the compound under first pass (Phase I) metabolism, compounds of the present teachings were incubated with male rat liver microsomes at 1 μM concentration and 0.5 mg/mL protein concentration at 37° C. After 15 min, the reaction was quenched with cold acetonitrile. The solution was centrifuged and the supernatant was analyzed with LC-MS using the HPLC conditions described in section 3 above. The percent remaining was calculated by dividing the 15-minute incubation sample LC-MS area counts by the time=0 area counts, and the half-life of the compound was derived using first-order reaction kinetics. Based on this assay, Compounds 2, 64, 65, 66, 67, 68, 69, 70, 71, 72, 73, 80, 81, 82, 83 and 84 had half-lives greater than 30 minutes in male rat liver microsomes.

5. Canine Infarct Size and Reperfusion Arrhythmia Model

Compound 2 was tested in dogs subjected to a 60-min coronary artery occlusion and 4 hr reperfusion, as described by Hennan et al. (J. Exp. Pharmacol. Ther., 317, 236-43 (2006)). Compound 2 was administered IV 10-min before reperfusion as a bolus+IV infusion at doses of: 0.25 μg/kg bolus+0.19 μg/kg/hr infusion (n=6); 2.5 μg/kg bolus+1.9 μg/kg/hr infusion (n=7); 25 μg/kg bolus+19 μg/kg/hr infusion (n=6); 75 μg/kg bolus+57 μg/kg/hr infusion (n=5); vehicle control (n=7). Premature ventricular complexes (PVC's) were quantified during reperfusion. Four or more consecutive PVC's was defined as ventricular tachycardia (VT). Total incidence of VT was reduced significantly with the two highest doses of Compound 2 (1.7±0.8; 2.2±1.4 events; p<0.05) compared to controls (23.0±6.1). Total PVC's were reduced significantly from 11.1±1.6% in control animals to 2.0±0.7% and 1.8±0.8% after the two highest doses of Compound 2. Infarct size, expressed as percent of left ventricle, was reduced significantly from 19.0±3.5 in controls to 7.9±1.5 and 7.1±0.8% (p<0.05) at the two highest doses of Compound 2. These results demonstrate that compounds of the present teachings are potent antiarrhythmic compounds with cardioprotective effects.

6. In Vitro Cell Swelling and Dye Uptake Model

Peptides capable of demonstrating cytoprotection can be identified in an in vitro model of ischemia induced cell swelling and dye uptake. In this experiment, the effect of Compound 2 on calcein dye-uptake induced by metabolic inhibition in cultured C6 glioma cells overexpressing connexin43 was studied. Cells were incubated under control conditions and during simulated ischemia (SI) for 40 minutes in the presence of calcein (200 μM). Following incubation the cells were subjected to epifluorescence microscopy to determine the uptake of calcein. Incubation of C6 cells in SI medium increased dye-uptake to 5-fold above control values. The uptake was dose-dependently inhibited by Compound 2, and minimum uptake was obtained at 100 μM Compound 2 (32% relative reduction of the SI inducible response; p<0.05 vs. vehicle). Control cells exhibited cell swelling during the 40 min stress period, whereas cells treated with Compound 2 did not.

Variations, modifications, and other implementations of what is described herein will occur to those of ordinary skill in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

The invention claimed is:

1. A method of treating ischemia, or ischemic injury in the organs of a mammal, comprising administering to a subject a therapeutically effective amount of a compound that is

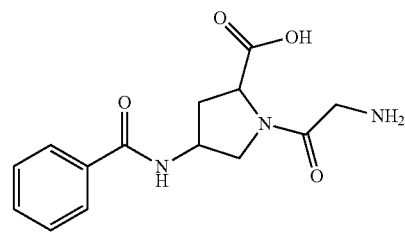 [SMILES: NCC(=O)N1CC(NC(=O)c2ccccc2)CC1C(=O)O]

or a pharmaceutically acceptable salt thereof.

2. The method according to claim 1, for treating acute ischemic heart disease.

3. The method according to claim 1, for treating stable or unstable angina pectoris.

4. The method according to claim 1, for treating acute myocardial infarction.

5. The method according to claim 1, for treating ischemic injury in the gastrointestinal tract.

6. The method according to claim 1, wherein the subject is a human being.

7. The method according to claim 1, wherein the compound is formulated for parenteral or oral administration.

8. A method of treating ischemia, or ischemic injury in the organs of a mammal, comprising administering to a subject a therapeutically effective amount of a compound that is

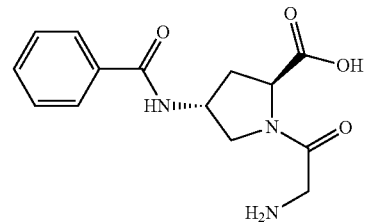 [SMILES: NCC(=O)N1C[C@H](NC(=O)c2ccccc2)C[C@H]1C(=O)O]

or a pharmaceutically acceptable salt thereof.

9. The method according to claim 8, for treating acute ischemic heart disease.

10. The method according to claim 8, for treating stable or unstable angina pectoris.

11. The method according to claim 8, for treating acute myocardial infarction.

12. The method according to claim 8, for treating ischemic injury in the gastrointestinal tract.

13. The method according to claim 8, wherein the subject is a human being.

14. The method according to claim 8, wherein the compound is formulated for parenteral or oral administration.

* * * * *